United States Patent
Gann

(10) Patent No.: US 10,856,703 B2
(45) Date of Patent: Dec. 8, 2020

(54) DEVICES AND SYSTEMS FOR CONTAINING AND DISPENSING LIQUIDS

(71) Applicant: Horizon Home Products, Inc., Denver, CO (US)

(72) Inventor: Derek G. Gann, Denver, CO (US)

(73) Assignee: Horizon Home Products, Inc., Denver, CO (US)

( * ) Notice: Subject to any disclaimer, the term of this patent is extended or adjusted under 35 U.S.C. 154(b) by 0 days.

(21) Appl. No.: 16/514,011

(22) Filed: Jul. 17, 2019

(65) Prior Publication Data

US 2019/0335956 A1 Nov. 7, 2019

Related U.S. Application Data

(63) Continuation of application No. PCT/US2018/013994, filed on Jan. 17, 2018.

(60) Provisional application No. 62/447,458, filed on Jan. 18, 2017.

(51) Int. Cl.
*A47K 5/12* (2006.01)
*A47K 10/34* (2006.01)

(52) U.S. Cl.
CPC ............ *A47K 5/1211* (2013.01); *A47K 10/34* (2013.01); *A47K 2201/02* (2013.01)

(58) Field of Classification Search
CPC ................ A47K 5/1211; A47K 5/1205; A47K 2201/02; A47K 1/08; B65D 25/22
See application file for complete search history.

(56) References Cited

U.S. PATENT DOCUMENTS

| 2,685,365 A | 8/1954 | Sieven |
| 3,837,595 A | 9/1974 | Boone |
| 4,106,616 A * | 8/1978 | Boone ................. A47K 10/32 206/233 |
| 4,106,617 A | 8/1978 | Boone |

(Continued)

FOREIGN PATENT DOCUMENTS

| KR | 20130069130 A1 | 6/2013 |
| WO | WO 2018/136481 A2 | 7/2018 |

OTHER PUBLICATIONS

International Search Report and Written Opinion, International Application No. PCT/US2018/013994, dated Jul. 23, 2018, 26 pages.

*Primary Examiner* — Bradley Duckworth
(74) *Attorney, Agent, or Firm* — William M. Fischer

(57) ABSTRACT

Devices and systems for containing and dispensing liquids are disclosed. The system includes a basket and a container removably coupled to the basket to facilitate nesting in a basket cavity. The container includes a pump assembly coupled to the container and extending into an interior thereof. The system includes at least one hanger arm coupled to the basket. The at least one hanger arm includes a first section proximate the basket and a second section distal the basket, the second portion including a distal end. A device embodiment includes the container having the at least one hanger arm coupled thereto rather than being coupled to the basket. Embodiments of the disclosure provide versatile liquid containing and dispensing devices and systems having low cost and high longevity, and that facilitate convenient co-location of liquid cleaning and personal hygiene products, and related and associated items and materials, to preferred places of use.

30 Claims, 34 Drawing Sheets

(56) References Cited

U.S. PATENT DOCUMENTS

| | | | | |
|---|---|---|---|---|
| 4,110,616 | A | 8/1978 | Boone | |
| 4,235,333 | A | 11/1980 | Boone | |
| 4,301,556 | A | 11/1981 | Schimanski | |
| 4,798,312 | A * | 1/1989 | Scheiber | A47K 10/32 206/233 |
| 4,964,543 | A * | 10/1990 | Scheiber | A47K 10/32 222/180 |
| 5,897,074 | A * | 4/1999 | Marino | A47K 10/38 242/594.1 |
| 6,318,690 | B1 * | 11/2001 | Chang | A47K 1/08 248/312 |
| 6,929,148 | B2 | 8/2005 | Haddad et al. | |
| 7,128,235 | B2 | 10/2006 | Haddad et al. | |
| 7,357,350 | B1 | 4/2008 | Rogers | |
| 7,481,395 | B2 | 1/2009 | Rogers | |
| 8,550,296 | B2 | 10/2013 | Steck et al. | |
| 8,746,498 | B2 * | 6/2014 | Maldonado | A45F 5/02 220/756 |
| 9,131,811 | B2 * | 9/2015 | Wegelin | B05B 11/308 |
| D770,199 | S | 11/2016 | Dorrance | |
| 9,498,088 | B2 * | 11/2016 | Hinson | A47K 3/281 |
| 2005/0035141 | A1 | 2/2005 | Haddad et al. | |
| 2005/0284881 | A1 | 12/2005 | Haddad et al. | |
| 2008/0135675 | A1 | 6/2008 | Rogers | |
| 2008/0169411 | A1 | 7/2008 | Quinn et al. | |
| 2008/0272077 | A1 | 11/2008 | Neher | |
| 2009/0236254 | A1 | 9/2009 | Jenkins et al. | |
| 2010/0187242 | A1 | 7/2010 | Lynch et al. | |
| 2012/0298672 | A1 | 11/2012 | Maldonado et al. | |
| 2012/0305588 | A1 | 12/2012 | Steck et al. | |
| 2012/0305589 | A1 | 12/2012 | Steck et al. | |
| 2013/0076514 | A1 | 3/2013 | Wegelin et al. | |
| 2014/0245533 | A1 | 9/2014 | Lee et al. | |
| 2014/0263909 | A1 | 9/2014 | Tsai | |
| 2015/0182025 | A1 | 7/2015 | Kuo | |
| 2016/0174779 | A1 * | 6/2016 | Yaros | A47K 10/3818 242/594 |
| 2016/0280422 | A1 | 9/2016 | Dorrance | |
| 2019/0193098 | A1 * | 6/2019 | Harbaugh | B05B 9/0822 |

* cited by examiner

DEVICES AND SYSTEMS FOR CONTAINING AND DISPENSING LIQUIDS

CROSS REFERENCE TO RELATED APPLICATIONS

This application is a continuation of International Patent Application No. PCT/US2018/013994 (filed Jan. 17, 2018), which claims priority to U.S. Provisional Patent Application No. 62/447,458 (filed Jan. 18, 2017), both of which are incorporated herein in their entireties.

TECHNICAL FIELD

This invention generally relates to devices and systems that are useful for containing at least one liquid and dispensing desired volumes of the at least one liquid by user(s) to desired locations. More specifically, the devices and systems described herein relate to liquid containment and dispensing apparatus which include structural features and components in addition to containers and pump assemblies having utility to user(s) for a variety of purposes and in a variety of locations.

BACKGROUND

Some known devices and systems for providing users convenient co-location of cleaning and personal hygiene products to their preferred place of use include containers that are not intended for containing and dispensing liquids, but rather are designed for containing disposable cleaning cloths. In such known devices and systems, cleaning cloths (e.g., disposable wet-wipes) pose the problem of clogging sewer pipes and plumbing networks when flushed down toilets, leading to costly repairs. Even though many wipes claim to be flushable, at least some such wet-wipes are thicker and more durable than bathroom tissue and thus do not disintegrate readily in the sewer system. The wipes often combine with other materials, such as congealed organic matter and/or grease, to create virtually indestructible clogs. Further, some known devices and systems employ plastic containers for containing and dispensing wet-wipes, and such plastic containers are also intended to be disposable by users along with individual wet-wipes dispensed therefrom. Thus, such known devices and systems pose undesirable environment and other health concerns due to, for example, bulky and nonbiodegradable plastic containers and slowly- or non-degrading wet-wipes entering freshwater supplies and other bodies of water like oceans. An added expense and concern of such known devices and systems includes, for example, a high cost of production of the disposable containers and the disposable wet-wipes, along with the inability of users to refill the containers employed therefor.

Other known devices and systems for providing users convenient co-location of cleaning and personal hygiene products to their preferred place include structural pieces that facilitate removable attachment of the devices and systems by users from one place to another place. For example, in at least some such known devices and systems, a container (e.g., disposable container for wet-wipes) is coupled to at least one hanger piece for removable attachment to structural features (e.g., paper towel roll rods and hooks attached to walls) commonly found in household, business, and industrial buildings. Although such known devices and systems allow users to move the location of cleaning and/or personal hygiene products from one place to another, users do not benefit from a modular design. Lack of modularity in such known devices and systems disadvantages users by, for example, preventing them from easily refilling the containers with additional cleaning material, necessitating users having to purchase multiple devices and systems, and/or install a plurality of supportive structures to facilitate employing a plurality of desired cleaning products in a plurality of locations, taking up otherwise useable space with the plurality of non-modular and non-refillable devices and systems, and compounding the environment and health concerns described above.

Furthermore, pump assemblies are not modularly integrated into known devices and systems for providing users convenient co-location of cleaning and personal hygiene products to their preferred place. In known devices and systems including pump assemblies, their use is paired with instability of, for example, the apparatus hanging from a supportive member. Such known apparatus may require the use of two hands, which detracts from convenience and/or ergonomic advantages. Further, structural instability during operation of known apparatus, including those which include pump assemblies, tend to cause repeated contact (e.g., bumping, shaking, vibration, etc.) with supportive structures such as walls and rods, which leads to undue wear and sooner replacement and/or maintenance times of supportive structures and components of known apparatus, which further increase short- and long-run costs to users of known devices and systems.

Also, the structural pieces that facilitate removable attachment of the devices and systems by users in known devices and systems are themselves not modular and/or adjustable. Thus, users are required to purchase, install, and employ a plurality of devices and systems to enjoy a plurality of cleaning products co-located at a plurality of locations. Likewise, users of known devices and systems are unable to easily utilize a single apparatus in a plurality of desired locations without also having to install and/or move an appropriate supportive structure in the plurality of locations. Furthermore, known devices and systems for providing users convenient co-location of cleaning and personal hygiene products are not accommodatable to varying physiological characteristics of different users, and are further not easily employed in contexts where a specific user desires to adjust particular configurations of use to his or needs and desires (e.g., containing and dispensing a plurality of liquids from a single unit of the device or system).

Although at least some known apparatus include structural hanging pieces intended to lend stability to the containment and dispensing unit, such known apparatus maintain this stability during use only in a limited set of locations, and use conditions and configurations. While such known devices and systems provide convenience and ergonomic benefits to users in one location and for one particular user, the same unit selected from among such known devices and systems provides comparatively little or no convenience and/or ergonomic advantage to the same user in a different location. Users desiring to employ one or more of such known devices and systems in a number of locations, and use conditions and configurations therefore are presented with a very limited number of choices, and must search for and purchase a plurality of different units from a plurality of different vendors. For example, and without limitation, having purchased one of a known apparatus for use in a bathroom, the user must purchase a second unit for a kitchen where the shapes and sizes of available supportive structures differs significantly from the bathroom. Such a user of a known system and method often desires to extract significant value from a purchase he or she makes, and to accomplish that goal, desires to employ versatile and modular devices and systems for the aforementioned cleaning and personal hygiene uses, and other suitable uses. Known systems and methods are ill-suited to accomplishing this and other goals of users because they lack the low-cost of manufacture and use, they are not modular, versatile, and refillable, they pose waste, health, and environment concerns, and they do not maintain stability during use in more than a very limited set of locations, conditions, and configurations.

SUMMARY

Device and systems according to the present Application present straightforward and manageable solutions to address the above discussed disadvantages of known devices and systems for containing and dispensing liquids. The devices and systems shown and described herein are comparatively more cost-effective for manufactures and users, and are also comparatively more convenient, modular, and versatile. The several novel and advantageous aspects of the devices and systems herein described enable users to co-locate liquid cleaning and personal hygiene products with desired use locations, to employ a single unit with a wide variety of differing liquids, pump assembly types, and different user preferences (e.g., guests and/or employees of user), and in a wide variety of use locations and use configurations.

In one aspect, a device for containing and dispensing a liquid is provided. The device is alternately attachable to and removable from a supportive structure. The device includes a container. The container includes a container base and at least one container side wall. The at least one container side wall includes a base edge coupled to the container base and a top edge opposite the base edge. The top edge defines an at least partially open container top opposite the container base. The container has a volume defined by the container base and the at least one container side wall extending generally upward from the container base. The container also includes a container opening defined in the container top. The container opening facilitates access from an exterior of the container to an interior cavity thereof. The interior cavity is defined by the container base, the at least one container side wall, and the at least partially open container top. The container further includes a pump assembly coupled to the container top and extending through the container opening into the interior cavity. The pump assembly is configured for selective dispensing of a fractional volume of the liquid from the interior cavity to the exterior. The fractional volume is less than the volume of the container. The device also includes at least one hanger arm coupled to the container and extending generally upward therefrom. The at least one hanger arm includes a first section proximate the container and a second section distal the container. The second portion includes a distal end configured for the alternate attachment to and removal from the supportive structure.

In another aspect, a system for containing and dispensing a liquid is provided. The system is alternately attachable to and removable from a supportive structure. The system includes a basket. The basket includes a basket base and at least one basket side wall including a basket base edge coupled to the basket base. The basket also includes a basket top edge opposite the basket base edge and defining an at least partially open basket top opposite the basket base. The basket has a basket volume defined by the basket base and the at least one basket side wall extending generally upward from the basket base. A basket opening defined in the basket top facilitates access from an exterior of the basket to a basket cavity thereof defined by the basket base and the at least one basket side wall. The system also includes at least one container removably coupled to the basket to facilitate nesting therein through the basket opening. The at least one container includes a container base and at least one container side wall. The at least one container side wall includes a base edge coupled to the container base and a top edge opposite the base edge. The top edge defines an at least partially open container top opposite the container base. The container has a volume defined by the container base and the at least one container side wall extending generally upward from the container base. The at least one container also includes a container opening defined in the container top. The container opening facilitates access from the exterior of the at least one container to an interior cavity thereof. The interior cavity is defined by the container base, the at least one container side wall, and the at least partially open container top. The container further includes a pump assembly coupled to the container top and extending through the container opening into the interior cavity. The pump assembly is configured for selective dispensing of a fractional volume of the liquid from the interior cavity to the exterior. The fractional volume is less than the volume of the container. The system further includes at least one hanger arm coupled to the basket and extending generally upward therefrom. The at least one hanger arm includes a first section proximate the basket and a second section distal the basket. The second portion includes a distal end configured for the alternate attachment to and removal from the supportive structure.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

Figure 1:
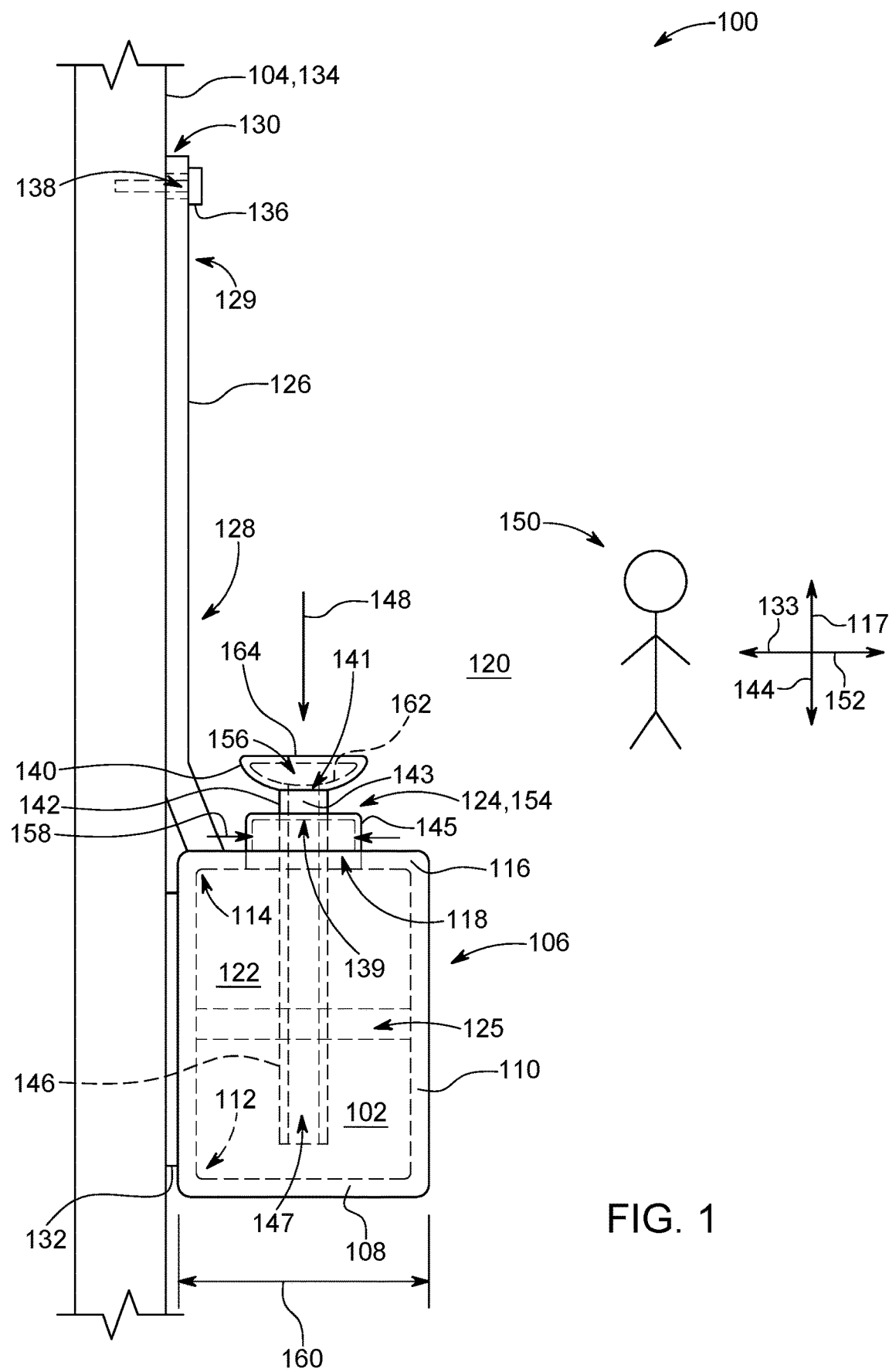
FIG. 1 is a side-view diagram of an embodiment of a device for containing and dispensing a liquid.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, and such ranges are identified and include all the sub-ranges contained therein unless context or language indicates otherwise.

Through this detailed description and the drawings, directional terminology is employed for purposes of convenience. For example, the words upward, downward, leftward, and rightward are used to place features and components of the disclosed devices and systems in position with respect to one another. Although use of such terms assist in understanding the disclosure and relating the drawings to the corresponding textual description, these directional terms are not meant to meaningfully limit the disclosure, unless the context clearly indicates otherwise. Thus, where a first set of at least one feature of the devices and systems is described as being to the left of and/or on top of a second set of at least one feature in an illustrated embodiment, other embodiments which are not shown include the first set feature(s) being to the right of and/or underneath the second set feature(s). A person having ordinary skill in the art will recognize and appreciate variations such as these, and will similarly understand that, although embodiments of the disclosed devices and systems are illustrated to include embodiments that are symmetric about respective axes of symmetry, unless context clearly indicate otherwise, such symmetry may not be required for their form and function.

Also, in the following detailed description and the claims, the terms "nest", "nesting," and "nestingly" refer to properties of geometric shapes of various features and components of the devices and systems described herein. For example, at least a portion of a first component has a first shape (e.g., a five pointed star shape), and at least a portion of a second component has a second shape (e.g., a five pointed star shaped cavity defined and formed in a surface of the second component). Thus, the five pointed star shaped portion of the first component is designed and intended to nest into and within the five pointed star shaped cavity portion of the second component. Likewise, when the five pointed star shaped portion of the first component is inserted (e.g., removably inserted) into the five pointed star shaped cavity (e.g., receptacle) portion of the second component, the first component is thereby "nesting" (e.g., "nested") in the aforementioned cavity of the second component. Similarly, in this terminology usage example, the five pointed star shaped portion of the first component is "nestingly" inserted into the five pointed star shaped cavity portion of the second component, and the five pointed star shaped cavity is thus "nestingly" shaped. Further, certain features and components of the devices and systems described herein are "nested" to one another to provide and facilitate removable and sliding coupling of two components. Certain other features and components of the devices and systems described herein are "nested" to one another to provide, when and where desired, selective and alternating adjustment of positions of them relative to one another. Thus, when a position of a third component is desired to be affixed and secured relative to a position of a fourth component, a portion of the third component is nested to a corresponding portion of the fourth component. When the position of the third component is desired to be adjusted relative to the position of the fourth component, the portion of the third component is removed (e.g., de-nested) from the corresponding portion of the fourth component.

The devices and systems for containing and dispensing liquids described herein provide convenient co-location of liquid cleaning and personal hygiene products, and related and associated items and materials, to preferred places of use. The embodiments described herein also provide for co-location of cloths, towels, swabs, pads, wipes with liquid containers having conveniently operated pump assemblies, and which are readily exchangeable and refillable by users. These embodiments shown and described below are compact, modular, versatile, and manufactured and assembled in a cost-effective and efficient manner from a variety of low cost, but durable and long-lasting materials. Component parts of the devices and systems described herein need not be strictly disposable, but rather one or more of the component parts may be re-usable by users over longer periods of time as compared to known apparatus, thereby mitigating undesirable negative impacts to water quality and environmental and human health due to slower biodegradation of disposable materials in known apparatus. The devices and systems for containing and dispensing liquids described herein further provide sturdy and stable structural features and components to facilitate removable attachment of the apparatus herein disclosed from one place to another place. Through modularity of design, the embodiments described herein reduce the need of users to purchase a plurality of different units to use in a plurality of different locations within home, business, and industrial settings. The modular and adjustable features and components in the disclosed embodiments also reduces the need of users to install a plurality of supportive structures to facilitate mounting and employing a plurality of desired liquid products in a plurality of locations, which would take up otherwise useable space, and would compound the environment and health concerns described above. The devices and systems for containing and dispensing liquids described herein also modularly and effectively integrate pump assemblies into their design to provide numerous benefits to users including, without limitation, stability of the disclosed apparatus during pumping motions, speed, convenience, and ergonomic advantages (e.g., requiring using only one hand to transfer desired volumes of liquid out of containers by pumping) to users during the various manipulations of the apparatus during operation, as described below. Moreover, the embodiments described herein provide stable and sturdy, yet removable attachment (e.g., through hanging attachment) of the apparatus to a wide variety of shapes, sizes, and types of supportive structures, which reduces undesired recurrent contact (e.g., bumping) of the disclosed apparatus relative to known devices and systems. Structural pieces of the embodiments described below further include modular and adjustable features to facilitate accommodating a single unit of the apparatus to a plurality of locations, installation methods, user preferences, user physiological characteristics, and varying shapes, sizes, and types of available supportive structures. The versatility thus provided by the devices and systems for containing and dispensing liquids described herein provides users low cost and high longevity apparatus which facilitate convenient co-location of liquid cleaning and personal hygiene products, and related and associated items and materials, to preferred places of use.

FIG. 1 is a side-view diagram of an embodiment of a device (e.g., a device 100) for containing and dispensing a liquid 102. Device 100 is alternately attachable to and removable from a supportive structure 104 including, for example and without limitation, a substantially vertical surface 134 such as a wall. Device 100 includes at least one container 106. Container 106 includes a container base 108 and at least one container side wall 110. In the embodiment shown in FIG. 1, container 106 is substantially cubic in shape and thus includes four container side walls 110, with container base 108 having four sides. In other embodiments, not shown, container 106 is circularly cylindrically-shaped or ellipsoidal cylindrically-shaped and thus includes one container side wall 110, with container base 108 having one side defined by a circumference. In still other embodiments, not shown, container 106 has greater than four container side walls 110 corresponding to greater than four sides of container base 108 (e.g., pentagonal or greater polygonally-shaped container bases 108).

Container side wall 110 includes a base edge 112 coupled to container base 108. Container side wall 110 also includes a top edge 114 positioned opposite base edge 112. Top edge 114 defines an at least partially open container top 116 opposite container base 108. Container base 108 and the at least one container side wall 110 extend generally upward 117 from container base 108 to define a container cavity of the container 106 having a predetermined volume. Volume of container 106 is thus based on the various dimensions of container base 108 and the at least one container side wall 110. Container top 116 includes a container opening 118 defined therein. Container opening 118 provides and facilitates access from an exterior 120 of container 106 to an interior cavity 122 of container 106. Interior cavity 122 is, therefore, defined by container base 108, the at least one container side wall 110, and the at least partially open container top 116.

Device 100 also includes a pump assembly 124 coupled to container top 116. In the embodiment shown in FIG. 1, pump assembly 124 is removably coupled to container top 116 as, for example, through screw threads or via a snap-fitting. In other embodiments, not shown, pump assembly 124 is not removably coupled to container top 116. Instead, in such other embodiments, at least a portion of pump assembly 124 is integrally formed with container top 116. Also, container top 116 in the embodiment shown in FIG. 1 is integrally formed with container side wall 110 and container base 108 and, thus, container 106 is one piece. In other embodiments, not shown, container top 116 is not integrally formed with container side wall 110 and container base 108. In such other embodiments, container top 116 is removably coupled to the at least one container side wall 1 10 as, for example, through screw threads or via a snap-fitting. Also, in the embodiment shown in FIG. 1, pump assembly 124 extends through container opening 118 into interior cavity 122.

Device 100 further includes at least one hanger arm 126 coupled to container 106. The at least one hanger arm 126 extends distally from the container 106. In one embodiment, the at least one hanger arm 126 extends generally upward 117 from container 106. In the embodiment shown in FIG. 1, hanger arm 126 includes a first section 128 proximate container 106. Hanger arm 126 also includes a second section 129 positioned adjacent first section 128. Second section 129 is distal container 106 and includes a distal end 130. Also, in the embodiment shown in FIG. 1, first section 128 and second section 129 are integrally formed into a one-piece hanger arm 126. In other embodiments, not shown, hanger arm 126 is not integrally formed as one piece, but rather is formed from at least two pieces including first section 128 and second section 129. Further, in the embodiment shown in FIG. 1, hanger arm 126, container top 116, the at least one container side wall 110, and container base 108 are integrally formed as one piece. In other embodiments, not shown, hanger arm 126 is not integrally formed with container top 116, the at least one container side wall 110, and container base 108. In such other embodiments, the at least one hanger arm 126 is removably coupled to at least one of container top 116, container side wall 110, and container base 108, as, for example, through a snap-fit mechanism. In still other embodiments, not shown, at least one hanger arm 126 is non-removably secured to at least one of container top 116, container side wall 110, and container base 108. Device 100 further includes at least one bumper 132 coupled to at least a portion of a rearward 133 facing portion of at least one of container 106 and the at least one hanger arm 126. In other embodiments, not shown, device 100 does not include bumper 132.

In the embodiment shown in FIG. 1, pump assembly 124 includes a lid 145 coupled to container top 116. Lid 145 includes a lid opening 139 defined therein which provides and facilitates access from exterior 120 of container 106 to interior cavity 122 of container 106 when lid 145 is coupled to container top 116. Pump assembly 124 also includes a dispenser 140 including a dispenser opening 141 defined therein. Pump assembly 124 further includes a first tubular extension 142 slidingly coupled to lid 145 through the lid opening 139. First tubular extension 142 is further coupled to dispenser 140. First tubular extension 142 extends generally downward 144 from dispenser 140 to lid 145. Lid 145 and dispenser 140 are spaced apart by a predetermined, non-zero-valued distance defined by a length of the first tubular extension 142. First tubular extension 142 includes a first tube section 143 that is generally aligned with dispenser opening 141.

Pump assembly 124 also includes a second tubular extension 146 coupled to the first tubular extension 142. Second tubular extension 146 includes a second tube section 147 that is aligned with first tube section 143. In the embodiment shown in FIG. 1, first tubular extension 142 and second tubular extension 146 are integrally formed as one piece, with the second tubular extension 146 extending generally downward 144 from container top 116 into interior cavity 122 to a predetermined non-zero-valued distance from the container base 108. In other embodiments, not shown, first tubular extension 142 and second tubular extension 146 are not integrally formed as one piece. Instead, in such other embodiments, first tubular extension 142 is slidingly coupled to both lid 145 and to second tubular extension 146, while second tubular extension 146 is securely and non-slidingly coupled to at least one of lid 145 and container top 116.

As shown in FIG. 1, pump assembly 124 of device 100 is embodied in a dish-top pump 154. Dish-top pump 154 includes lid 145 coupled to container top 116 as described above. Dispenser 140 of dish-top pump 154 includes a dish 156 having dispenser opening 141 defined in a bottom 162 of dish 156 opposite a top 164 of dish 156. Other types of dispensers 140 other than dish-top pump 154 are employed in device 100 in addition to or instead of dish-top pump 154.

Figure 3:
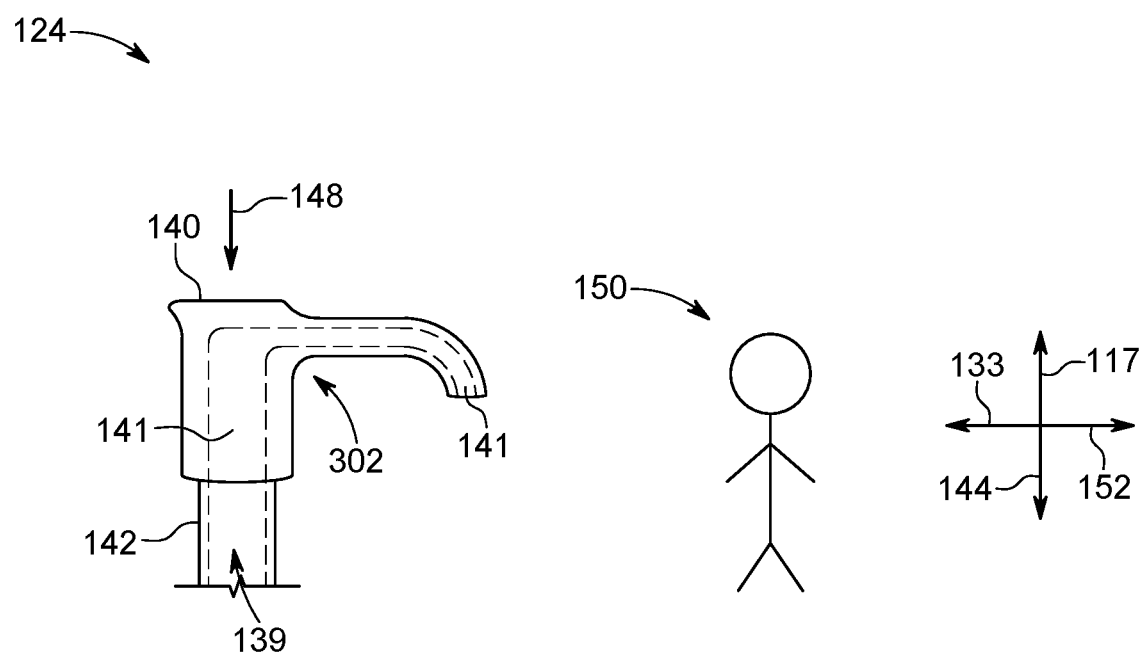
FIG. 3 is a side-view diagram of an alternative embodiment of a pump assembly dispenser shown in FIGS. 1 and 2.

Referring now to FIG. 3, for example and without limitation, a device 300 includes pump assembly 124 having dispenser 140 embodied in a faucet-top pump 302. Generally, pump assembly 124 retains common features described above with reference to FIG. 1 and device 100, except for the particular form taken by dispenser 140 (e.g., dish-top pump 154 versus faucet-top pump 302).

A person having ordinary skill in the art will recognize and appreciate that the disclosed devices and systems readily employ numerous types of pumps to accomplish the functionality described herein, including, without limitation, manually-operated pumps such as those illustrated in FIGS. 1 and 3, but also pumps that employ electromechanical (e.g., motors) and other components (e.g., vacuum, hydraulic) that assist a user 150 of device 100 to remove a desired amount of liquid from interior cavity 122 of container 106 to exterior 120. Such assistive components for pumping liquid from container 106 are desirable in several contexts, including, without limitation, where device 100 and the various other embodiments described below are used by individuals having various handicaps and/or injuries that impede manual dexterity and/or strength.

Figure 2:
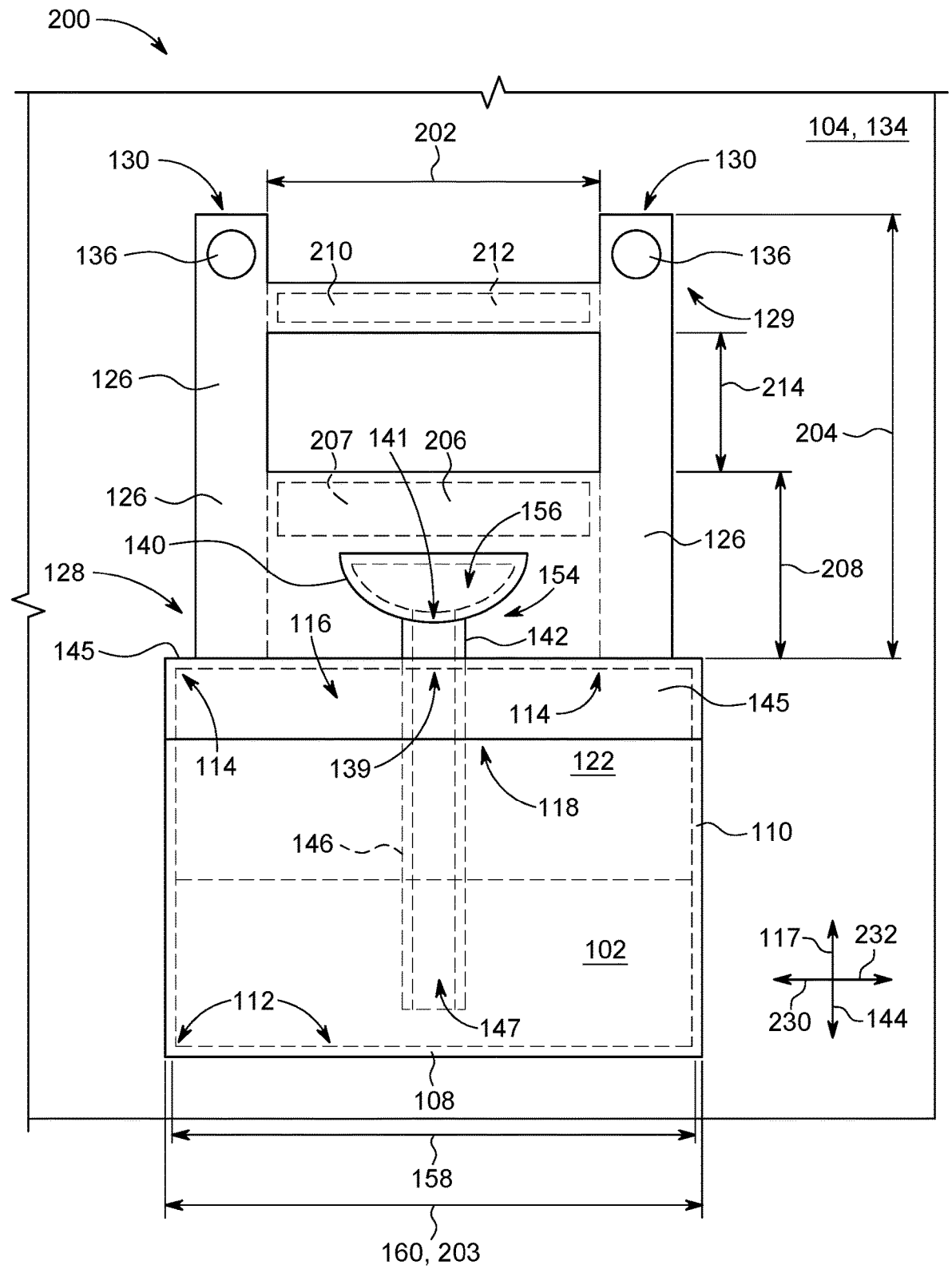
FIG. 2 is a front-view diagram of an alternative embodiment of a device for containing and dispensing a liquid.

Further, as shown in FIG. 1, container top 116 is embodied in a partially open container top 116. As such, container opening 118 has an opening size 158 that is less than a container width 160 of the container 106. In those embodiments in which container 106 is embodied in a circular or ellipsoidal cylindrically-shaped container 106, container width 160 is defined as a container diameter 203 (as shown in FIG. 2 below).

Lid 145 covers the container opening 118. User 150 couples lid 145 to container opening 118 to cover container opening 118 during use and/or storage of device 100. Also, in use of device 100, lid 145 is removed from container opening 118 when user 150 desires to add more liquid 102 to container 106, replace the liquid 102 in container 106 with a different liquid 102, and/or wash the interior cavity 122 of container 106. In other embodiments, not shown, container 106 includes a level sensor which provides and facilitates the user 150 having the ability to determine and/or estimate a present volume of liquid 102 in container 106 without having to open lid 145. Level sensor includes analog and/or digital components which sense the level of liquid 102 in interior cavity 122 and provide a visual indication (e.g., light changing from first color indicating the volume of liquid 102 being greater than a predetermined volume to a second color indicating the volume of liquid 102 being less than or equal to the predetermined volume) to the user 150 containing this information. In still other embodiments, device 100 includes a communication subsystem which transmits (e.g., by a wired and/or wireless data communication protocol) the information about the present level and/or the present volume of liquid 102 in interior cavity 122 to a location distal the container 106 (e.g., to an application, i.e., "app", of a smartphone of the user 150). Furthermore, communication subsystem, in some device embodiments, communicates with a vendor to place an order for user 150 to at least one of purchase, initiate shipping, initiate delivery, and receive additional volume(s) of liquid(s) 102 sufficient to refill container 106 when the present volume and/or the present level of liquid 102 in interior cavity 122 becomes less than or equal to the predetermined volume. In yet other embodiments, not shown, container 106 and/or pump assembly 124 includes a counter sensor (e.g., an accelerometer) which counts the number of times user 150 pumps the pump assembly 124 (e.g., applies the downward 144 force 148 thereto). Through correlation of the factional volume 125 per application of downward 144 force 148 by user 150, counter sensor notifies user 150 upon the number of pumps reaching a number that is representative of a predetermined remaining volume of liquid 102 in interior cavity 122 (e.g., the fractional volume 125 being less than the maximum volume of liquid 102 that is containable by container 106). This notification includes information, and the notification is transmitted to and/or visualized by user 150 through one or more of the communication methods described above. User 150 is also provided with the ability to determine the present volume of liquid 102 in interior cavity 122 of container 106 through utilizing an at least partially transparent material of construction for at least a portion of container side wall 110 and/or container top 116.

Also, in the embodiment shown in FIG. 1, first tubular extension 142 includes a first tube section 143 that is generally aligned with dispenser opening 141 to provide and facilitate access to the interior cavity 122 through the dispenser opening 141. Further, in embodiments of device 100 where first tubular extension 142 and second tubular extension 146 are continuous and substantially formed as a one-piece construction, a bottom 144 end of second tubular extension 146 is positioned above 117 base 108 by a distance that is greater than or equal to a length of first tubular extension 142 slidingly coupled to lid 145 through the lid opening 139 (e.g., the distance between top 117 of lid 145 and bottom 144 of dish 156). In other embodiments, not shown, second tubular extension 146 and first tubular extension 142 are not continuously formed as a one-piece construction. In such other embodiments, a top 117 end of second tubular extension 146 is nested within a bottom 144 end of first tubular extension 142 and first tubular extension 142 is slidable over the top 117 end of second tubular extension 146. Second tubular extension 146 in these other embodiments is coupled to lid 145 at lid opening 139. As such, the bottom 144 end of second tubular extension 146 is positioned above 117 base 108 by a distance greater than zero, but need not be positioned above 117 base 108 by a distance that is greater than or equal to the length of first tubular extension 142. Further, in such other embodiments described above, pump assembly 124 is able to access liquid 102 from interior cavity 122 down to a lower level and to a lower volume relative to embodiments of the device having the first tubular extension 142 continuously formed with the second tubular extension 146 as a one-piece construction.

Dispenser 140 of pump assembly 124 receives a force 148 having a downward 144 force vector component from user 150. In the example embodiment, during operation, user 150 is positioned generally frontward 152 of device 100 and supportive structure 104. Application by user 150 of the downward 144 force 148 vector component provides and facilitates pump assembly 124 having the ability to transfer the fractional volume 125 of liquid 102 from interior cavity 122 to the exterior 120. By this pumping action of user 150 manipulating pump assembly 124 in the aforementioned manner, the fractional volume 125 is thus transferred generally upward 117 from interior cavity 122 through the second tubular extension 146, the first tubular extension 142, and the dispenser opening 141. In one use case in particular, user 150 applies the downward 114 force 148 to pump assembly 124 with his or her hand (not shown) holding a fabric cloth or paper towel, the cloth or towel at least partially covering the dispenser opening 141. The fractional volume 125 is thereby transferred from interior cavity 122 to the cloth or the towel, and user 150 then uses the wetted cloth or towel as desired at a location or locations distal pump assembly 124 (e.g., on his or her body and/or on surfaces located in the vicinity of or distal device 100). In another example use case, user 150 of device 100 applies the fractional volume 125 of liquid 102 directly to the hand (e.g., hand sanitizer) and applies the downward 144 force 148 to pump assembly 124 without also holding a cloth or towel. In yet another use case, pump assembly 124 dispenses fractional volume 125 of liquid 102 as a spray and/or mist (e.g., an air freshener).

In each of the example use cases provided above, and in many others that a person having ordinary skill in the art will recognize and appreciate, user 150 repeats the application of the downward 144 force 148 to pump assembly 124 if desired to obtained the desired amount of liquid 102 transfer from interior cavity 122 to exterior 120 of device 100. To reset the pump assembly 124 to its fully upright 117 position after user 150 applies the downward 144 force 148 to pump assembly 124, pump assembly 124 includes a spring (not shown) positioned proximate dispenser 140 and/or lid 145. Thus, a restoring force of the compressed spring returns the pump assembly 124 to its fully upright 117 position, whereby pump assembly 124 is again ready to dispense an additional aliquot of the fractional volume 125 of liquid 102. In the embodiments of the devices (e.g., device 100) including dish-top pump 154, the dispenser 140 thereof contains the fractional volume 125 of liquid 102, where, for example, user 150 can utilize a cloth or towel to wick the factional volume 125 out of the dish 156.

In the devices shown and described herein, bumper 132 provides several benefits during use. Bumper 132 is formed of a material that is generally softer and more pliable than materials of construction of the rest of the device (e.g., device 100). For example, and without limitation, bumper 132 protects substantially vertical surface 134 (e.g., wall) from wear due to repeated applications of force 148 by user 150. Also, for example, bumper 132 mitigates undesired movements of the device (e.g., device 100) before, during, and/or after application of force 148 by user 150. Bumper 132 further provide additional benefits in the various embodiments of the devices described herein, of which persons having ordinary skill in the art will recognize and appreciate.

Furthermore, the devices shown and described herein (e.g., device 100) are removably attached to supportive structure 104 through the alternate attachment to and removal of the second portion 129 of the at least one hanger arm 126 (including distal end 130) from the supportive structure 104. In the embodiment shown in FIG. 1, for example, at least one fastener hole 138 is defined (e.g., formed) through at least one portion of hanger arm 126 (e.g., in at least one location on second portion 129 proximate distal end 130). A fastener 136 is selectively insertable and removable through and from, respectively, the fastener hole 138 by user 150. Thus, fastener 136 and fastener hole 138 provides and facilitates user 150 having the ability to alternately and selectively attach and remove device 100 to and from, respectively, supportive structure 104.

FIG. 2 is a front-view diagram of an embodiment of a device (e.g., a device 200) for containing and dispensing a liquid 102. Device 200 is alternately attachable to and removable from supportive structure 104. Device 200 includes at least one container 106, as shown and described above with reference to FIG. 1. As compared to device 100, in device 200, container top 116 is fully open, and container opening 118 has opening size 158 that is substantially equal to the container width 160 (or, in circular or ellipsoidal cylindrically-shaped embodiments of container 106, the container diameter 203). Thus, in embodiments such as device 200 where container top 116 is fully open, interior cavity 122 is further defined by pump assembly 124.

In the embodiment shown in FIG. 2, device 200 includes two hanger arms 126 spaced apart by a lateral distance 202. Each hanger arm 126 of the two hanger arms 126 in device 200 extends generally upward 117 from the container 106 by an arm distance 204. Device 200 also includes a brace 206 coupled to and extending laterally between each hanger arm 126 of the two hanger arms 126 proximate the first sections 128 thereof. Brace 206 is further coupled to container 106 proximate container top 116 at a rearward 133 facing side thereof. Brace 206 extends generally upward 117 from container top 116 by a brace height 208. In other embodiments, not shown, brace 206 is not further coupled to container 106. In still other embodiments, not shown, device 200 includes a plurality of braces 206 coupled to and extending laterally between each hanger arm 126 of the two hanger arms 126 proximate the first sections 128 thereof. In such other embodiments having a plurality of braces 206, one brace 206 of the plurality of braces 206 is, optionally, further coupled to container 106, as described above. Also, in the embodiment shown in FIG. 2, the brace height 208 is less than or substantially equal to half the arm distance 204. In other embodiments, not shown, the brace height 208 is greater than half the arm distance 204, including, for example, the brace height 208 being substantially equal to the arm distance 204.

Device 200 also includes a brace bumper 207 coupled to a rearward 133 side of brace 206. In other embodiments, not shown, device 200 does not include brace bumper 207. Also, in the embodiment shown in FIG. 2, device 200 further includes a cross-piece 210 coupled to an extending laterally between each hanger arm 126 of the two hanger arms 126 proximate the second sections 129 thereof. In other embodiments, not shown, device 200 does not include cross-piece 210. In still other embodiments, not shown, device 200 includes a plurality of cross-pieces 210 coupled to and extending laterally between each hanger arm 126 of the two hanger arms 126 proximate the second sections 129 thereof. In embodiments having cross-piece 210, device 200 also includes a cross-piece bumper 212 coupled to a rearward 133 facing portion of cross-piece 210. In other embodiments, not shown, device 200 does not include cross-piece bumper 212. Furthermore, in the embodiment shown in FIG. 2, cross-piece 210 is spaced from the brace 206 by a vertical distance 214.

Moreover, in the embodiment shown in FIG. 2, brace 206 and cross-piece 210 provide further structural support and rigidity to the two hanger arms 126 of device 200. Brace bumper 212 and cross-piece bumper 207 provide substantially similar benefits to device 200 as bumper 132 provides to device 100, as shown and described above with reference to FIG. 1. Brace 206 provides further benefits to user 150 during operation of device 200. For example, and without limitation, brace 206 functions as a splash guard in device 200. Thus, brace 206 prevents liquid 102 from contacting, for example, substantially vertical surface 134 to the rear 133 of pump assembly 124 on account of user 150 inadvertently spilling, spraying, splashing, and/or dripping liquid 102 from dish 156 of dish-top pump 154 before, during, and/or after application of the downward 144 force 148 to pump assembly 124. In one embodiment, not illustrated, the brace 206 is coupled to the two hanger arms 124, but is not also coupled to the container 106. In yet another embodiment, not shown, a splash guard may be coupled to the container 106 rearward 133 of the pump assembly 124, extends upward 117 from the container 106, but is not also coupled to either or both of the two hanger arms 126.

Figure 4:
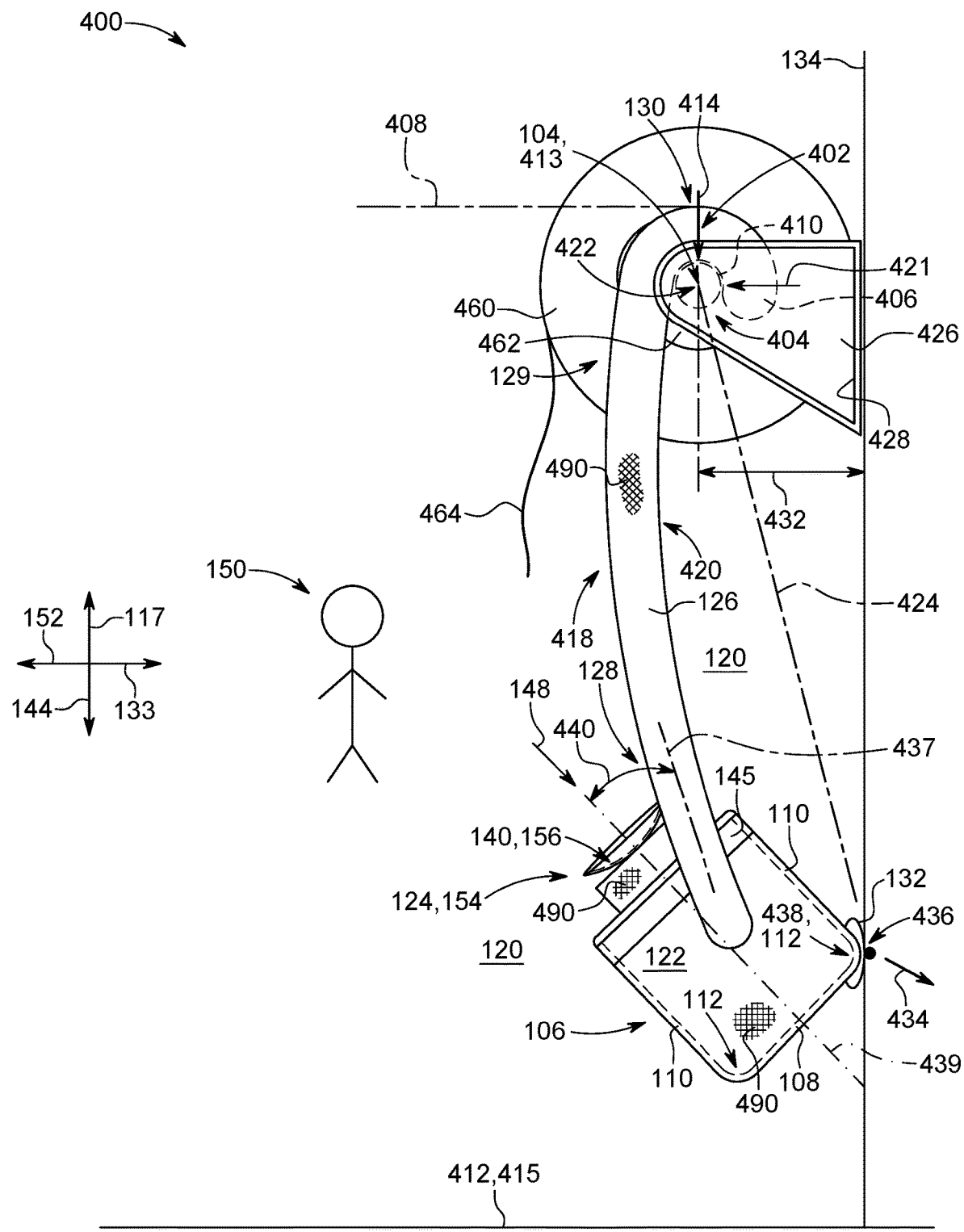
FIG. 4 is a side-view diagram of another embodiment of a device for containing and dispensing a liquid.

FIG. 4 is a side-view diagram of another embodiment of a device 400 for containing and dispensing a liquid. Device 400 includes container 106, pump assembly 124 (embodied in dish-top pump 154), and at least one hanger arm 126, as shown and described above with reference to FIGS. 1 and 2. Similarly, device 400 is alternately attachable to and removable from supportive structure 104. In this embodiment, the distal end 130 of hanger arm 126 is formed as a generally downward 144 facing hook 402. Hook 402 includes a shank 406 spaced apart from at least a portion of the second section 129 of hanger arm 126. Shank 406 extends generally downward 144 from an upper 117 extent 408 (an uppermost 117 upward 117 facing surface of the hanger arm 126 of the distal end 130). The space defined by the shank 406 and the second section 129 defines a slot 404 therebetween. In the embodiment shown in FIG. 4, the at least one hanger arm 126 is formed as an arcuate hanger arm 126. Arcuate hanger arm 126 includes a frontward 152 facing convex side 418 and a rearward 133 facing concave side 420. In other embodiments, not shown, arcuate hanger arm 126 has the opposite curvature. In such other embodiments, convex side 418 is the rearward 133 facing side and concave side 420 is the frontward 152 facing side.

Figure 5:
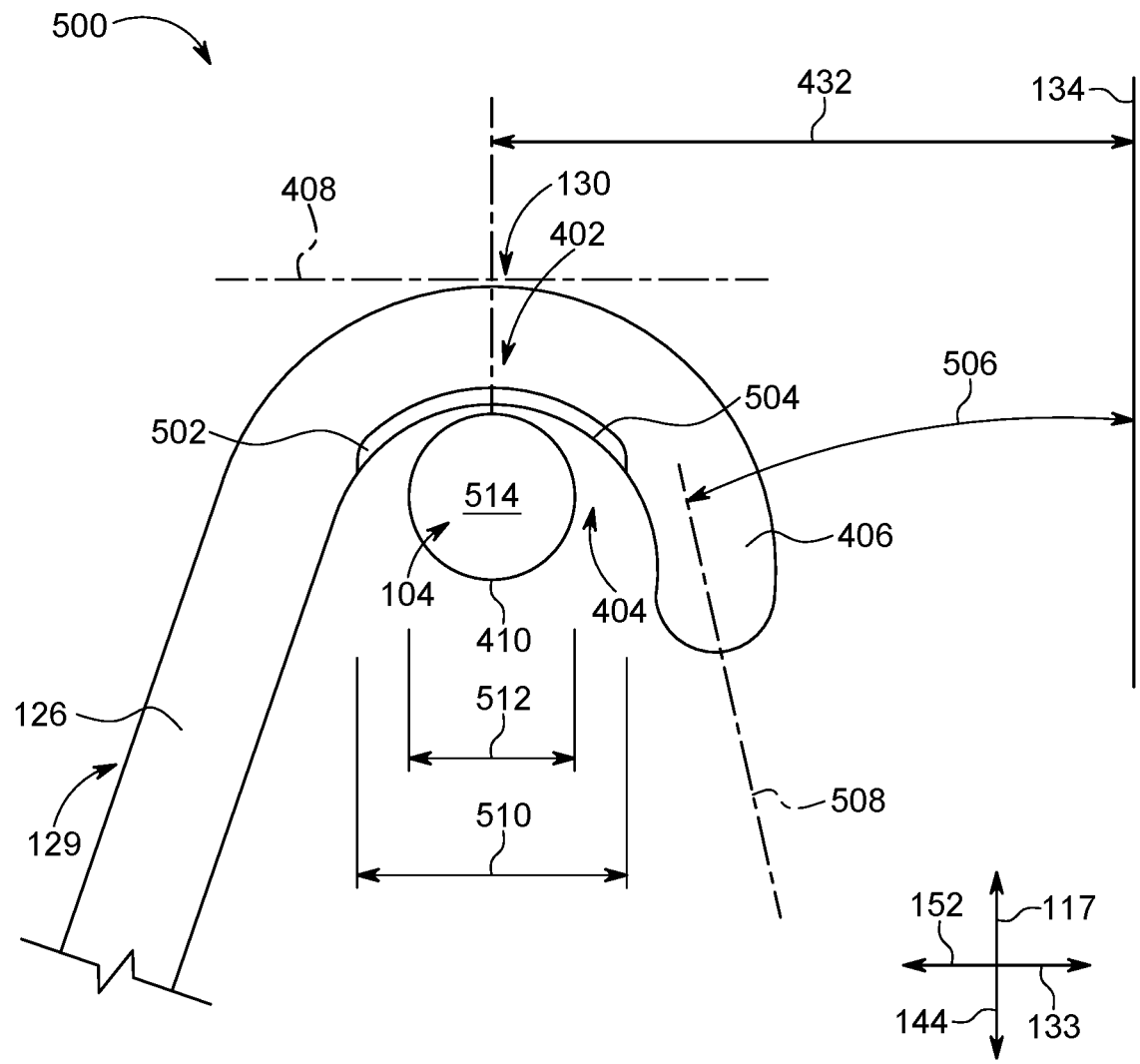
FIG. 5 is a side-view diagram of the hook shown in FIG. 4.
Figure 6:
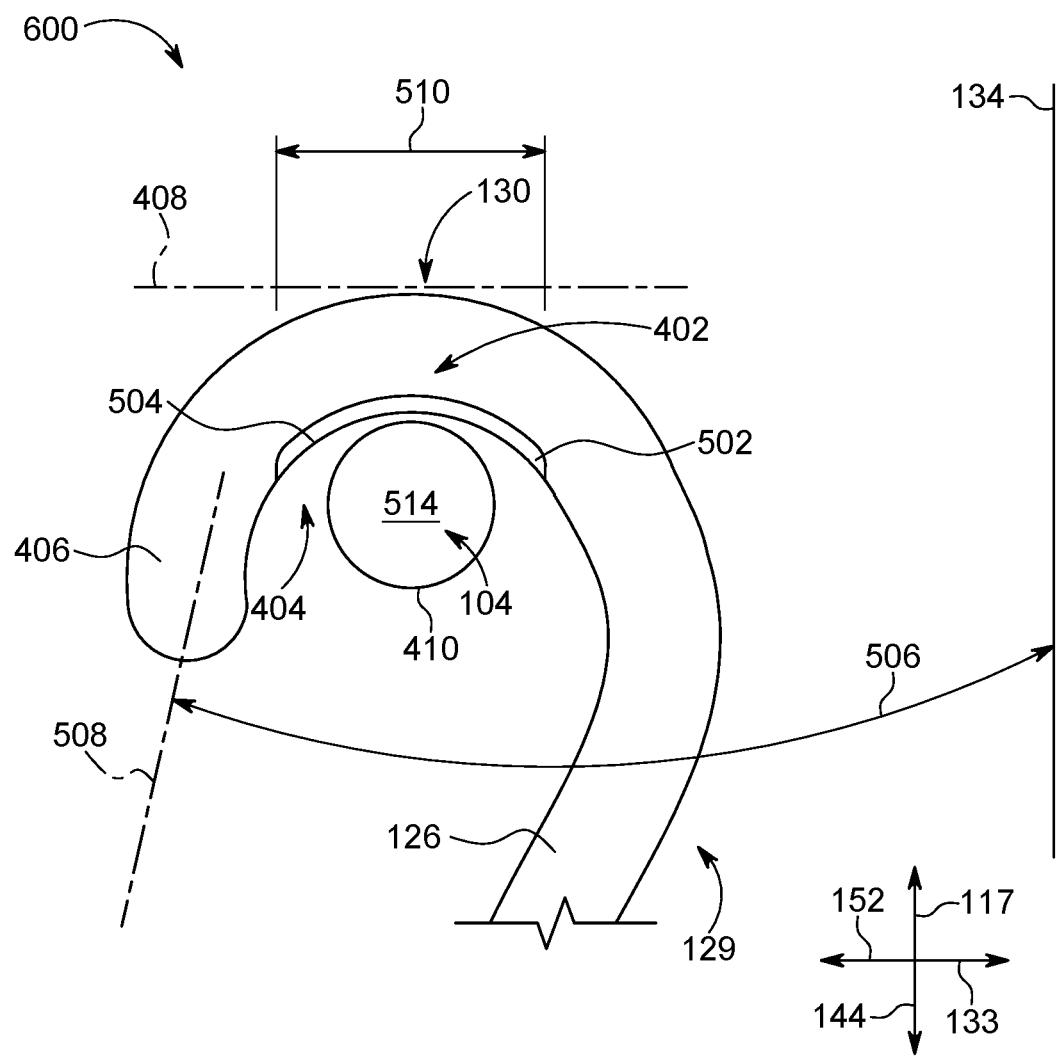
FIG. 6 is a side-view diagram of an alternative embodiment of the hook shown in FIGS. 4 and 5.

Also, in the embodiment shown in FIG. 4, the supportive structure 104 includes an elongate structure 410 positioned substantially parallel to a ground surface 412. For example, and without limitation, elongate structure 410 is embodied in a bath tissue roll holder rod 413 and ground surface 412 is embodied in a floor 415 in a home, business, or industrial structure. Referring now to FIGS. 5 and 6, for example and without limitation, elongate structure 410 has a width 512 that is less than or substantially equal to an effective slot width 510 of the slot 404.

Figure 7:
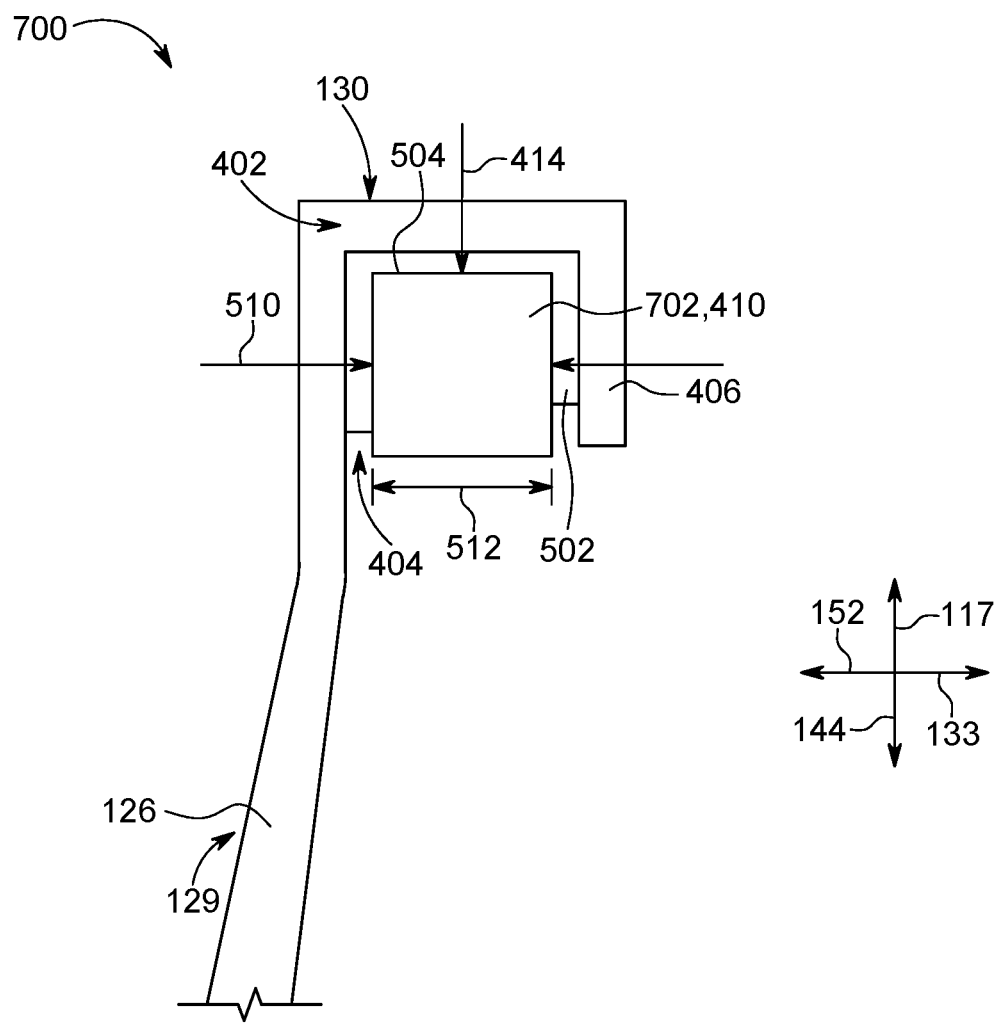
FIG. 7 is a side-view diagram of another embodiment of the hook shown in FIGS. 4 and 5.

Furthermore, as shown in FIGS. 5, 6, and 7, the elongate structure 410 includes at least one of a rod 514 having a circular cross-section, a rod having an elliptical cross-section, a bar 702 having a square cross-section, a bar having a rectangular cross-section, a bar having a triangular cross-section, and a bar having a polygon-shaped cross-section, the polygon having greater than four sides. Depending upon particular shapes of at least one of the supportive structure 104 and the elongate structure 410, the shape of the hook 402 is correspondingly formed to conform to the particular shape to facilitate a secure, yet removable attachment of device 400. Moreover, as shown in FIGS. 5 and 6, device 400 further includes a hook pad 502 coupled to a downward 144 facing surface of the hook 402. In other embodiments, not shown, device 400 does not include hook pad 502.

Further, in the embodiment shown in FIG. 4, at least a portion of the second section 129, the distal end 130, and the shank 406 define an arcuate hook 402 structure. The arcuate hook 402 structure is intended for user 150 to fit around upper 117 portion(s) of elongate structure(s) 410 (e.g., a rod) having at least one of a circular cross-section and an elliptical cross-section. In other embodiments (e.g., as shown and described below with reference to FIG. 7), hook 402 is not arcuately formed, but rather is formed with shank 406 having substantially square corners and in shape(s) intended for user 150 to fit around upper 117 portion(s) of elongate structure(s) 410 (e.g., a bar) having at least one of a square cross-section and a rectangular cross-section. In still other embodiments, not shown, hook 402 is formed with a triangularly and/or polygonally-shaped (greater than four sides) shaped shank 406 and in shape(s) intended for user 150 to fit around upper 117 portion(s) of elongate structure(s) 410 (e.g., a bar) having at least one of a triangular cross-section and a polygonal cross-section having greater than four sides.

Furthermore, in the embodiments shown in FIGS. 4 and 5 (e.g., a device 400 and device 500, respectively), shank 406 is positioned frontward 152 relative to the second section 129 in device 400. In other embodiments, such as is shown in FIG. 6 (e.g., a device 600), shank 406 has the opposite positioning, with shank 406 being positioned rearward 133 relative to the second section 129. Moreover, in the embodiment shown in FIG. 4, the supportive structure 104 also includes at least one offset structure 426 coupled to the substantially vertical surface 134 and extending frontward 152 therefrom. The elongate structure 410 is coupled to the at least one offset structure 426 to provide and facilitate a spacing of the elongate structure 410 from the substantially vertical surface 134 by a predetermined offset distance 432.

Moreover, in the embodiment illustrated in FIG. 4, the first section 128 includes an arm axis 437 and the container 106 includes a container axis 439. In this embodiment, the at least one hanger arm 126 is coupled to container 106 with arm axis 437 and container axis 439 oriented at a coupling angle 440 that is greater than zero degrees and less than about forty-five degrees. In other embodiments, such as device 100 shown and described above with reference to FIG. 1, coupling angle 440 (not shown in FIG. 1) is substantially equal to zero degrees (e.g., the at least one hanger arm 126 is straight, rather than arcuately curved). In still other embodiments, not shown, coupling angle 440 is greater than zero degrees and less than about ninety degrees.

Figure 8:
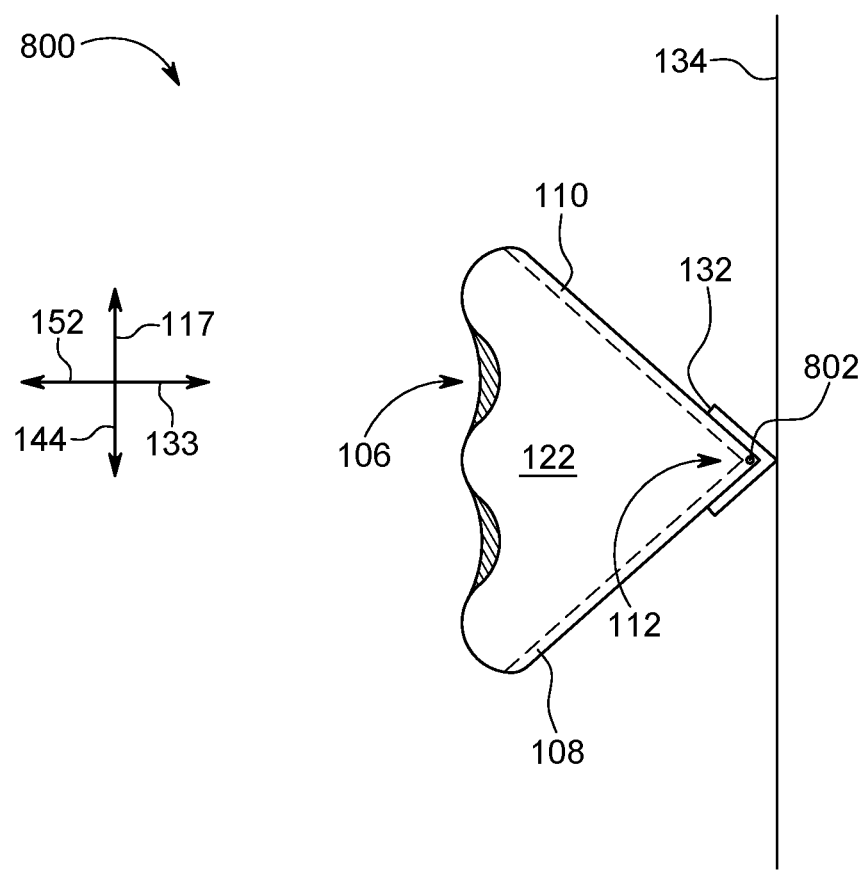
FIG. 8 is a side-view diagram of an alternative embodiment of a portion of the container shown in FIG. 4.

As shown in FIG. 4, a rearward 133 facing portion of container 106 includes an arcuate fillet 438. Arcuate fillet 438 is formed at a juncture of a rearward 133 facing portion of the base 108 and a rearward 133 facing portion of the at least one container side wall 110. The arcuate fillet 438 is thus concavely formed with respect to the interior cavity 122 of the container 106. In the embodiment shown in FIG. 4, device 400 further includes bumper 132 coupled to an exterior 120 rearward 133 facing surface of the arcuate fillet 438. In other embodiments (e.g., as shown in FIG. 8), the devices shown and described herein do not include the arcuate fillet 438. For example, in a device 800, a rearward 133 facing portion of container 106 includes a substantially square corner 802 formed at a juncture of a rearward 133 facing portion of the base 108 and a rearward 133 facing portion of the at least one container side wall 110. When hanging from the elongate structure 410, device 800, for example, further contacts the substantially vertical surface 134 at the square corner 802. Moreover, in device 800, square corner 802 includes a square corner bumper 132 coupled thereto, substantially as shown and described above with reference to bumper 132 coupled to arcuate fillet 438 (e.g., FIG. 4).

Device 400, and other embodiments of the devices described herein which include hook 402, hangs from elongate structure 410 through removable coupling of hook 402 to elongate structure 410 through the slot 404. Depending upon particular shapes of at least one of the supportive structure 104 and the elongate structure 410 (e.g., rod as compared to bar, as shown and described above), the shape of hook 402 is correspondingly formed to conform to the particular shape to facilitate a secure, yet removable attachment of device 400. Hook pad 502 is formed of a softer and generally more pliable material of construction than the rest of hook 402. For example, and without limitation, hook pad 502 protects elongate structure 410 (e.g., bath tissue holder rod 413 holding a bath tissue roll 460, where bath tissue holder rod 413 is inserted through a center cavity 462 of bath tissue roll 460) from wear due to repeated attachment and removal of device 400 to and from, respectively, elongate structure 410 by user 150. Also, for example, hook pad 502 mitigates undesired movements of the device (e.g., device 400) during use thereof (e.g., before, during, and/or after application of force 148 by user 150 to pump assembly 124 and/or prior to, during, and/or after user 150 removes a sheet 464 from bath tissue roll 460). Hook pad 502 further provide additional benefits in the various embodiments of the devices described herein, of which persons having ordinary skill in the art will recognize and appreciate.

When hanging from elongate structure 410, device 400 exerts upon elongate structure 410 a gravity force 414 having a downward 144 force vector component. In addition to the gravity force 414, when hanging from elongate structure 410, device 400 further exerts a lateral force 421 upon elongate structure 410. Lateral force 421 includes downward 144 and rearward 133 force vector components. The coupling of the hook 402 to the elongate structure 410 defines a fulcrum 422 of device 400, and the hanger arm 126 (e.g., the arcuate hanger arm 126 in device 400) generally defines a pivot arm 424 of device 400.

Also, in the embodiment shown in FIG. 4, the at least one offset structure 426 provides and facilitates device 400 (e.g., when hanging from elongate structure 410) having the ability to further exert a contact force 434 to at least one of a contact point 436 and a contact region 436 upon the substantially vertical surface 134. The removable attachment 428 of offset structure 426 to the substantially vertical surface 134 is sufficiently load-bearing to support device 400 hanging therefrom, including device 400 having container 106 with at one or more interior cavities 122 filled to capacity with liquid 102. The contact force 434 has at least one of rearward 133 force vector component and a downward 144 force vector component. The at least one hanger arm 126 extending distally (e.g., generally upward) from the container 106 facilitates providing a cancellation of torque when the user 150 applies force 148 on the pump assembly 124.

Furthermore, as shown in FIG. 4, when hanging from elongate structure 410, device 400 contacts the substantially vertical surface 134 at a rearward 133 facing portion of the container 106. In combination, gravity force 414 and lateral force 434 provide and facilitate device 400 having the ability to remain securely, yet removably attached to supportive structure 104 (e.g., elongate structure 410) including before, during, and after application of force 148 by user 150 to pump assembly 124. Inclusion of at least one of bumper 132 and hook pad 502 in devices described herein (e.g., device 400) further provides structural stability when the devices are hanging from elongate structure 410 and being manipulated by user 150. This structural stability is provided by, for example and without limitation, at least one of bumper 132 and hook pad 502 damping forces experienced during use and which have force vector components in at least one direction (e.g., at least one of frontward 152, rearward 133, upward 117, downward 144, leftward 230, and rightward 232).

Gravity force 414 and lateral force 434 further provide and facilitate device 400 having the ability to remain securely, yet removably attached to supportive structure 104 including before, during, and/or after user 150 operates pump assembly 124, manipulates container 106 (e.g., to fill it with liquid 102 and/or to check the remaining volume of liquid therein), handles bath tissue roll 406 to remove at least one sheet 464 therefrom, and/or manipulate various other features of the devices described herein (e.g., adjustable features, including, without limitation, those shown and described below with reference to FIGS. 9-12, and also, e.g., drawers, cavities, covers, and/or hooks including, without limitation, those shown and described below with reference to FIGS. 13-17). In other embodiments, not shown (e.g., embodiments not including at least one of bumper 132 and hook pad 502), user 150 affixes pads and other types of materials (e.g., materials that are softer and generally more pliable than the rest of container 106, hanger arm 126, and/or hook 402) to surface(s) of supportive structure 104 (e.g., elongate structure 410 and/or substantially vertical surface 134) where the devices described herein (e.g., device 400) are expected to make contact with supportive structure 104 during use. For example, and without limitation, user 150 couples at least one rubber pad (not shown) to substantially vertical surface 134 at the contact region 436 thereof.

Moreover, in the embodiment shown in FIG. 4, when device 400 is hanging from elongate structure 410, device 400 further contacts the substantially vertical surface 134 (e.g., at at least one of contact point 436 and contact region 436) at the arcuate fillet 438, including, without limitation, arcuate fillet 438 having bumper 132 coupled thereto. Arcuate fillet 438 provides and facilitates mitigation of wear to substantially vertical surface 134 on account of application of at least one of gravity force 414, and lateral force 434, and force 148. Inclusion of bumper 132 coupled to arcuate fillet 438 enhances the aforementioned wear-mitigative effect.

Figure 9:
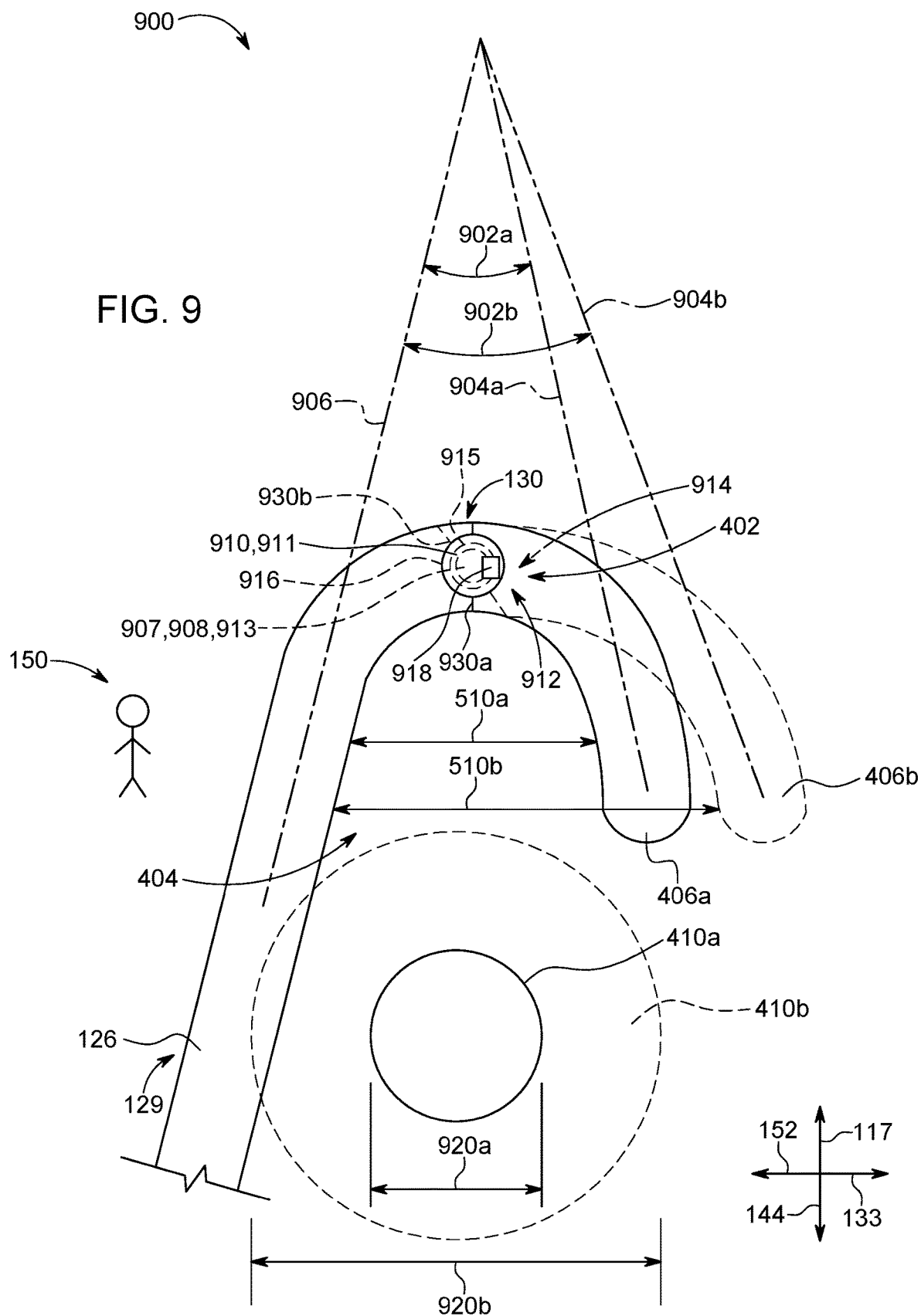
FIG. 9 is a side-view diagram of still another embodiment of the hook shown in FIGS. 4 and 5.

FIG. 9 is a side-view diagram of still another embodiment of the hook shown in FIGS. 4 and 5. In the embodiment shown in FIG. 9, a device 900 includes the shank 406 rotatably coupled to the second section 129 of the at least one hanger arm 126. The shank 406 is rotatably coupled to second section 129 proximate the distal end 130 of hanger arm 126.

Shank 406 includes a shank axis 904, and second section 129 includes a second section axis 906. A shank angle 902 is defined by an angle of shank axis 904 relative to second section axis 906. Shank angle 902 is selectively adjustable by user 150 of device 900 by rotating (e.g., pivoting) shank 406 about a shank pivot point 907. Selectively adjusting shank angle 902 through rotation of shank 406 about shank pivot point 907 thereby provides and facilitates alternate increasing and decreasing of shank angle 902 by user 150.

To provide and facilitate adjustment of shank angle 902 by user 150, device 900 includes a bore 908 defined through at least one of shank 406 and second section 129. Device 900 also includes a pivot pin 910 slidingly coupled to at least one of shank 406 and second section 129. Device 900 further includes a pivot pin 910 including a pin head 911 and a pin shaft 913. Pivot pin 910 is inserted through bore 908 from a first side 912 of distal end 130 toward a second side 914 of distal end. In other embodiments, not shown, pivot pin 910 is inserted through bore 908 from second side 914 toward first side 912. The pin shaft 913 has a width substantially equal to a width of bore 908. Pin head 911 has a width greater than the width of pin shaft 913 to prevent a complete travel of pin shaft 913 through bore 908. Device 900 also includes a flange 915 coupled to pin shaft 913 on one side thereof, for example and without limitation, proximate a surface of the second side 914. Flange 915 has a width that is greater than the width of bore 908.

Also, in device 900, shank angle 902 is securable in a substantially fixed position following adjustment of shank angle 902 by user 150. To secure shank 406 and to fix shank angle 902 at the value (e.g., position of shank 406) selected by user 150, device 900 includes a lock mechanism 918 coupled to at least one of pin head 911 and flange 915. Lock mechanism 918 provides and facilitates user 150 having the ability to selectively couple and decouple at least one of pin head 911 and flange 915 to and from at least one of first side 912 and second side 914. Moreover, adjustment of shank angle 902 provides and facilitates user 150 having the ability to selectively adjust the effective slot width 510 of the slot 404 of hook 402.

In the embodiment shown in FIG. 9, the supportive structure 104 includes elongate structure 410 positioned substantially parallel to ground surface 412, not shown. Elongate structure 410 has a width 920 that is less than or substantially equal to the effective slot width 510 of slot 404. Thus, device 900, like device 400, is hangable from elongate structure 410 through a removable coupling of hook 402 to elongate structure 410 through the slot 404. Lock mechanism 918, described above, provides and facilitates rotatable shank 406 having the ability to form a secure, but removable, load-bearing attachment of device 900 from elongate structure 410. Lock mechanism 918 thereby prevents detachment of device 900 from elongate structure 410 by reducing a probability of decoupling of hook 402 from elongate structure 410 (e.g., due to slippage and/or undesired rotation of shank 402 about shank pivot point 907). Furthermore, lock mechanism 918 provides and facilitates user 150 having the ability to accommodate, in a secured fashion, varying widths 920 of different elongate structures 410.

In other embodiments, not shown, shank 406 is not rotatable about a shank pivot point 907, but rather is formed of a flexible material of construction. In such other embodiments, shank angle 902 of shank axis 904 relative to second section axis 906 is selectively adjustable to facilitate alternately increasing and decreasing the shank angle 902 and the effective slot width 510. The flexible material of construction of shank 406 is flexible enough to be manually manipulated by user 150 in at least one direction (e.g., frontward 152, rearward 133, upward 117, downward 144, leftward 230, and rightward 232). Although the flexible material of construction of shank 406 in such other embodiments is manually manipulatable, it retains its shape and its load-bearing properties after being manipulated by user 150.

For example, and without limitation, user 150 of device 900 selectively adjusts the shank angle 902 by alternately flexing the shank 406 frontward 152 and rearward 133. Thus, the flexible material of construction of shank 406 provides and facilitates shank 406 having the ability to form a secure, but removable, load-bearing attachment of this embodiment of device 900 from elongate structure 410. Device 900 having the flexible material of construction of shank 406 (e.g., instead of, or in addition to rotatable shank 406 and/or lock mechanism 918) thereby prevents detachment of such device embodiments from elongate structure 410 by reducing a probability of decoupling of hook 402 from elongate structure 410 (e.g., due to slippage, breakage, and/or undesired changes in shape and/or load-bearing properties of shank 402).

Furthermore, the flexible material of construction of shank 406 provides and facilitates user 150 having the ability to accommodate, in a secured fashion, varying widths 920 of different elongate structures 410. Flexible material of construction of shank 406 also provides and facilitates user 150 having the ability to conform the shape of the hook 402 to varying shapes and widths 920 of different elongate structures 410. In other embodiments, not shown, at least one portion of the at least one hanger arm 126 other than or in addition to hook 402 is formed of the flexible material of construction to provide similar benefits to user 150 of the devices (e.g., device 900) described herein. For example, and without limitation, in such other embodiments, at least one of first section 128 and second section 129 is formed of the flexible material of construction to provide and facilitate the user 150 having the ability to selectively and alternately transition hanger arm 126 from a substantially straight and vertical hanger arm 126 (e.g., having an angle of arm axis 437 relative to second section axis 906 that is substantially equal to zero degrees, as shown in FIG. 1) to the arcuately curved hanger arm 126 (e.g., where an angle of arm axis 437 relative to second section axis is not substantially equal to zero degrees, as shown in FIG. 4).

In those embodiments (e.g., device 900) having shank angle 902 that is adjustable by user 150, pin head 911 has a width that is greater than the width of pin shaft 913 to prevent a complete travel of pin shaft 913 through bore 908. Also, in the embodiment shown in FIG. 9, flange 915 has a width that is greater than the width of bore 908 in order to facilitate preventing detachment of the pivot pin 910 from the bore 908 when inserted therein. Thus, for example, and without limitation, a first end of pin shaft 913 (e.g., opposite a second end thereof to which pin head 911 is coupled to) is inserted through bore 908 from first side 912, and when so inserted, pin head 911 rests upon first side 912. Flange 915 is then coupled to the first end of pin shaft 913 such that flange 915 is positioned proximate second side 914. In the embodiment shown in FIG. 9, both of flange 915 and pin head 911 are not further coupled to first side 912 and second side 914, respectively. In other embodiments, not shown, at least one of flange 915 and pin head 911 is further coupled to at least one of first side 912 and second side 914, respectively. Thus, in the example embodiment, shank 406 is rotatably coupled to the second section 129 of hanger arm 126 proximate the distal end 130 thereof. For example, and without limitation, flange 915 is coupled to both the first end of the pin shaft 913 and the second side 914, where the second side 914 is defined and positioned on the shank 906. The pin head 911 rests upon, but is not coupled to, the first side 912, where the first side 912 is defined and positioned on the second section 129 proximate the distal end 130 thereof. As shown in FIG. 9, shank 906 thus rotates about an axis defined by pin shaft 913 relative to distal end 130 of second section 129, and through a plurality of shank positions 930 (e.g., a first shank position 930*a* and a second shank position 930*b* that is different from the first shank position 930*a*).

Selective and alternating rotation (e.g., pivoting) of shank 906 by user 150 provides and facilitates user 150 having the ability to adjust (e.g., selectively and alternately increase and decrease) a shank angle 902 of a shank axis 904 relative to a second section axis 906, which thereby provides and facilitates user 150 having the ability to adjust (e.g., selectively and alternately increase and decrease) the shank angle 902 through a plurality of values (e.g., a first shank angle 902*a*, and a second shank angle 902*b* having a value that is greater than the first shank angle 902*a*). As user 150 adjusts shank angle 902 from the first shank angle value 902*a* to the second shank angle value 902*a*, the position of the shank axis 904 is likewise adjusted by user 150 from a first shank axis 904*a* position to a second shank axis 904*b* position. Similarly, as user 150 adjusts shank angle 902 from the first shank angle value 902*a* to the second shank angle value 902*a*, the position of shank 406 is adjusted by user 150 from a first shank 406*a* position to a second shank 406*b* position that is different from the first shank 406*a* position.

Device 900, like device 400, is hangable from elongate structure 410 through a removable coupling of hook 402 to elongate structure 410 through the slot 404. As described above, elongate structures 410 intended by user 150 for use with the devices described herein include various shapes and sizes (e.g., widths 920, and lengths). In an example use case, user 150 desires to transfer device 900 from a first elongate structure 410*a* having a first width 920*a* to a second elongate structure 410*b* having a second width 920*b* that is greater than the first width 920*a*. User 150 having the ability to adjust shank angle 902 (e.g., by alternately pivoting the shank 406 frontward 152 and rearward 133 relative to the position of distal end 130 of second section 129) further provides and facilitates him or her having the ability to accommodate, in a secured fashion, varying widths 920 of elongate structure 410. In the example use case, user 150 removes device 900 from first elongate structure 410*a*, and then adjusts shank angle 902 from the first shank angle 902*a* value (selected to accommodate the first width 920*a*) to the second shank angle 902*b* value (selected to accommodate the second width 920*b*). User 150 then hangs device 900 with shank angle 902 having the second shank angle 902*b* value from the second elongate structure 410*b* having the second width 920*b*. The selective and alternating adjustment of shank angle 902 through a plurality of values (e.g., first shank angle 902*a* value and second shank angle 902*b* value) further provides and facilitates the user 150 having the ability to adjust (e.g., selectively and alternately increase and decrease) the effective slot width 510 of the slot 404 of hook 402. In the example use case provided above, the first shank angle 902*a* corresponds to a first slot width 510*b* (accommodating the first width 920*a*) and the second shank angle 902*b* corresponds to a second slot width 510*b* (accommodating the second slot width 920*b*).

In the embodiment illustrated in FIG. 9, lock mechanism 918 included in device 900 provides and facilitates user 150 having the ability to selectively couple and decouple at least one of pin head 911 and flange 915 to and from at least one of first side 912 and second side 914, respectively, to further facilitate the selective and alternating increasing and decreasing of shank angle 902. In other embodiments, not shown (e.g., device embodiments where flange 915 is positioned proximate first side 912 and pin head 911 is positioned proximate second side 914), lock mechanism 918 provides and facilitates user 150 having the ability to selectively couple and decouple at least one of flange 915 and pin head 911 to and from at least one of first side 912 and second side 914, respectively, to further facilitate the selective and alternating increasing and decreasing of shank angle 902.

In one embodiment of the devices (e.g., device 900) described herein, lock mechanism 918 includes a peg (not shown) that is selectively and alternately inserted and removed into and out of a correspondingly and nestingly shaped peg receptacle (not shown) defined and formed in a surface of at least one of second side 914 of shank 906 and first side 912 of second section 129 proximate distal end 130. Thus, for example and without limitation, user 150 maintains the peg inserted into peg receptacle when he or she desires to maintain the otherwise rotatable shank 406 in a secured and fixed position (e.g., to prevent pivoting of shank 406 and to maintain shank angle 402 at a first predetermined shank angle 402*a* value). To adjust shank angle 402 from the first shank angle 402*a* value to the second shank angle 402*b* value (e.g., as described in the use case example provided above), user 150 removes (e.g., retracts) the peg from peg receptacle, thereby permitting the otherwise non-pivotable shank 406 to pivot about the shank pivot point 907 to the desired second shank angle 402*b* value. Upon reaching the second shank angle 402*b* value, user 150 inserts the peg back into the peg receptacle to secure and affix the otherwise rotatable shank 406 in the second shank 406*b* position (e.g., to again prevent pivoting of shank 406 and to maintain shank angle 402 at a second predetermined shank angle 402*b* value). During such times when device 900 is hanging from elongate structure 410, lock mechanism 918 prevents and/or reduces a probability of detachment (e.g., slippage) of device 900 (and, similarly, other embodiments of the devices described herein having the rotatable shank 406). Lock mechanism 918 further provides and facilitates user 150 having the ability to securely and conveniently accommodate varying widths 920 of different elongate structures 410, substantially as described above.

Figure 10:
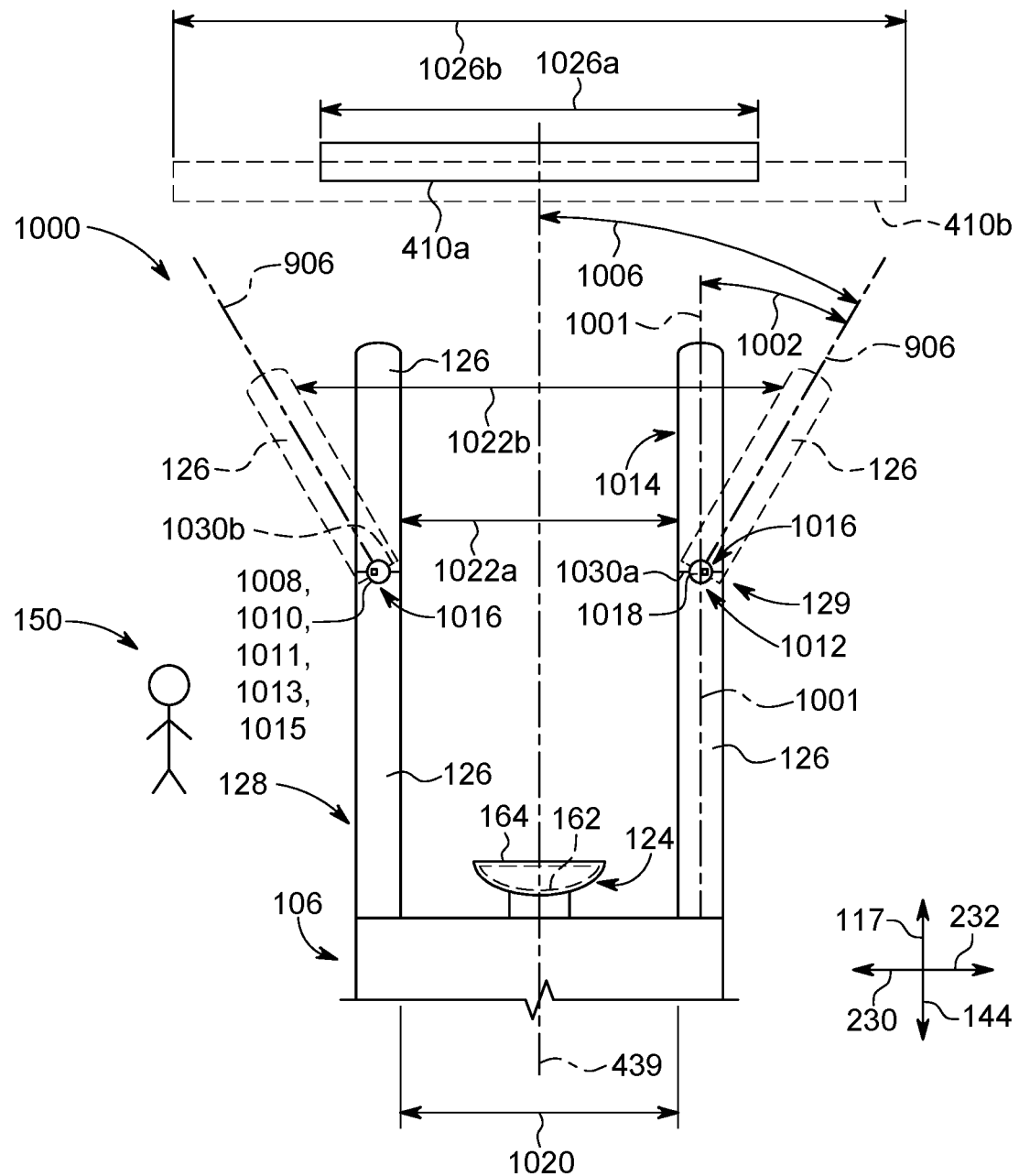
FIG. 10 is a front view diagram of an alternative embodiment of the hanger arms shown in FIG. 2.

FIG. 10 is a front view diagram of an alternative embodiment of the hanger arms 126 shown in FIG. 2. In the embodiment shown in FIG. 10, a device 1000 includes two hanger arms 126. The first sections 128 of the two hanger arms 126 are spaced apart by a first lateral distance 1020, and the second sections 129 of the two hanger arms 126 are spaced apart by a second lateral distance 1022. The first section 128 and the second section 129 of each hanger arm 126 of the two hanger arms 126 are rotatably coupled together at a first arm section pivot point 1016. First section 128 includes a first section axis 1001, and second section 129 includes second section axis 906. A first angle 1002 is defined by an angle of second section axis 906 relative to first section axis 1001. First angle 1002 is selectively adjustable by user 150 of device 1000 by rotating (e.g., pivoting) second section 129 about the first arm section pivot point 1016. Selectively adjusting first angle 1002 through rotation of second section 129 about the first arm section pivot point 1016 thereby provides and facilitates alternate increasing and decreasing of first angle 1002 by user 150.

Also, in the embodiment shown in FIG. 10, container 106 includes a container axis 439. A second angle 1006 is defined by an angle of second section axis 906 relative to container axis 439. Second angle 1006 is selectively adjustable by user 150 of device 1000 by rotating (e.g., pivoting) second section 129 about the first arm section pivot point 1016. Selectively adjusting second angle 1006 through rotation of second section 129 about the first arm section pivot point 1016 thereby provides and facilitates alternate increasing and decreasing of second angle 1006 by user 150.

To provide and facilitate adjustment of first angle 1002 and second angle 1006 by user 150, device 1000 includes a bore 1008 defined through at least one of the first section 128 and the second section 129. Device 1000 also includes a pivot pin 1010 slidingly coupled to at least one of the first section 128 and the second section 129. Pivot pin 1010 includes a pin head 1011 and a pin shaft 1013. Pivot pin 1010 is inserted through bore 1008 from a first side 1012 of each hanger arm 126 of the two hanger arms 126 toward a second side 1014 of each hanger arm 126 of the two hanger arms 126. In other embodiments, not shown, pivot pin 1010 is inserted through bore 1008 from second side 1014 toward first side 1012. The pin shaft 1013 has a width substantially equal to a width of bore 1008. Pin head 1011 has a width greater than the width of pin shaft 1013 to prevent a complete travel of pin shaft 1013 through bore 1008. Device 1000 also includes a flange 1015 coupled to pin shaft 1013 on one side thereof, for example and without limitation, proximate a surface of the second side 1014. Flange 1015 has a width that is greater than the width of bore 1008.

Also, in device 1000, first angle 1002 and second angle 1006 are securable in a substantially fixed position following adjustment of first angle 1002 and second angle 1006 by user 150. To secure second section 129 and to fix first angle 1002 and second angle 1006 at the value (e.g., position of second section 129) selected by user 150, device 1000 includes a locking mechanism 1018 coupled to at least one of pin head 1011 and flange 1015. Locking mechanism 1018 provides and facilitates user 150 having the ability to selectively couple and decouple at least one of pin head 1011 and flange 1015 to and from at least one of first side 1012 and second side 1014, respectively. Moreover, adjustment of first angle 1002 and second angle 1006 provides and facilitates user 150 having the ability to selectively adjust (e.g., alternately increase and decrease) the second lateral distance 1022.

In the embodiment shown in FIG. 10, the supportive structure 104 includes elongate structure 410 positioned substantially parallel to ground surface 412, not shown. Elongate structure 410 has a length 1026 that is greater than or substantially equal to the second lateral distance 1022. Thus, device 1000, like device 400 and device 900, is hangable from elongate structure 410 through a removable coupling of at least one of first section 128 and second section 128 (e.g., using hook 402) to elongate structure 410. Locking mechanism 1018, described above, provides and facilitates rotatable second section 129 having the ability to form a secure, but removable, load-bearing attachment of device 1000 from elongate structure 410. Locking mechanism 918 thereby prevents detachment of device 1000 from elongate structure 410 by reducing a probability of at least one of decoupling of device 1000 from elongate structure 410, undesired change of position of device 1000 when hanging from elongate structure 410, and uneven downward 144 forces exerted by a weight of device 1000 through a first hanger arm 126 as compared to a second hanger arm 126 (e.g., due to slippage and/or undesired rotation of second section 129 about first arm section pivot point 1016). Furthermore, locking mechanism 1018 provides and facilitates user 150 having the ability to securely and conveniently accommodate varying lengths 1026 of different elongate structures 410.

In other embodiments, not shown, second section 129 of each hanger arm 126 of the two hanger arms 126 includes at least one fastener hole 138, substantially as shown and described above with reference to FIG. 1. In such other embodiments, devices not having hooks 402 are alternately attachable to and removable from supportive structure 104, including, without limitation, substantially vertical surface 134, substantially as shown and described above with reference to FIG. 1. User 150 having the ability to selectively adjust the second lateral distance 1022 provides him or her benefits including, without limitation, conforming second lateral distance 1022 to locations of studs in wall(s) to which the disclosed devices and systems are desired to be attached to.

In still other embodiments, not shown, second section 129 is not rotatable about a first arm section pivot point 1016. Rather, at least a portion of the at least one hanger arm 126 is formed of a flexible material of construction. In such other embodiments, first angle 1002 and second angle 1006 are selectively adjustable to facilitate alternately increasing and decreasing the first angle 1002 and second angle 1006, and the second lateral distance 1022. The flexible material of construction of the at least a portion of the at least one hanger arm 126 is flexible enough to be manually manipulated by user 150 in at least one direction (e.g., frontward 152, rearward 133, upward 117, downward 144, leftward 230, and rightward 232). Although the flexible material of construction of the at least a portion of the at least one hanger arm 126 in such other embodiments is manually manipulatable, it retains its shape and its load-bearing properties after being manipulated by user 150. For example, and without limitation, user 150 of device 1000 selectively adjusts the first angle 1002 and second angle 1006 by alternately flexing the second section 129 leftward 230 and rightward 232. Thus, the flexible material of construction of the at least a portion of the at least one hanger arm 126 provides and facilitates the at least one hanger arm 126 having the ability to form a secure, but removable, load-bearing attachment of this embodiment of device 1000 from elongate structure 410.

Device 1000 having the flexible material of construction of the at least a portion of the at least one hanger arm 126 (e.g., instead of, or in addition to rotatable second section 129 and/or lock mechanism 1018) thereby prevents detachment of such device embodiments from elongate structure 410 by reducing a probability of decoupling of the device (e.g., at hook 402) from elongate structure 410 (e.g., due to slippage, breakage, and/or undesired changes in shape and/or load-bearing properties of hanger arm 126). Furthermore, the flexible material of construction of the at least a portion of the at least one hanger arm 126 provides and facilitates user 150 having the ability to securely and conveniently accommodate varying lengths 1026 of different elongate structures 410.

In those embodiments (e.g., device 1000) having second angle 1006 that is adjustable by user 150, pin head 1011 has a width that is greater than the width of pin shaft 1013 to prevent a complete travel of pin shaft 1013 through bore 1008. Also, in the embodiment shown in FIG. 10, flange 1015 has a width that is greater than the width of bore 1008 in order to facilitate preventing detachment of the pivot pin 1010 from the bore 1008 when inserted therein. Thus, for example, and without limitation, a first end of pin shaft 1013 (e.g., opposite a second end thereof to which pin head 1011 is coupled to) is inserted through bore 1008 from first side 1012, and when so inserted, pin head 1011 rests upon first side 1012. Flange 1015 is then coupled to the first end of pin shaft 1013 such that flange 1015 is positioned proximate second side 1014. In the embodiment shown in FIG. 10, both of flange 1015 and pin head 1011 are not further coupled to first side 1012 and second side 1014, respectively. In other embodiments, not shown, at least one of flange 1015 and pin head 1011 is further coupled to at least one of first side 1012 and second side 1014, respectively. Thus, in the example embodiment, the first section 128 and the second section 129 of each hanger arm 126 of the two hanger arms 126 are rotatably coupled together at a first arm section pivot point 1016. For example, and without limitation, flange 1015 is coupled to both the first end of the pin shaft 1013 and the second side 1014, where the second side 1014 is defined and positioned on the second section 129. The pin head 1011 rests upon, but is not coupled to, the first side 1012, where the first side 1012 is defined and positioned on an end of the first section 128 distal the container 106. As shown in FIG. 10, second section 129 thus rotates about an axis defined by pin shaft 1013 relative to the first section axis 1001, and through a plurality of second section positions 1030 (e.g., a first second section position 1030a and a second second section position 1030b that is different from the first second section position 1030a).

Selective and alternating rotation (e.g., pivoting) of second section 129 by user 150 provides and facilitates user 150 having the ability to adjust (e.g., selectively and alternately increase and decrease) a second angle 1006 of a second section axis 906 relative to a container axis 439, which thereby provides and facilitates user 150 having the ability to adjust (e.g., selectively and alternately increase and decrease) the second angle 1006 through a plurality of values (e.g., a first second angle 1006 value that is substantially equal to zero degrees, and a second second angle 1006 value having a value that is not equal to zero degrees). As user 150 adjusts second angle 1006 from the first second angle value 1006 to the second second angle value 1006, the position of the second section 129 is likewise adjusted by user 150 from a first second section position 1030a to a second second section position 1030b. Similarly, as user 150 adjusts second angle 1006 from the first second angle value 1006 to the second second angle value 1006, a value of first angle 1002 is adjusted by user 150 from a first first angle 1002 value (e.g., substantially equal to zero) to a second first angle 1002 value (e.g., not equal to zero degrees).

Device 1000 is removably attached to supportive structure 104 (e.g., hangable from elongate structure 410 through a removable coupling of hook(s) 402 to elongate structure 410 through slot(s) 404). As described above, elongate structures 410 intended by user 150 for use with the devices described herein include various shapes and sizes (e.g., widths 920, and lengths 1026). In an example use case, user 150 desires to transfer device 900 from a first elongate structure 410a having a first length 1026a to a second elongate structure 410b having a second length 1026b that is greater than the first length 1026a. User 150 having the ability to adjust second angle 1006 (e.g., by alternately pivoting the second section 129 leftward 230 and rightward 232 relative to the container axis 439) further provides and facilitates him or her having the ability to securely and conveniently accommodate varying lengths 1026 of elongate structure 410. In the example use case, user 150 removes device 1000 from first elongate structure 410a, and then adjusts second angle 1006 from the first second angle 1006 value (selected to accommodate the first length 1026a) to the second second angle 1006 value (selected to accommodate the second length 1026b). User 150 then hangs device 1000 with second angle 1006 having the second second angle 1006 value from the second elongate structure 410b having the second length 1026b. The selective and alternating adjustment of second angle 1006 through a plurality of values (e.g., first second angle 1006 value and second second angle 1006 value) further provides and facilitates the user 150 having the ability to adjust (e.g., selectively and alternately increase and decrease) the effective second lateral distance 1022. In the example use case provided above, the first second angle 1006 corresponds to a first second lateral distance 1022a (accommodating the first length 1026a) and the second second angle 1006 corresponds to a second second lateral distance 1022b (accommodating the second length 1026b).

Locking mechanism 1018 included in device 1000 provides and facilitates user 150 having the ability to selectively couple and decouple at least one of pin head 1011 and flange 1015 to and from at least one of first side 1012 and second side 1014, respectively, to further facilitate the selective and alternating increasing and decreasing of second angle 1006. In other embodiments, not shown (e.g., device embodiments where flange 1015 is positioned proximate first side 1012 and pin head 1011 is positioned proximate second side 1014), locking mechanism 1018 provides and facilitates user 150 having the ability to selectively couple and decouple at least one of flange 1015 and pin head 1011 to and from at least one of first side 1012 and second side 1014, respectively, to further facilitate the selective and alternating increasing and decreasing of second angle 1006.

In one embodiment of the devices (e.g., device 1000) described herein, locking mechanism 1018 includes a peg (not shown) that is selectively and alternately inserted and removed into and out of a correspondingly and nestingly shaped peg receptacle (not shown) defined and formed in a surface of at least one of second side 1014 of second section 129 and first side 1012 of first section 128 at the end thereof that is distal container 106. Thus, for example and without limitation, user 150 maintains the peg inserted into peg receptacle when he or she desires to maintain the otherwise rotatable second section 129 in a secured and fixed position (e.g., to prevent pivoting of second section 129 and to maintain second angle 1006 at a desired second angle 1006 value). To adjust second angle 1006 from the first second angle 1006 value to the second second angle 1006 value (e.g., as described in the use case example provided above), user 150 removes (e.g., retracts) the peg from peg receptacle, thereby permitting the otherwise non-pivotable second section 129 to pivot about the first arm section pivot point 1016 to the desired second second angle 1006 value. Upon reaching the second second angle 1006 value, user 150 inserts the peg back into the peg receptacle to secure and affix the otherwise rotatable second section 129 in the second second section position 1030*b* (e.g., to again prevent pivoting of second section 129 and to maintain second angle 1006 at a second predetermined second angle 1006 value). During such times when device 1000 is hanging from elongate structure 410, locking mechanism 1018 prevents and/or reduces a probability of detachment (e.g., slippage) of device 1000 (and, similarly, other embodiments of the devices described herein having the rotatable second section 129). Locking mechanism 1018 further provides and facilitates user 150 having the ability to securely and conveniently accommodate varying lengths 1026 of different elongate structures 410, substantially as described above.

Figure 11:
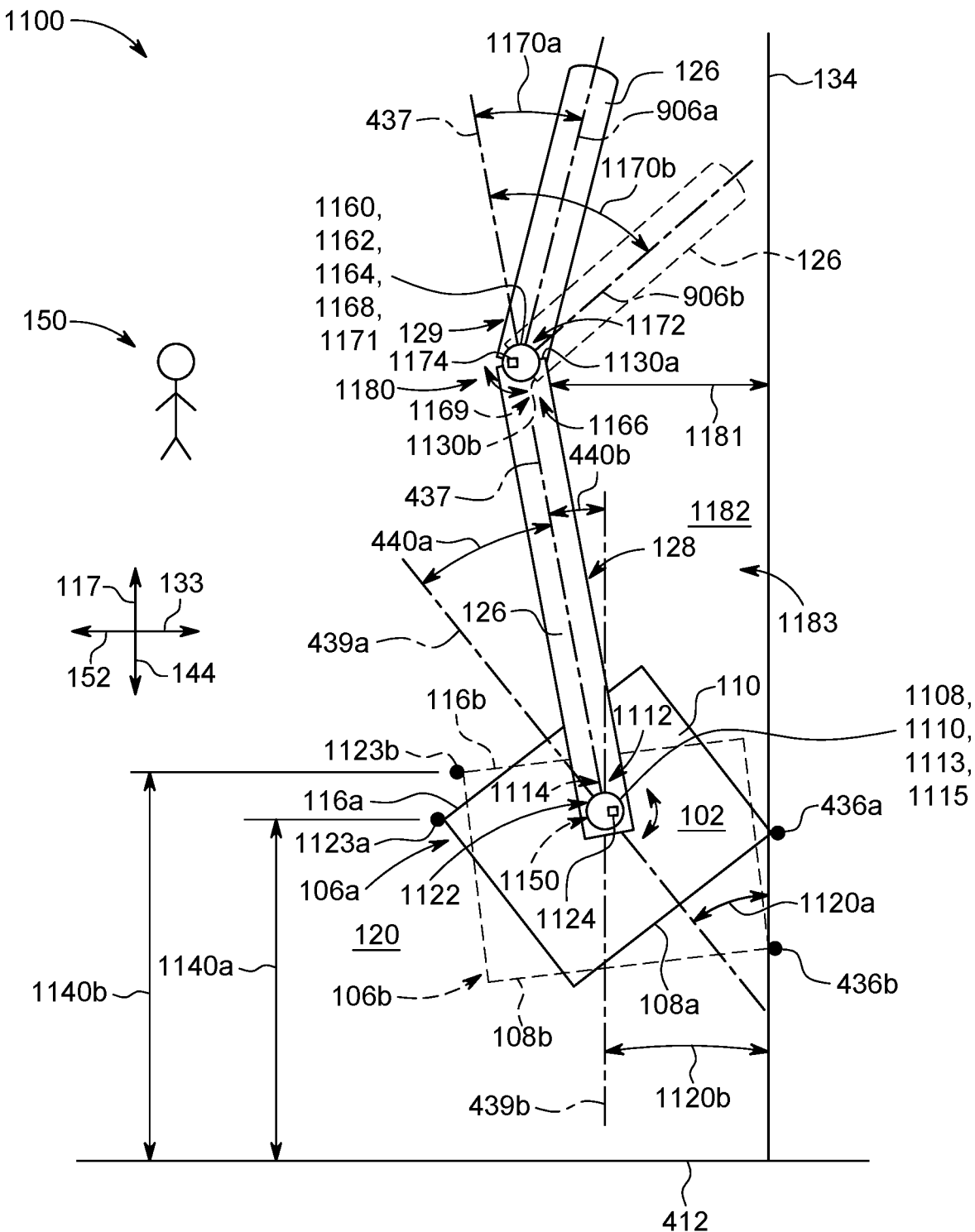
FIG. 11 is a side-view diagram of an alternative embodiment of the device shown in FIG. 4.

FIG. 11 is a side-view diagram of an alternative embodiment of the device shown in FIG. 4. In the embodiment shown in FIG. 11, a device 1100 includes the at least one hanger arm 126 coupled to the container 106. In device 1100, hanger arm 126 is further rotatably coupled to the container 106 at a coupling pivot point 1122. First section 128 of hanger arm 126 includes arm axis 437, and container 106 includes container axis 439. A coupling angle 440 of arm axis 437 relative to container axis 439 is selectively adjustable by user 150 of device 1100. Coupling angle 440, in the embodiment shown in FIG. 11, is adjustable by user 150 through at least one full rotation (e.g., greater than or equal to 360 degrees) of container 106 about coupling pivot point 1122. In other embodiments, not shown, coupling angle 440 is adjustable by user 150 through a range of rotational motion that is less than one full rotation of container 106 about coupling pivot point 1122. Further, in the embodiment shown in FIG. 11, container 106 is rotatable about coupling pivot point 1122 in both clockwise and counterclockwise directions to thereby enable and facilitate user 150 to alternately increase and decreasing coupling angle 440. In other embodiments, not shown, container 106 is rotatable by user 150 in one of clockwise and counterclockwise directions.

Also, in the embodiment shown in FIG. 11, when device 1100 is attached to the supportive structure 104, a rearward 133 facing portion of container 106 contacts the substantially vertical surface 134 at at least one of a contact point 436 and a contact region 436. In consequence of this contact, a contact angle 1120 is formed and defined between container axis 439 and the substantially vertical surface 134. Container 106 being rotatable about coupling pivot point 1122, as described above, thereby provides and facilitates user 150 having the ability to alternately increase and decrease the contact angle 1120. Furthermore, when device 110 is attached to the supportive structure 104 (not shown), a point 1123 on container top 116 is positioned above ground surface 412 by a height 1140 (e.g., measured in centimeters). The selective adjustment of the contact angle 1120 as described above further provides and facilitates user 150 having the ability to selectively increase and decrease the height 1140.

To provide and facilitate adjustment of at least one of the coupling angle 440 and the contact angle 1120 by user 150, device 1100 includes a first bore 1108 defined through at least one of the first section 128 and at least a portion of the container 106. Device 1000 also includes a first pivot pin 1110 slidingly coupled to at least one of the first section 128 and the at least a portion of the container 106. First pivot pin 1110 includes a first pin head 1111 and a first pin shaft 1113. First pivot pin 1110 is inserted through first bore 1108 from a first side 1112 of the first section 128 toward a second side 1114 of first section 128. In other embodiments, not shown, first pivot pin 1110 is inserted through first bore 1108 from second side 1114 toward first side 1112. The first pin shaft 1113 has a width substantially equal to a width of first bore 1108. First pin head 1111 has a width greater than the width of first pin shaft 1113 to prevent a complete travel of first pin shaft 1113 through first bore 1108. Device 1100 also includes a first flange 1115 coupled to first pin shaft 1113 on one side thereof, for example and without limitation, proximate a surface of the second side 1114 coupled to container 106. First flange 1115 has a width that is greater than the width of first bore 1108.

Also, in device 1100, at least one of coupling angle 440 and contact angle 1120 are securable in a substantially fixed position following adjustment of at least one of coupling angle 440 and contact angle 1120 by user 150. To secure first section 128 to container 106, and to fix at least one of coupling angle 440 and contact angle 1120 at the value (e.g., position of first section 128) selected by user 150, device 1100 includes a coupling lock 1124 coupled to at least one of first pin head 1111 and first flange 1115. Coupling lock 1124 provides and facilitates user 150 having the ability to selectively couple and decouple at least one of first pin head 1111 and first flange 1115 to and from at least one of first side 1112 and second side 1114, respectively. Moreover, adjustment of at least one of coupling angle 440 and contact angle 1120 provides and facilitates user 150 having the ability to selectively adjust (e.g., alternately increase and decrease) at least one of coupling angle 440 and contact angle 1120.

Further, in device 1100, first bore 1108 is further defined through the at least one container side wall 110. This embodiment of device 1100 further includes a seal 1150 positioned between first pin shaft 1113 and the at least one container side wall 110. Seal 1150 is further positioned proximate first flange 1115. In other embodiments, not shown, device 1100 does not include seal 1150 and first bore 1108 is not defined entirely through the at least one container side wall 110 (e.g., first bore 1108 does not extend through the entirety of container side wall 110).

In still other embodiments, not shown, container 106 and first section 128 are not rotatable relative to one another about coupling pivot point 1122. Rather, at least a portion of the at least one hanger arm 126 including, without limitation, at least a portion of first section 128, is formed of the flexible material of construction. In such other embodiments, at least one of coupling angle 440 and contact angle 1120 are selectively adjustable to facilitate alternately increasing and decreasing at least one of coupling angle 440 and the contact angle 1120. The flexible material of construction of the at least a portion of the at least one hanger arm 126 is flexible enough to be manually manipulated by user 150 in at least one direction (e.g., frontward 152, rearward 133, upward 117, downward 144, leftward 230, and rightward 232).

Although the flexible material of construction of the at least a portion of the at least one hanger arm 126 in such other embodiments is manually manipulatable, it retains its shape and its load-bearing properties after being manipulated by user 150. For example, and without limitation, user 150 of device 1100 selectively adjusts at least one of the coupling angle 440 and the contact angle 1120 by alternately flexing the first section 128 frontward 152 and rearward 133. Thus, the flexible material of construction of the at least a portion of the at least one hanger arm 126 provides and facilitates the at least one hanger arm 126 having the ability to form a secure, but adjustable, load-bearing attachment of this embodiment of device 1100 from supportive structure 104. Device 1100 having the flexible material of construction of the at least a portion of the at least one hanger arm 126 (e.g., instead of, or in addition to coupling pivot point 1122 and/or coupling lock 1124) thereby prevents detachment of container 106 from hanger arm 126 in such device embodiments.

In still further embodiments, not shown, at least a portion of second section 129 is formed of a flexible material of construction. In such other embodiments, the flexible material of construction of the at least a portion of the second section 129 provides and facilitates user 150 having the ability to manually manipulate second section 129 in at least one direction (e.g., frontward 152, rearward 133, upward 117, downward 144, leftward 230, and rightward 232). At least a portion of the second section 129 formed of the flexible material of construction further provides and facilitates user 150 having the ability to selectively adjust (e.g., alternately increase and decrease) a third angle 1170 of a second section axis 906 of second section 129 relative to arm axis 437. For example, and without limitation, by alternately flexing the at least a portion of the second section 129 frontward 152 and rearward 133, user 150 alternately decreases and increases third angle 1170.

Furthermore, in the embodiment shown in FIG. 11, when device 1100 is attached to supportive structure 104 (e.g., substantially vertical surface 134), the at least one hanger arm 126 is spaced from vertical surface 134 (e.g., wall) by an arm-to-vertical surface distance 1181. For example, and without limitation, the at least one hanger arm 126 further includes a midsection 1180 positioned between the distal end 130 (not shown) and the container 106. The midsection 1180 defines an approximate boundary between first section 128 and second section 129. Midsection 1180 is further positioned approximately equidistant between distal end 130 and container 106. In other embodiments, not shown, midsection 1180 is positioned closer to distal end 130 than to container 106. In still other embodiments, not shown, midsection 1180 is positioned nearer to container 106 than to distal end 130. Further, in those embodiments, not shown, including the at least a portion of the at least one hanger arm 126 formed of the flexible material of construction, the flexible material of construction further provides and facilitates user 150 having the ability to selectively adjust (e.g., alternately increase and decrease) the arm-to-vertical surface distance 1181 by the alternate flexing manipulations by user 150, as described above.

Also, when device 1100 is attached to the supportive structure 104 (e.g., substantially vertical surface 134), a first plane 1183 is approximately defined between the container 106, the at least one hanger arm 126, and the supportive structure 104 (e.g., the substantially vertical surface 134). The first plane 1183 has an area 1182. In those embodiments, not shown, including the at least a portion of the at least one hanger arm 126 formed of the flexible material of construction, the flexible material of construction further provides and facilitates user 150 having the ability to selectively adjust (e.g., alternately increase and decrease) the area 1182 by the alternate flexing manipulations by user 150, as described above.

Moreover, in the embodiment shown in FIG. 11, first section 128 and second section 129 are rotatably coupled together at a second arm section pivot point 1172. Third angle 1170, in the embodiment shown in FIG. 11, is adjustable by user 150 through at least one full rotation (e.g., greater than or equal to 360 degrees) of second section 129 about second arm pivot point 1172. In other embodiments, not shown, third angle 1170 is adjustable by user 150 through a range of rotational motion that is less than one full rotation of container 106 about second arm pivot point 1172. Further, in the embodiment shown in FIG. 11, second section 129 is rotatable about coupling pivot point 1122 in both clockwise and counterclockwise directions to thereby enable and facilitate user 150 to alternately increase and decreasing third angle 1170. In other embodiments, not shown, second section 129 is rotatable by user 150 in one of clockwise and counterclockwise directions. By manipulating at least one of the first section 128 and the second section 129 (e.g., by pivoting one of them relative to the other about second arm pivot point 1172), user 150 of device 1100 selectively adjusts (e.g., alternately increases and decreases) third angle 1170 of second section axis 906 relative to arm axis 437 to facilitate alternately increasing and decreasing the third angle 1170. When device 1100 is attached to supportive structure 104 (e.g., vertical surface 134), the selective adjustment of the third angle 1170 further provides and facilitates the user 150 having the ability to alternately increase and decrease the arm-to-vertical surface distance 1181, and thereby alternately increase and decrease the area 1182 of the first plane 1183. Likewise, when device 1100 is attached to supportive structure 104 (e.g., vertical surface 134), the selective adjustment of the third angle 1170 further provides and facilitates the user 150 having the ability to alternately increase and decrease the height 1140 and the contact angle 1120, substantially as described above with reference to pivoting the container 106 about the coupling pivot point 1122.

To provide and facilitate adjustment of at least one of the third angle 1170 by user 150, device 1100 includes a second bore 1160 defined through at least one of the first section 128 and the second section 129. Device 1100 also includes a second pivot pin 1162 slidingly coupled to at least one of the first section 128 and the second section 129. Second pivot pin 1162 includes a second pin head 1164 and a second pin shaft 1168. Second pivot pin 1162 is inserted through second bore 1160 from a first side 1166 of the at least one hanger arm 126 toward a second side 1169 of the at least one hanger arm 126. In other embodiments, not shown, second pivot pin 1162 is inserted through second bore 1160 from second side 1169 toward first side 1166. The second pin shaft 1168 has a width substantially equal to a width of second bore 1160. Second pin head 1164 has a width greater than the width of second pin shaft 1168 to prevent a complete travel of second pin shaft 1168 through second bore 1160. Device 1100 also includes a second flange 1171 coupled to second pin shaft 1168 on one side thereof, for example and without limitation, proximate a surface of the second side 1169. Second flange 1171 has a width that is greater than the width of second bore 1160.

Also, in device 1100, third angle 1170 is securable in a substantially fixed position following adjustment of the third angle 1170 by user 150. For example, and without limitation, to secure first section 128 to second section 129, and to fix third angle 1170 at the value (e.g., position of second section 129 relative to first section 128) selected by user 150, device 1100 includes an arm lock mechanism 1174 coupled to at least one of second pin head 1164 and second flange 1171. Arm lock mechanism 1174 provides and facilitates user 150 having the ability to selectively couple and decouple at least one of second pin head 1164 and second flange 1171 to and from at least one of first side 1166 and second side 1169, respectively. Moreover, adjustment of third angle 1170 provides and facilitates user 150 having the ability to selectively adjust (e.g., alternately increase and decrease) third angle 1170. When device 1100 is attached to the supportive structure 104 (e.g., substantially vertical surface 134), arm lock mechanism 1174 further provides and facilitates the user 150 having the ability to selectively adjust (e.g., alternately increase and decrease) the arm-to-vertical distance 1181 and thereby the area 1182 of the first plane 1183.

Figure 20:
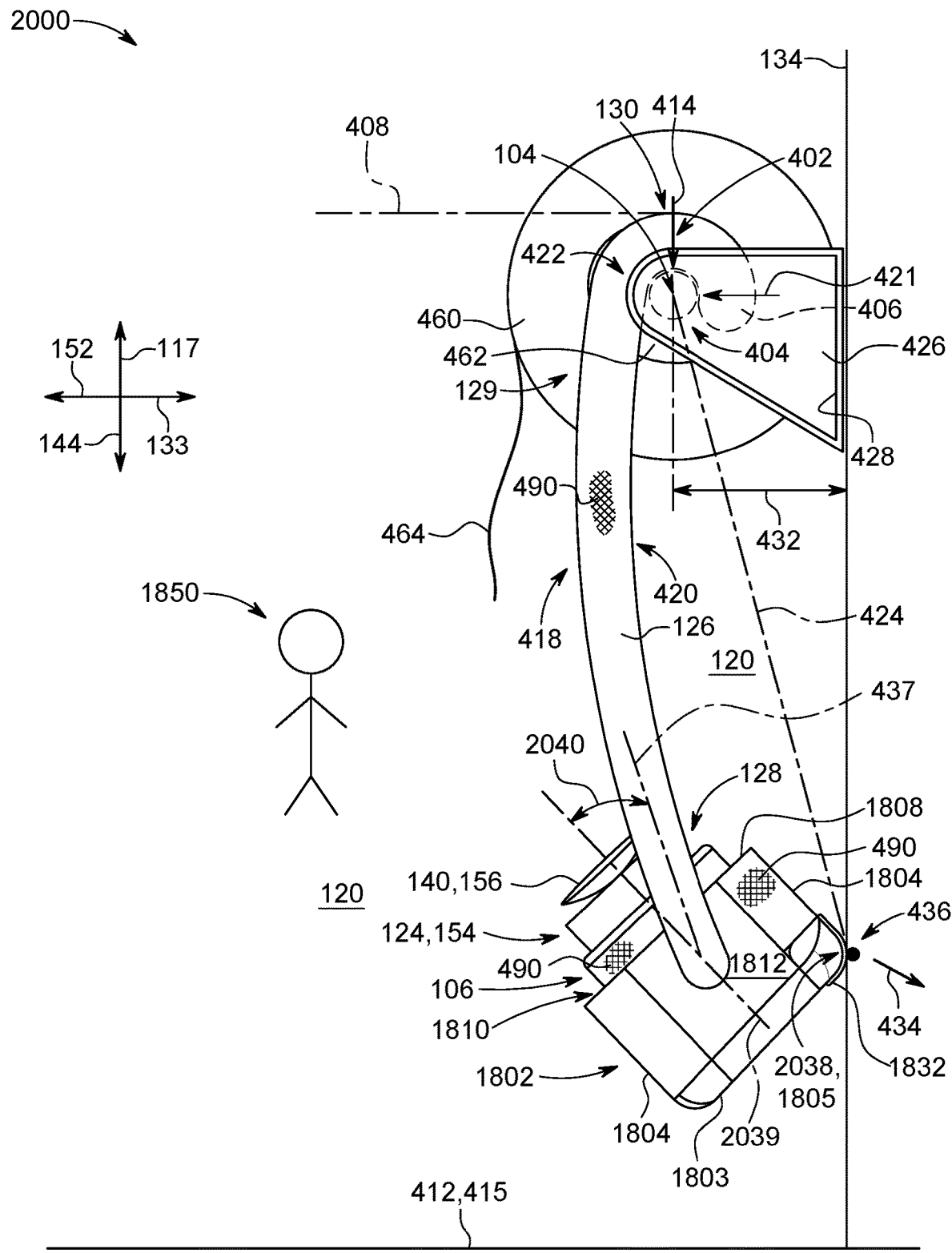
FIG. 20 is a side-view diagram of another embodiment of a system for containing and dispensing a liquid.

Furthermore, the flexible material of construction of the at least a portion of the first section 128 provides and facilitates user 150 having the ability to selectively and alternately adjust at least one of the coupling angle 440, the contact angle 1120, the area 1182, the height 1140, and the arm-to-vertical surface distance 1181. In other embodiments, not shown, at least one portion of the at least one hanger arm 126 other than or in addition to the at least a portion of the first section 128 is formed of the flexible material of construction to provide similar benefits to user 150 of the devices (e.g., device 1100) described herein. For example, and without limitation, in such other embodiments, at least one of first section 128 and second section 129 is formed of the flexible material of construction to provide and facilitate the user 150 having the ability to selectively and alternately transition hanger arm 126 from a substantially straight and vertical hanger arm 126 (e.g., having an angle of arm axis 437 relative to second section axis 906 that is substantially equal to zero degrees, as shown in FIG. 1) to the arcuately curved hanger arm 126 (e.g., where an angle of arm axis 437 relative to second section axis is not substantially equal to zero degrees, as shown in FIG. 20). User 150 transitioning the curvature of hanger arm 126 further provides and facilitates user 150 having the ability to selectively and alternately adjust at least one of the third angle 1170, the coupling angle 440, the contact angle 1120, the area 1182, the height 1140, and the arm-to-vertical surface distance 1181.

In those embodiments (e.g., device 1100) having at least one of coupling angle 440 and contact angle 1120 that is adjustable by user 150, first pin head 1111 has a width that is greater than the width of first pin shaft 1113 to prevent a complete travel of first pin shaft 1113 through first bore 1108. Also, in the embodiment shown in FIG. 11, first flange 1115 has a width that is greater than the width of first bore 1108 in order to facilitate preventing detachment of the first pivot pin 1110 from the first bore 1108 when inserted therein. Thus, for example, and without limitation, a first end of first pin shaft 1113 (e.g., opposite a second end thereof to which first pin head 1111 is coupled to) is inserted through first bore 1108 from first side 1112, and when so inserted, first pin head 1111 rests upon first side 1112. First flange 1115 is then coupled to the first end of first pin shaft 1113 such that first flange 1115 is positioned proximate a portion of a surface of container 106 (e.g., a portion of container side wall 110) that faces into interior cavity 122. Inclusion of seal 1150 proximate at least one of first flange 1115, first pin head 1111, and first pin shaft 1113 prevents and/or mitigates leakage of fluid 102 from and/or into interior cavity 122 to and/or from exterior 120.

In the embodiment shown in FIG. 11, both of first flange 1115 and first pin head 1111 are not further coupled to first side 1112 and the portion of a surface of container 106 that faces into interior cavity 122, respectively. In other embodiments, not shown, at least one of first flange 1115 and first pin head 1111 is further coupled to at least one of first side 1112 and the portion of a surface of container 106 that faces into interior cavity 122, respectively. Thus, in the example embodiment, first section 128 is rotatably coupled to the container 106. For example, and without limitation, first flange 1115 is coupled to both the first end of the first pin shaft 1113 and the portion of a surface of container 106 that faces into interior cavity 122. The first pin head 1111 rests upon, but is not coupled to, the first side 1112, where the first side 1112 is defined and positioned on the first section 128 proximate the container 106 and the coupling pivot point 1122.

As shown in FIG. 11, first section 128 thus rotates about an axis defined by first pin shaft 1113 relative to container axis 439, and through a plurality of coupling angle 440 values (e.g., a first coupling angle 440a value and a second coupling angle 440b value that is different from the first coupling angle 440a value). User 150 pivoting first section 128 about coupling pivot point 1122 also transitions device 1100 through a plurality of contact angle 1120 values (e.g., a first contact angle 1120a value and a second contact angle 1120b value that is different from the first contact angle 1120a value). Furthermore, user 150 pivoting first section 128 about coupling pivot point 1122 also transitions device 1100 through a plurality of height 1140 values (e.g., a first height 1140a value and a second height 1140b value that is different from the first height 1140a value). Moreover, adjustment of coupling angle 440 by user 150 pivoting first section 128 about coupling pivot point 1122 transitions container 106 through a plurality of positions (e.g., a first container 106a position and a second container 106b position that is different from the first container 106a position), and further transitions device 1100 through a plurality of area 1182 values (e.g., a first area 1182 value and a second area 1182 value that is different from the first area 1182 value). Similarly, adjustment of coupling angle 440 by user 150 pivoting first section 128 about coupling pivot point 1122 transitions device 1100 through a plurality of arm-to-vertical surface distance 1181 values (e.g., a first arm-to-vertical surface distance 1181 value and a second arm-to-vertical surface distance 1181 value that is different from the first arm-to-vertical surface distance 1181 value).

In the embodiment illustrated in FIG. 11, coupling lock 1124 included in device 1100 provides and facilitates user 150 having the ability to selectively couple and decouple at least one of first pin head 1111 and first flange 1115 to and from at least one of first side 1112 and the aforementioned portion of a surface of container 106 that faces into interior cavity 122, respectively, to further facilitate the selective and alternating increasing and decreasing of at least one of the coupling angle 440, the contact angle 1120, the area 1182, the height 1140, and the arm-to-vertical surface distance 1181. In other embodiments, not shown (e.g., device embodiments where first flange 1115 is positioned proximate first side 11 12 and first pin head 1111 is positioned proximate the portion of a surface of container 106 that faces into interior cavity 122), coupling lock 1124 provides and facilitates user 150 having the ability to selectively couple and decouple at least one of first flange 1115 and first pin head 1111 to and from at least one of first side 1112 and the portion of a surface of container 106 that faces into interior cavity 122, respectively, to further facilitate the selective and alternating increasing and decreasing of at least one of the coupling angle 440, the contact angle 1120, the area 1182, the height 1140, and the arm-to-vertical surface distance 1181.

In one embodiment of the devices (e.g., device 1100) described herein, coupling lock 1124 includes a peg (not shown) that is selectively and alternately inserted and removed into and out of a correspondingly and nestingly shaped peg receptacle (not shown) defined and formed in a surface of at least one of a portion of an exterior 120 facing surface of container 106 proximate coupling pivot point 1122 and first side 1112 of first section 128 proximate coupling pivot point 1122. Thus, for example and without limitation, user 150 maintains the peg inserted into peg receptacle when he or she desires to maintain the rotatable first section 128 in a secured and fixed position (e.g., to prevent pivoting of first section 128 and to maintain coupling angle 440 at a first predetermined coupling angle 440*a* value).

In an example use case, to adjust coupling angle 440 from the first coupling angle 440*a* value to the second coupling angle 440*b* value, user 150 removes (e.g., retracts) the peg from peg receptacle, thereby permitting the otherwise non-pivotable first section 128 to pivot about the coupling pivot point 1122 to the desired second coupling angle 440*b* value. Upon reaching the second coupling angle 440*b* value, user 150 inserts the peg back into the peg receptacle to secure and affix the otherwise rotatable first section 128 at the second coupling angle 440*b* value (e.g., to again prevent pivoting of first section 128 and to maintain coupling angle 440 and container 106 at a second predetermined coupling angle 440*b* value and a second container 106*b* position, respectively). During such times when device 1100 (and, similarly, other embodiments of the devices described herein having the rotatable first section 128) is hanging from elongate structure 410, coupling lock 1124 prevents and/or reduces a probability of pivoting (e.g., slippage) of first section 128 relative to container 106. Coupling lock 1124 further provides and facilitates user 150 having the ability to securely and conveniently accommodate device 1100 to different offset structures 432 having, for example and without limitation, varying distances 432 of elongate structure(s) 410 from substantially vertical surface(s) 134.

Moreover, in some embodiments of the devices described herein, the flexible material of construction of the at least a portion of the second section 129 provides and facilitates user 150 having the ability to selectively and alternately adjust at least one of the third angle 1170, the contact angle 1120, the area 1182, the height 1140, and the arm-to-vertical surface distance 1181. In other embodiments, not shown, at least one portion of the at least one hanger arm 126 other than or in addition to the at least a portion of the second section 129 is formed of the flexible material of construction to provide similar benefits to user 150 of the devices (e.g., device 1100) described herein. For example, and without limitation, in such other embodiments, at least one of first section 128 and second section 129 is formed of the flexible material of construction to provide and facilitate the user 150 having the ability to selectively and alternately transition hanger arm 126 from a substantially straight and vertical hanger arm 126 (e.g., having an angle of arm axis 437 relative to second section axis 906 that is substantially equal to zero degrees, as shown in FIG. 1) to the arcuately curved hanger arm 126 (e.g., where an angle of arm axis 437 relative to second section axis 906 is not substantially equal to zero degrees, as shown in FIG. 4). User 150 transitioning the curvature of hanger arm 126 further provides and facilitates user 150 having the ability to selectively and alternately adjust at least one of the third angle 1170, the coupling angle 440, the contact angle 1120, the area 1182, the height 1140, and the arm-to-vertical surface distance 1181.

In those embodiments (e.g., device 1100) having third angle 1170 that is adjustable by user 150, second pin head 1164 has a width that is greater than the width of second pin shaft 1168 to prevent a complete travel of second pin head 1164 through second bore 1160. Also, in the embodiment shown in FIG. 11, second flange 1171 has a width that is greater than the width of second bore 1160 in order to facilitate preventing detachment of the second pivot pin 1162 from the second bore 1160 when inserted therein. Thus, for example, and without limitation, a first end of second pin head 1164 (e.g., opposite a second end thereof to which second pin head 1164 is coupled to) is inserted through second bore 1160 from first side 1166, and when so inserted, second pin head 1164 rests upon first side 1166. Second flange 1171 is then coupled to the first end of second pin head 1164 such that second flange 1171 is positioned proximate second side 1169. In the embodiment shown in FIG. 11, both of second flange 1171 and second pin head 1164 are not further coupled to first side 1166 and second side 1169, respectively. In other embodiments, not shown, at least one of second flange 1171 and second pin head 1164 is further coupled to at least one of first side 1166 and second side 1169, respectively. Thus, in the example embodiment, the first section 128 and the second section 129 of each hanger arm 126 of the two hanger arms 126 are rotatably coupled together at second arm section pivot point 1172. For example, and without limitation, second flange 1171 is coupled to both the first end of the second pin shaft 1168 and the second side 1169, where the second side 1169 is defined and positioned on the second section 129. The second pin head 1164 rests upon, but is not coupled to, the first side 1166, where the first side 1166 is defined and positioned on an end of the first section 128 distal the container 106. As shown in FIG. 11, second section 129 thus rotates about an axis defined by second pin shaft 1168 relative to the arm axis 437, and through a plurality of second section positions 1130 (e.g., a first second section position 1130*a* and a second second section position 1130*b* that is different from the first second section position 1130*a*).

As shown in FIG. 11, second section 129 thus rotates about an axis defined by second pin shaft 1168 relative to arm axis 437 and relative to container axis 439, and second section 129 rotates through a plurality of third angle 1170 values (e.g., a first third angle 1170*a* value and a second third angle 1170*b* value that is different from the first third angle 1170*a* value). User 150 pivoting second section 129 about second arm section pivot point 1172 also transitions device 1100 through a plurality of contact angle 1120 values (e.g., a first contact angle 1120*a* value and a second contact angle 1120*b* value that is different from the first contact angle 1120*a* value). Furthermore, user 150 pivoting second section 129 about second arm section pivot point 1172 also transitions device 1100 through a plurality of height 1140 values (e.g., a first height 1140a value and a second height 1140b value that is different from the first height 1140a value). Moreover, adjustment of third angle 1170 by user 150 pivoting second section 129 about second arm section pivot point 1172 transitions container 106 through a plurality of positions (e.g., a first container 106a position and a second container 106b position that is different from the first container 106a position), and further transitions device 1100 through a plurality of area 1182 values (e.g., a first area 1182 value and a second area 1182 value that is different from the first area 1182 value). Similarly, adjustment of third angle 1170 by user 150 pivoting second section 129 about second arm section pivot point 1172 transitions device 1100 through a plurality of arm-to-vertical surface distance 1181 values (e.g., a first arm-to-vertical surface distance 1181 value and a second arm-to-vertical surface distance 1181 value that is different from the first arm-to-vertical surface distance 1181 value).

In the embodiment illustrated in FIG. 11, arm lock mechanism 1174 included in device 1100 provides and facilitates user 150 having the ability to selectively couple and decouple at least one of second pin head 1164 and second flange 1171 to and from at least one of first side 1166 and second side 1169, respectively, to further facilitate the selective and alternating increasing and decreasing of at least one of the third angle 1170, the contact angle 1120, the area 1182, the height 1140, and the arm-to-vertical surface distance 1181. In other embodiments, not shown (e.g., device embodiments where second flange 1171 is positioned proximate first side 1166 and second pin head 1164 is positioned proximate second side 1169), arm lock mechanism 1174 provides and facilitates user 150 having the ability to selectively couple and decouple at least one of second flange 1171 and second pin head 1164 to and from at least one of first side 1166 and second side 1169, respectively, to further facilitate the selective and alternating increasing and decreasing of at least one of the third angle 1170, the contact angle 1120, the area 1182, the height 1140, and the arm-to-vertical surface distance 1181.

In one embodiment of the devices (e.g., device 1100) described herein, arm lock mechanism 1174 includes a peg (not shown) that is selectively and alternately inserted and removed into and out of a correspondingly and nestingly shaped peg receptacle (not shown) defined and formed in a surface of at least one of a portion of a portion of second section 129 facing second pin head 1164 and proximate second arm section pivot point 1172, and first side 1166 of first section 128 proximate second arm section pivot point 1172. Thus, for example and without limitation, user 150 maintains the peg inserted into peg receptacle when he or she desires to maintain the otherwise rotatable second section 129 in a secured and fixed position (e.g., to prevent pivoting of second section 129 and to maintain third angle 1170 at a first predetermined third angle 1170a value).

In another example use case, to adjust third angle 1170 from the first third angle 1170a value to the second third angle 1170b value, user 150 removes (e.g., retracts) the peg from peg receptacle, thereby permitting the otherwise non-pivotable second section 129 to pivot about the second arm section pivot point 1172 to the desired second third angle 1170b value. Upon reaching the second third angle 1170b value, user 150 inserts the peg back into the peg receptacle to secure and affix the otherwise rotatable second section 129 at the second third angle 1170b value (e.g., to again prevent pivoting of second section 129 and to maintain third angle 1170 at a second predetermined third angle 1170b value). During such times when device 1100 (and, similarly, other embodiments of the devices described herein having the rotatable second section 129) is hanging from elongate structure 410, arm lock mechanism 1174 prevents and/or reduces a probability of pivoting (e.g., slippage) of second section 129 relative to first section 128. Arm lock mechanism 1174 further provides and facilitates user 150 having the ability to securely and conveniently accommodate device 1100 to different offset structures 432 having, for example and without limitation, varying distances 432 of elongate structure(s) 410 from substantially vertical surface(s) 134.

Figure 12A:
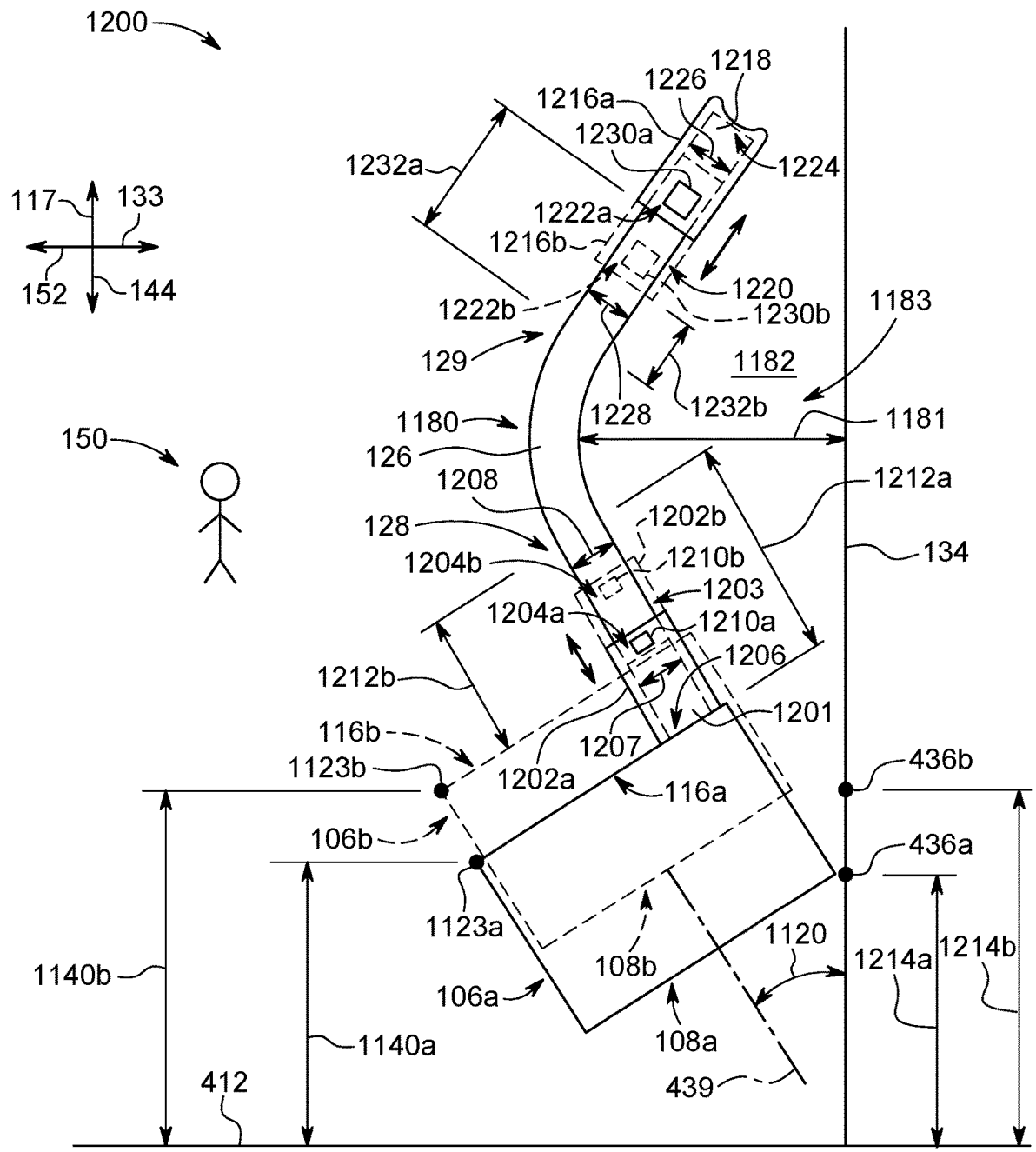
FIG. 12A is a side-view diagram of another embodiment of the device shown in FIG. 4.

FIG. 12A is a side-view diagram of another embodiment of the device shown in FIG. 4. In the embodiment shown in FIG. 12A, a device 1200 includes a lower sleeve 1202. Lower sleeve 1202 is at least one of coupled to and formed within at least a portion of at least one of the container 106 and the first section 128. In the embodiment shown in FIG. 12A, first section 128 is a two-piece first section 128, with a first part including lower sleeve 1202 positioned proximate container 106, and with a second part of first section 128 positioned proximate midsection 1180 of hanger arm 126. The lower sleeve 1202 extends generally upward 117 from the container 106. In other embodiments, not shown, lower sleeve 1202 is positioned proximate midsection 1180, and the second part of first section 128 (e.g., which does not include lower sleeve 1202) is positioned proximate container 106. In such other embodiments, lower sleeve 1202 extends generally downward 144 from hanger arm 126 proximate midsection 1180.

The lower sleeve 1202 includes a lower sleeve cavity 1201 defined within the lower sleeve 1202. Lower sleeve cavity 1201 includes a lower sleeve opening 1204 facing generally upward 117. Lower sleeve cavity 1201 extends generally downward 144 from the lower sleeve opening 1204 to a lower sleeve bottom 1206 proximate container 106. Lower sleeve cavity 1201 has a lower sleeve interior width 1207 that is substantially equal to a first section width 1208 of the first section 128. The first section 128 includes a proximate end 1203 slidingly coupled to the lower sleeve 1202 through (e.g., inside of) the lower sleeve cavity 1201.

Also, in the embodiment shown in FIG. 12A, when device 1200 is attached to supportive structure 104 (e.g., substantially vertical surface 134), the at least one hanger arm 126 is spaced from vertical surface 134 (e.g., wall) by an arm-to-vertical surface distance 1181. For example, and without limitation, the at least one hanger arm 126 further includes a midsection 1180 positioned between the distal end 130 (not shown) and the container 106. The midsection 1180 defines an approximate boundary between first section 128 and second section 129. Midsection 1180 is further positioned approximately equidistant between distal end 130 and container 106. In other embodiments, not shown, midsection 1180 is positioned closer to distal end 130 than to container 106. In still other embodiments, not shown, midsection 1180 is positioned nearer to container 106 than to distal end 130. By manipulating at least one of the first section 128 and the lower sleeve 1202, user 150 of device 1200 selectively adjusts a position of proximate end 1203 in lower sleeve cavity 1201 to facilitate alternately increasing and decreasing a first section distance 1212 between the container top 116 and the midsection 1180. Furthermore, when device 1200 is attached to supportive structure 104 (e.g., substantially vertical surface 134), point 1123 on container top 116 is positioned above ground surface 412 by height 1140, and the selective adjustment of the position of proximate end 1203 in lower sleeve cavity 1201 further facilitates selectively increasing and decreasing the height 1140.

Further, in the embodiment shown in FIG. 12A, when device 1200 is attached to the supportive structure 104 (e.g., substantially vertical surface 134), a rearward 133 facing portion of container 106 contacts the substantially vertical surface 134 at at least one of contact point 436 and contact region 436. The at least one of the contact point 436 and the contact region 436 is positioned above ground surface 412 by an elevation 1214. The above described selective adjustment of the position of proximate end 1203 in lower sleeve cavity 1201 further facilitates selectively increasing and decreasing the elevation 1214 by user 150. Also, when the device 1200 is attached to supportive structure 104 (e.g., substantially vertical surface), first plane 1183 (having area 1182) is approximately defined between container 106, the at least one hanger arm 126, and the substantially vertical surface 134. The above described selective adjustment of the position of proximate end 1203 in lower sleeve cavity 1201 further facilitates selectively increasing and decreasing the area 1182 by the user 150 when device 1200 is attached to supportive structure (e.g., substantially vertical surface 134). Likewise, the above described selective adjustment of the position of proximate end 1203 in lower sleeve cavity 1201 further facilitates selectively increasing and decreasing the contact angle 1120 by the user 150 when device 1200 is attached to supportive structure (e.g., substantially vertical surface 134).

To provide and facilitate adjustment of the position of proximate end 1203 in lower sleeve cavity 1201 by user 150, device 1200 includes a lower sleeve lock mechanism 1210 coupled to the lower sleeve 1202. Lower sleeve lock mechanism 1210 is selectively coupled to the first section 128 when proximate end 1203 is slidingly coupled to the lower sleeve 1202 through the lower sleeve cavity 1201. By the action and manipulation by user 150 of device 1200, lower sleeve lock mechanism 1210 selectively and alternately couples and decouples the first section 128 from the lower sleeve 1202 to further facilitate selectively and alternately increasing and decreasing at least one of the height 1140, the area 1182, and the elevation 1214.

In the embodiment shown in FIG. 12A, device 1200 also includes an upper sleeve 1216. Upper sleeve 1216 is at least one of coupled to and formed within at least a portion of the second section 129 of the at least one hanger arm 126. In the embodiment shown in FIG. 12A, second section 129 is a two-piece second section 129, with a first part including upper sleeve 1216 positioned proximate distal end 130 (not shown), and with a second part of second section 129 positioned proximate midsection 1180 of hanger arm 126. The upper sleeve 1216 extends generally downward 144 from distal end 130. In other embodiments, not shown, upper sleeve 1216 is positioned proximate midsection 1180, and the second part of second section (e.g., which does not include upper sleeve 1216) is positioned proximate distal end 130. In such other embodiments, upper sleeve 1216 extends generally upward 117 from hanger arm 126 proximate midsection 1180.

The upper sleeve 1216 includes an upper sleeve cavity 1218 defined within the upper sleeve 1216. Upper sleeve opening 1222 includes an upper sleeve opening 1222 facing generally downward 144. Upper sleeve cavity 1218 extends generally upward 117 from the upper sleeve opening 1222 to an upper sleeve top 1224 proximate distal end 130. Upper sleeve cavity 1218 has an upper sleeve interior width 1226 that is substantially equal to a second section width 1228 of the second section 129. The second section 129 includes an upper end 1220 slidingly coupled to the upper sleeve 1216 through (e.g., inside of) the upper sleeve cavity 1218.

Also, in the embodiment shown in FIG. 12A, by manipulating at least one of the second section 129 and the upper sleeve 1216, user 150 of device 1200 selectively adjusts a position of upper end 1220 in upper sleeve cavity 1218 to facilitate alternately increasing and decreasing a second section distance 1232 between the distal end 130 and the midsection 1180. Furthermore, when device 1200 is attached to supportive structure 104 (e.g., substantially vertical surface 134), point 1123 on container top 116 is positioned about ground surface 412 by height 1140, and the selective adjustment of upper end 1220 in upper sleeve cavity 1218 further facilitates selectively increasing and decreasing the height 1140.

Further, in the embodiment shown in FIG. 12A, when device 1200 is attached to the supportive structure 104 (e.g., substantially vertical surface 134), the rearward 133 facing portion of container 106 contacts the substantially vertical surface 134 at at least one of contact point 436 and contact region 436. The at least one of the contact point 436 and the contact region 436 is positioned above ground surface 412 by the elevation 1214. The above described selective adjustment of the position of upper end 1220 in upper sleeve cavity 1218 further facilitates selectively increasing and decreasing the elevation 1214 by user 150. Also, when the device 1200 is attached to supportive structure 104 (e.g., substantially vertical surface), first plane 1183 (having area 1182) is approximately defined between container 106, the at least one hanger arm 126, and the substantially vertical surface 134. The above described selective adjustment of the position of upper end 1220 in upper sleeve cavity 1218 further facilitates selectively increasing and decreasing the area 1182 by the user 150 when device 1200 is attached to supportive structure (e.g., substantially vertical surface 134). Likewise, the above described selective adjustment of the position of upper end 1220 in upper sleeve cavity 1218 further facilitates selectively increasing and decreasing the contact angle 1120 by the user 150 when device 1200 is attached to supportive structure (e.g., substantially vertical surface 134).

To provide and facilitate adjustment of the position of upper end 1220 in upper sleeve cavity 1218 by user 150, device 1200 includes an upper sleeve lock mechanism 1230 coupled to the upper sleeve 1216. Upper sleeve lock mechanism 1230 is selectively coupled to the second section 129 when upper end 1220 is slidingly coupled to the upper sleeve 1216 through the upper sleeve cavity 1218. By the action and manipulation by user 150 of device 1200, upper sleeve lock mechanism 1230 selectively and alternately couples and decouples the second section 129 from the upper sleeve 1216 to further facilitate selectively and alternately increasing and decreasing at least one of the height 1140, the area 1182, and the elevation 1214.

Figure 12B:
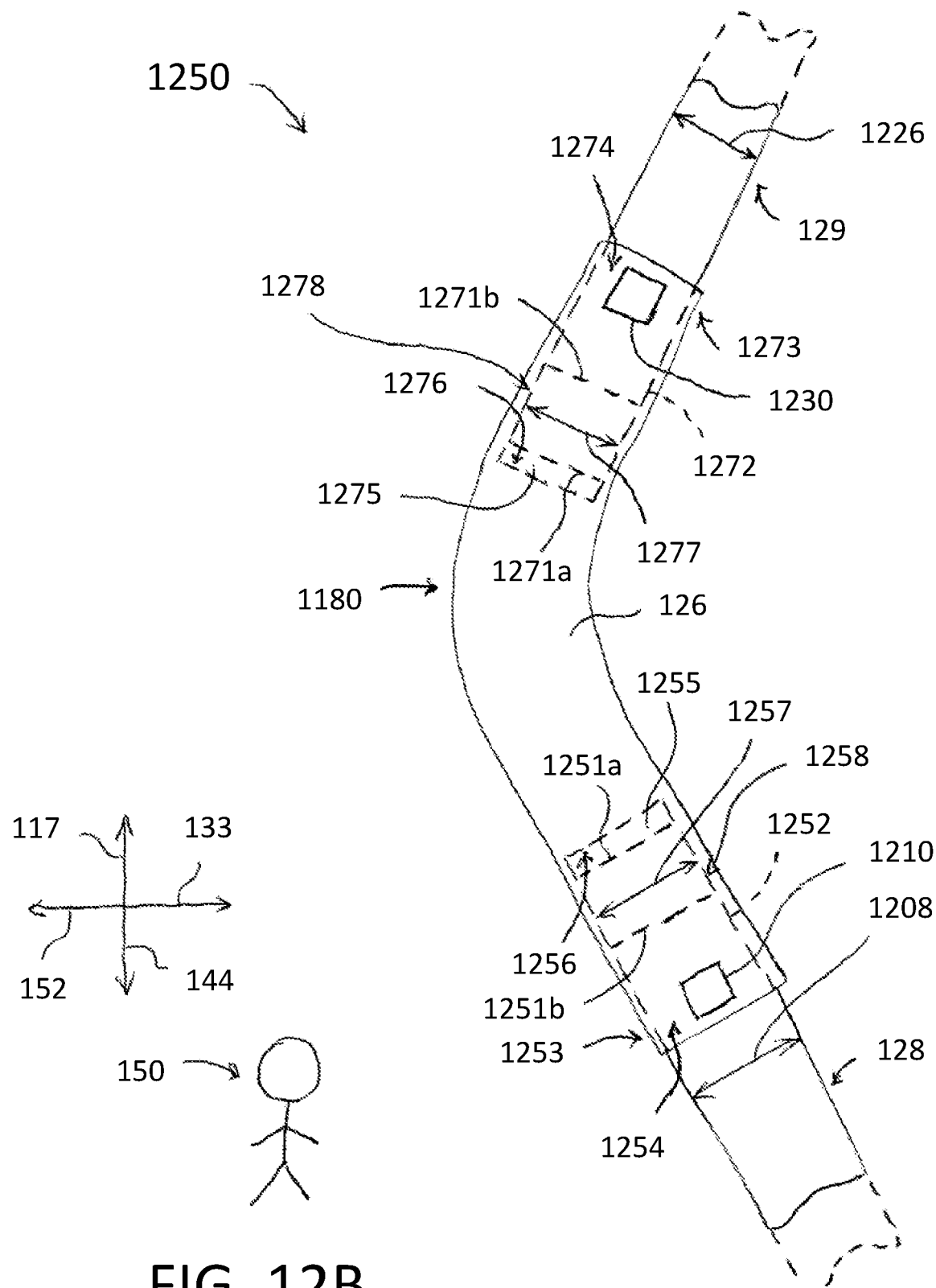
FIG. 12B is a side-view diagram of an alternative embodiment of the device shown in FIG. 12A.

FIG. 12B is a side-view diagram of an alternative embodiment of the device shown in FIG. 12A. As shown in FIG. 12B, a device 1250 includes a lower sleeve 1252 at least one of coupled to and formed in a first end 1253 of the midsection 1180. The lower sleeve 1252 extends distally (e.g., generally downwardly 144) from the first end 1253 toward the container 106 (not shown in FIG. 12B). The lower sleeve 1252 includes a lower sleeve cavity 1255 defined within the lower sleeve 1252. The lower sleeve cavity 1255 includes a lower sleeve opening 1254 positioned opposite from the midsection 1180 and facing away from the midsection 1180. The lower sleeve opening 1254 extends distally from the lower sleeve opening 1254 to a lower sleeve bottom 1256 proximate the midsection 1180. The lower sleeve cavity 1255 has a lower sleeve interior width 1257 that is greater than or substantially equal to the first section width 1208 of the first section 128. In device 1250, the first section 128 includes a distal end 1258 slidingly coupled to the lower sleeve 1252 through the lower sleeve cavity 1255.

By manipulating at least one of the first section 128 and the lower sleeve 1252, the user 150 of device 1250 selectively adjusts a position of the distal end 1258 in the lower sleeve cavity 1255 to facilitate alternately increasing and decreasing the first section distance 1212 between the container 106 and the midsection 1180, substantially as shown and described above with reference to FIG. 12A. Device 1250 also includes lower sleeve lock mechanism 1210 coupled to the lower sleeve 1252 and selectively coupled to the first section 128 when the distal end 1258 is slidingly coupled to the lower sleeve 1252 through the lower sleeve cavity 1255. The lower sleeve lock mechanism 1210 is configured to selectively couple and decouple the first section 128 to the lower sleeve 1252 to further facilitate selectively increasing and decreasing the first section distance 1212 (e.g., from a first position 1251*a* to a second position 1251*b*).

Device 1250 includes an upper sleeve 1272 at least one of coupled to and formed in a second end 1273 of the midsection 1180. The upper sleeve 1272 extends distally (e.g., generally upwardly 117) from the second end 1273 toward the distal end 130 (not shown in FIG. 12B). The upper sleeve 1272 includes an upper sleeve cavity 1275 defined within the upper sleeve 1272. The upper sleeve cavity 1275 includes an upper sleeve opening 1274 positioned opposite from the midsection 1180 and facing away from the midsection 1180. The lower upper opening 1274 extends distally from the upper sleeve opening 1274 to an upper sleeve bottom 1276 proximate the midsection 1180. The upper sleeve cavity 1275 has an upper sleeve interior width 1277 that is greater than or substantially equal to the second section width 1226 of the second section 129. In device 1250, the second section 129 includes a distal end 1278 slidingly coupled to the upper sleeve 1272 through the upper sleeve cavity 1275.

By manipulating at least one of the second section 129 and the upper sleeve 1272, the user 150 of device 1250 selectively adjusts a position of the distal end 1278 in the upper sleeve cavity 1275 to facilitate alternately increasing and decreasing the second section distance 1232 between the distal end 130 and the midsection 1180, substantially as shown and described above with reference to FIG. 12A. Device 1250 also includes upper sleeve lock mechanism 1230 coupled to the upper sleeve 1272 and selectively coupled to the second section 129 when the distal end 1278 is slidingly coupled to the upper sleeve 1272 through the upper sleeve cavity 1275. The upper sleeve lock mechanism 1230 is configured to selectively couple and decouple the second section 129 to the upper sleeve 1272 to further facilitate selectively increasing and decreasing the second section distance 1232 (e.g., from a first position 1271*a* to a second position 1271*b*).

Figure 13:
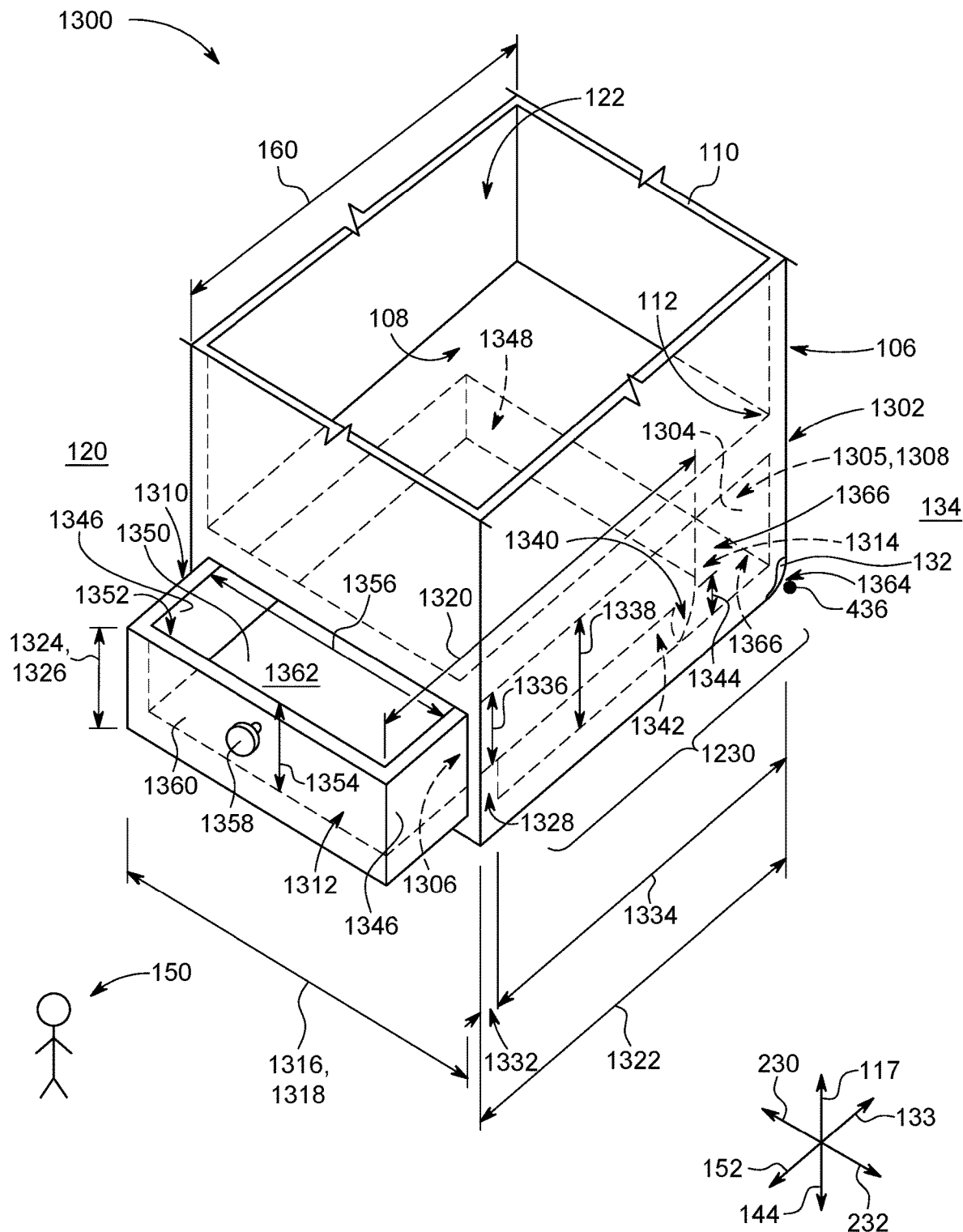
FIG. 13 is a perspective-view diagram of an alternative embodiment of the devices shown in FIGS. 1, 2, 4, 10, 11, and 12A.

FIG. 13 is a perspective-view diagram of an alternative embodiment of the devices shown in FIGS. 1, 2, 4, 10, 11, and 12A. In the embodiment shown in FIG. 13, a device 1300 includes a base extension 1302 coupled the container base 108 of container 106. Base extension 1302 extends generally downward 144 from the container base 108. Base extension 1302 includes an under-base cavity 1304 defined within the base extension 1302. The under-base cavity 1304 includes a first under-base opening 1306 facing generally frontward 152. The under-base cavity 1304 extends generally rearward 133 through at least a portion of the base extension 1302 to a cavity rearward 133 extent 1305.

Also, in the embodiment shown in FIG. 13, the under-base cavity 1304 extends generally rearward 133 entirely through the base extension 1302 from the first under-base opening 1306 to a second under-base opening 1308. The second under-base opening 1308 faces generally rearwardly 133. In other embodiments, not shown, under-base cavity 1304 does not extend entirely through base extension 1302, but, rather, extends rearwardly 133 from first under-base opening 1306 only part way through base extension 1302 (e.g., extending between half and seven eights through the base extension 1302). In such other embodiments, device 1300 does not include the second under-base opening 1308.

Device 1300 also includes at least one drawer 1310. Drawer 1310 includes a generally frontward 152 facing drawer front 1312 and a generally rearward 133 facing drawer back 1314. Drawer 1310 has a drawer width 1316 that is less than or substantially equal to a cavity width 1318 of the under-base cavity 1304. Drawer 1310 also has a drawer length 1320 defined as a distance between the drawer front 1312 and the drawer back 1314. The drawer length 1320 is less than or substantially equal to a cavity length 1322, the cavity length 1322 defined as a distance between the first under-base opening 1306 and the cavity rearward 133 extent 1305. The drawer 1310 is slidingly inserted into the under-base cavity 1304 with the drawer back 1314 facing the cavity rearward 133 extent 1305.

Also, in device 1300, drawer 1310 also has a drawer height 1324 that is less than or substantially equal to an opening height 1326 of the first under-base opening 1306. The under-base cavity 1304 also includes a frontward section 1328 and a rearward section 1330. The frontward section 1328 has a first length 1332, and the rearward section 1330 has a second length 1334. The first length 1332 is less than the second length 1334, and a sum of the first length 1332 and the second length 1334 is substantially equal to the cavity length 1322. The frontward section 1328 also has a first height 1336 that is greater than or substantially equal to the drawer height 1324, and the rearward section 1330 has a second height 1338. In the embodiment shown in FIG. 13, the second height 1338 is greater than the first height 1336. In other embodiments, not shown, the second height 1338 is substantially equal to the first height 1336.

Further, in the embodiment shown in FIG. 13, drawer 1310 includes a drawer stop 1340 coupled to a generally downward 144 facing drawer surface 1342 of the drawer 1310. The drawer stop 1310 extends generally downward 144 from the drawer surface 1342 by a stop distance 1344. The stop distance 1344 is greater than zero. The stop distance 1344 is also less than or substantially equal to a difference between the second height 1338 and the first height 1336. Drawer 1310 further includes at least two drawer side walls 1346 coupled to and between the drawer front 1312 and the drawer back 1314. The at least two drawer side walls 1346 are positioned opposite one another, and the at least two drawer side walls 1346 are separated by a distance that is less than or substantially equal to the drawer width 1316. Drawer 1310 further includes one drawer cavity 1348 defined by the drawer front 1312, the drawer back 1314, and a drawer base 1350. The drawer cavity 1348 includes a drawer cavity opening 1352 facing generally upward 117, and the drawer cavity 1348 extends generally downward 144 through at least a portion of the drawer 1310 to the drawer base 1350. The at least one drawer cavity 1348 has a drawer cavity depth 1354 that is less than the drawer height 1324 and the drawer cavity 1348 also has a drawer cavity width 1356 that is less than the drawer width 1316. In other embodiments, not shown, drawer 1310 does not include drawer stop 1340. In such other embodiments, the height of the under-base cavity 1304 is substantially equal to first height 1336, and under-base cavity 1304 does not include a separate frontward section 1328 and separate rearward section 1330.

Although illustrated as a drawer 1310 that alternately may be pushed and pulled into and out of the under-base cavity 1304 in the disclosed embodiments of device 1300 in frontward 152 and rearward 133 directions, respectively, a person of ordinary skill in the art will recognize and appreciate that the drawer 1310 may alternatively be positioned in device 1300 from a leftward 230 to rightward 232 direction, or similarly, in a rightward 232 to leftward 230 direction. Furthermore, a person of ordinary skill in the art will recognize and appreciate that, in additional embodiments of the disclosed device having one or more drawers and/or at least one under-base cavity 1304 (e.g., as shown and described herein), the orientation of the drawer(s) and/or the at least one under-base cavity 1304 may be similarly varied in the aforementioned manner.

Figure 14A:
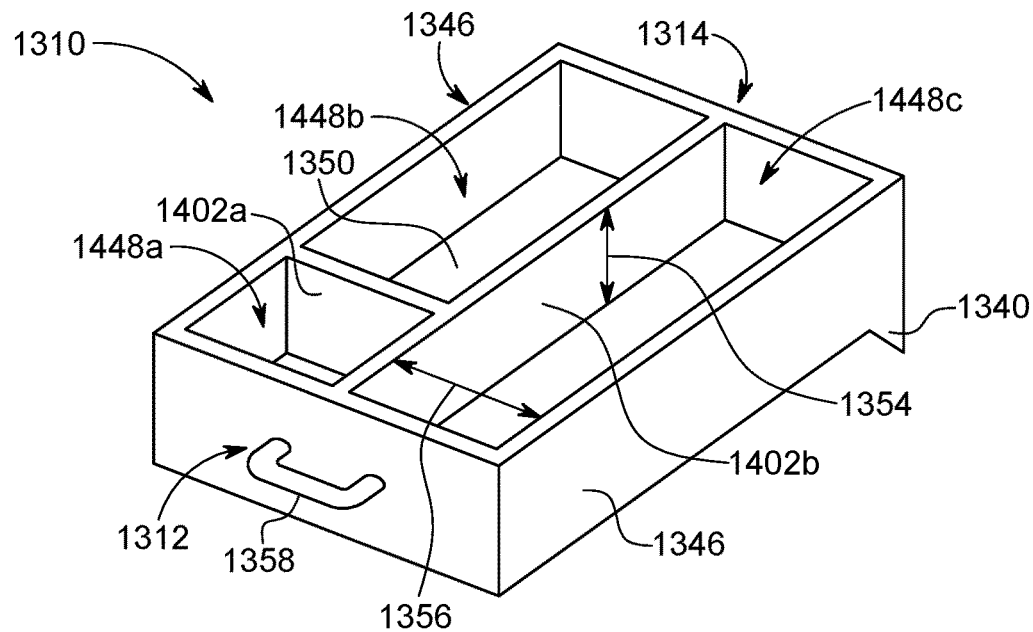
FIG. 14A is a perspective-view diagram of an alternative embodiment of the drawer shown in FIG. 13.

In another embodiment shown in FIG. 14A, drawer 1310 includes a plurality of drawer cavities 1448 (e.g., a first drawer cavity 1448a, a second drawer cavity 1448b, and a third drawer cavity 1448c). In the embodiment shown in FIG. 14A, first drawer cavity 1448a is defined by a first portion of the drawer front 1312, a first drawer cavity divider 1404a, a first portion of a second drawer divider 1404b, a first portion of a first one of the two drawer side walls 1346, and the drawer base 1350. Second drawer cavity 1448b is defined by a first portion of the drawer back 1314, the first drawer cavity divider 1404a, a second portion of the second drawer divider 1404b, a second portion of the first one of the two drawer side walls 1346, and the drawer base 1350. Third drawer cavity 1448c is defined by a second portion of the drawer back 1314, the second drawer divider 1404b, a second one of the two drawer side walls 1346, and the drawer base 1350.

Also, in the embodiment shown in FIG. 14A, each drawer cavity 1448 of the plurality of drawer cavities 1448 has substantially equivalent drawer cavity depths 1354 and drawer cavity widths 1356, but each drawer cavity 1448 of the plurality of drawer cavities 1448 has a different volume. In other embodiments, not shown, each drawer cavity 1448 of the plurality of drawer cavities 1448 has a substantially equivalent volume (e.g., embodiments in which the plurality of drawer cavities 1448 includes an even number of drawer cavities 1448). In still other embodiments, not shown, each drawer cavity 1448 of the plurality of drawer cavities 1448 does not have substantially drawer cavity depth 1354, and in yet other embodiments, not shown, each drawer cavity 1448 of the plurality of drawer cavities 1448 does not have substantially drawer cavity width 1356.

Drawer 1310 further includes at least one drawer grip 1358. Drawer grip 1358 is at least one of formed in and coupled to a frontward 152 facing drawer front surface 1360 of the drawer front 1312. Drawer grip 1358 provides and facilitates user 150 of device 1300 to selectively and alternately slide the drawer 1310 rearwardly 133 and frontwardly 152 into and out of, respectively, the under-base cavity 1304. User 150 sliding the drawer 1310 frontward also facilitates increasing a drawer cavity opening area 1362 exposed to the exterior 120 of device 1300. Similarly, user 150 sliding the drawer 1310 rearward 133 further facilitates decreasing the drawer cavity opening area 1362 exposed to exterior 120.

Moreover, when device 1300 is attached to supportive structure 104 (e.g., substantially vertical surface 134, not shown) through at least one hanger arm 126, not shown, a rearward 133 facing portion of the base extension 1302 contacts the substantially vertical surface 134 at the at least one of the contact point 436 and the contact region 436. The rearward 133 facing portion of the base extension 1302 includes an arcuate fillet 1364 formed at a rearward 133 downward 144 corner 1366 of the base extension 1302. The arcuate fillet 1364 is convexly formed with respect to the substantially vertical surface 134 and is concavely formed with respect to the under-base cavity 1304. When attached to the supportive structure 104, device 1300 further contacts the substantially vertical surface 134 at the arcuate fillet 1364. In other embodiments, not shown, device 1300 does not include arcuate fillet 1364. In such other embodiments, in place of arcuate fillet 1364, corner 1366 of base extension 1302 includes, for example, and without limitation, a substantially square corner, substantially as shown and described above with reference to FIG. 8.

Device 1300 also includes bumper 132 coupled to an exterior 120 surface of the rearward 133 facing portion of the base extension 1302. When device 1300 is attached to supportive structure 104 (e.g., substantially vertical surface 134), device 1300 further contacts the substantially vertical surface 134 at the bumper 132. In the embodiment shown in FIG. 13, bumper 132 is coupled to the exterior 120 rearward 133 facing surface of arcuate fillet 1364 and, when hanging from supportive structure 104 (e.g., substantially vertical surface 134), device 1300 further contacts the substantially vertical surface 134 at the bumper 132.

Figure 14B:
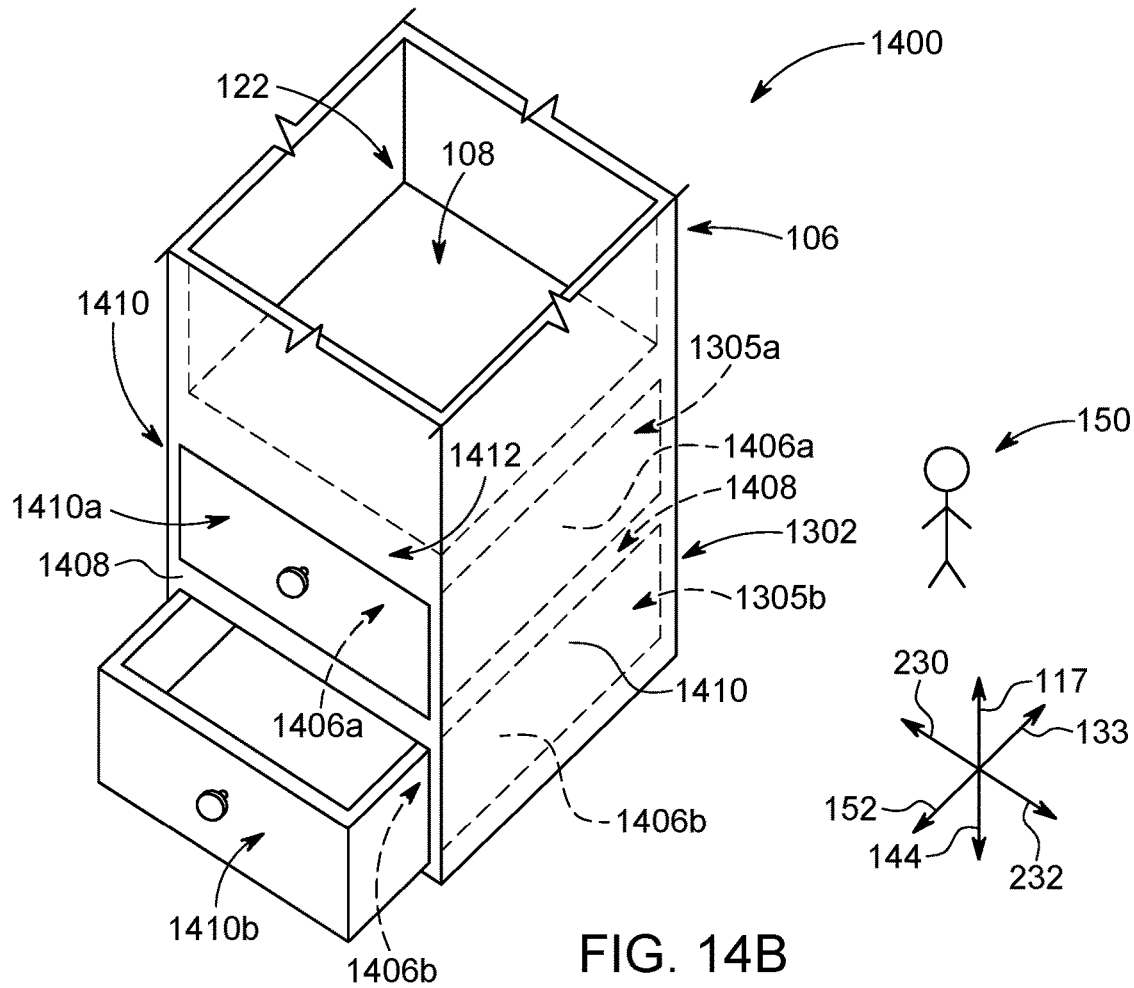
FIG. 14B is a perspective-view diagram of an alternative embodiment of the device shown in FIG. 13.

In yet another embodiment shown in FIG. 14B, a device 1400 includes a plurality of drawers 1410 (e.g., a first drawer 1410a and a second drawer 1410b). In the embodiment shown in FIG. 14B, each drawer 1410 of the plurality of drawers 1410 are stacked vertically beneath container base 108. For example, and without limitation, immediately beneath (e.g., downward 144 from) container base 108, first drawer 1410a is slidingly inserted into a first under-base cavity 1406a, substantially as shown and described above with reference to FIG. 13. Second drawer 1410b is positioned beneath (e.g., downward 144 from) first drawer 1410a. Second drawer 1410b is slidingly inserted into a second under-base cavity 1406b, substantially as shown and described above with reference to FIG. 13. Device 1400 also includes a horizontal drawer separation 1408 positioned between first drawer 1410a and second drawer 1410b. Horizontal drawer separation 1408 extends from a left 230 base extension side wall 1410 to a right 232 base extension side wall 1410. Horizontal drawer separation 1408 further extends from a base extension front surface 1412 to the respective cavity rearward 133 extent 1305 of first under-base cavity 1404a and second under-base cavity 1404b.

Figure 15:
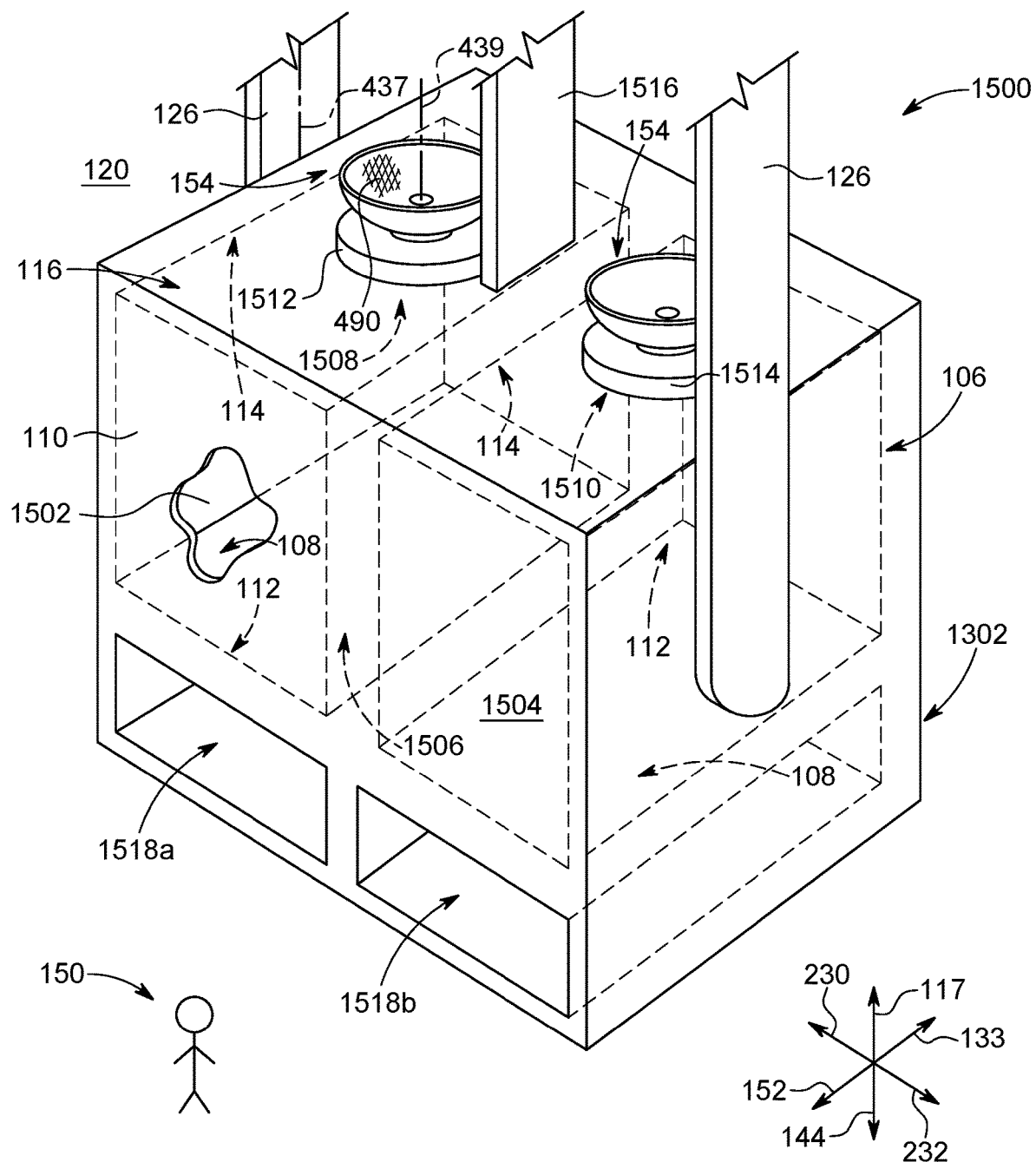
FIG. 15 is a perspective-view diagram of another embodiment of the device shown in FIGS. 1, 2, 4, 10, 11, 12A, 13, and 14.

FIG. 15 is a perspective-view diagram of another embodiment of the device shown in FIGS. 1, 2, 4, 10, 11, 12A, 13, and 14. In the embodiment shown in FIG. 15, container 106 of a device 1500 includes a plurality of interior cavities 122. The plurality of interior cavities 122 includes a first interior cavity 1502 and a second interior cavity 1504. In other embodiments, not shown, the plurality of interior cavities 122 includes more than two interior cavities 122. The first interior cavity 1502 is positioned adjacent the second interior cavity 1504. Device 1500 also includes an interior cavity separation 1506 coupled to and between a frontward 152 facing portion of the at least one container side wall 110 and a rearward 133 facing portion of the at least one container side wall 110. Separation 1506 is further coupled to container base 108. In other embodiments, not shown, separation 1506 is coupled to and between a leftward 230 facing portion of the at least one container side wall 110 and a rightward 232 facing portion of the at least one container side wall 110, with separation 1506 further coupled to container base 108. Separation 1506 separates (e.g., structurally isolates) the first interior cavity 1502 from the second interior cavity 1504, and thus isolate a first liquid 102 contained in first interior cavity 1502 from a second liquid 102 contained in second interior cavity 1504.

Also, in the embodiment shown in FIG. 15, device 1500 includes a plurality of container openings 118. The plurality of container openings 118 includes a first container opening 1508 and a second container opening 1510. In other embodiments, not shown (e.g., embodiments including more than two interior cavities 122), the plurality of container openings 119 includes more than two container openings 122. In device 1500, each container opening 118 of the plurality of container openings 118 is defined in the container top 116. Each container opening 118 of the plurality of container openings 118 in device 1500 provides and facilitates access from the exterior 120 to a respective interior cavity 122 of the plurality of interior cavities 122.

Device 1500 further includes a plurality of pump assemblies 124. The plurality of pump assemblies 124 (e.g., a plurality of dish-top pumps 154) includes a first pump assembly 1512 and a second pump assembly 1514. In other embodiments, not shown (e.g., embodiments including more than two interior cavities 122 and/or more than two container openings 118), the plurality of pump assemblies 124 includes more than two pump assemblies 124. Each pump assembly 124 of the plurality of pump assemblies 124 is coupled to the container top 116. The first pump assembly 1512 extends through the first container opening 1508 into the first interior cavity 1502, and the second pump assembly 1514 extends through the second container opening 1510 into the second interior cavity 1504.

Further, in the embodiment shown in FIG. 15, device 1500 includes a third hanger arm 1516 coupled to the container 106. The third hanger arm 1516 is positioned laterally between the first and the second hanger arms 126. The third hanger arm 1516 extends generally upward 117 from the container 106. Furthermore, in device 1500, the third hanger arm 1516 further extends generally upward 117 from the container 106 by the arm distance 204, substantially as shown and described above with reference to FIG. 2. In other embodiments, not shown, the first and second hanger arms 126 extend generally upward 117 from container 106 by a distance that is less than arm distance 204. In such other embodiments, third hanger arm 1516 extends generally upward 117 from container 106, and at least one of first and second hanger arms 126 is coupled to third hanger arm 1516 at a point (not shown) on third hanger arm 1516 positioned between container 106 and distal end 130 (not shown) of third hanger arm 1516.

In yet other embodiments, not shown, third hanger arm 1516 further includes one or more of the several features shown and described above with reference to FIG. 1 (e.g., a substantially straight third hanger arm 1516 that extends generally upward 117 and substantially vertically from container 106), FIG. 2 (e.g., a third hanger arm 1516 coupled to brace 206), FIG. 4 (e.g., an arcuately curved third hanger arm 1516), FIG. 10 (e.g., a third hanger arm 1516 having a second angle 1006 that is selectively and alternately increasable and decreasable by user 150), FIG. 11 (e.g., a third hanger arm 1516 having at least one of a third angle 1170 and a coupling angle 440 that is selectively and alternately increasable and decreasable by user 150), and FIG. 12A (e.g., a third hanger arm 1516 having at least one of a lower sleeve 1202 and an upper sleeve 1216). Moreover, in still more embodiments, not shown, the devices shown and described above include more than three hanger arms coupled to container 106 at one or more positions different from where third hanger arm 1516 is coupled to container 106 and different from where first and second hanger arms 126 are coupled to container 106.

Device 1500 further includes a plurality of under-base cavities 1518. The plurality of under-base cavities 1518 includes a first under-base cavity 1518a and a second under-base cavity 1518b. In other embodiments, not shown, the plurality of under-base cavities 1518 includes more than two under-base cavities 1518. In the embodiment shown in FIG. 15, the first under-base cavity 1518a is positioned adjacent to and to the left 230 of the second under-base cavity 1518. In other embodiments, the first under-base cavity 1518a is positioned adjacent to and atop 117 the second under-base cavity 1518b, substantially as shown and described above with reference to FIG. 14B. Also, in the embodiment shown in FIG. 15, each under-base cavity 1518 of the plurality of under-base cavities 1518 does not include a drawer 1410 and/or a drawer 1310. In other embodiments, not shown, device 1500 further includes at least one drawer 1410 and/or at least one drawer 1310, slidingly inserted into at least one under-base cavity 1518 of the plurality of under-base cavities 1518.

Figure 16:
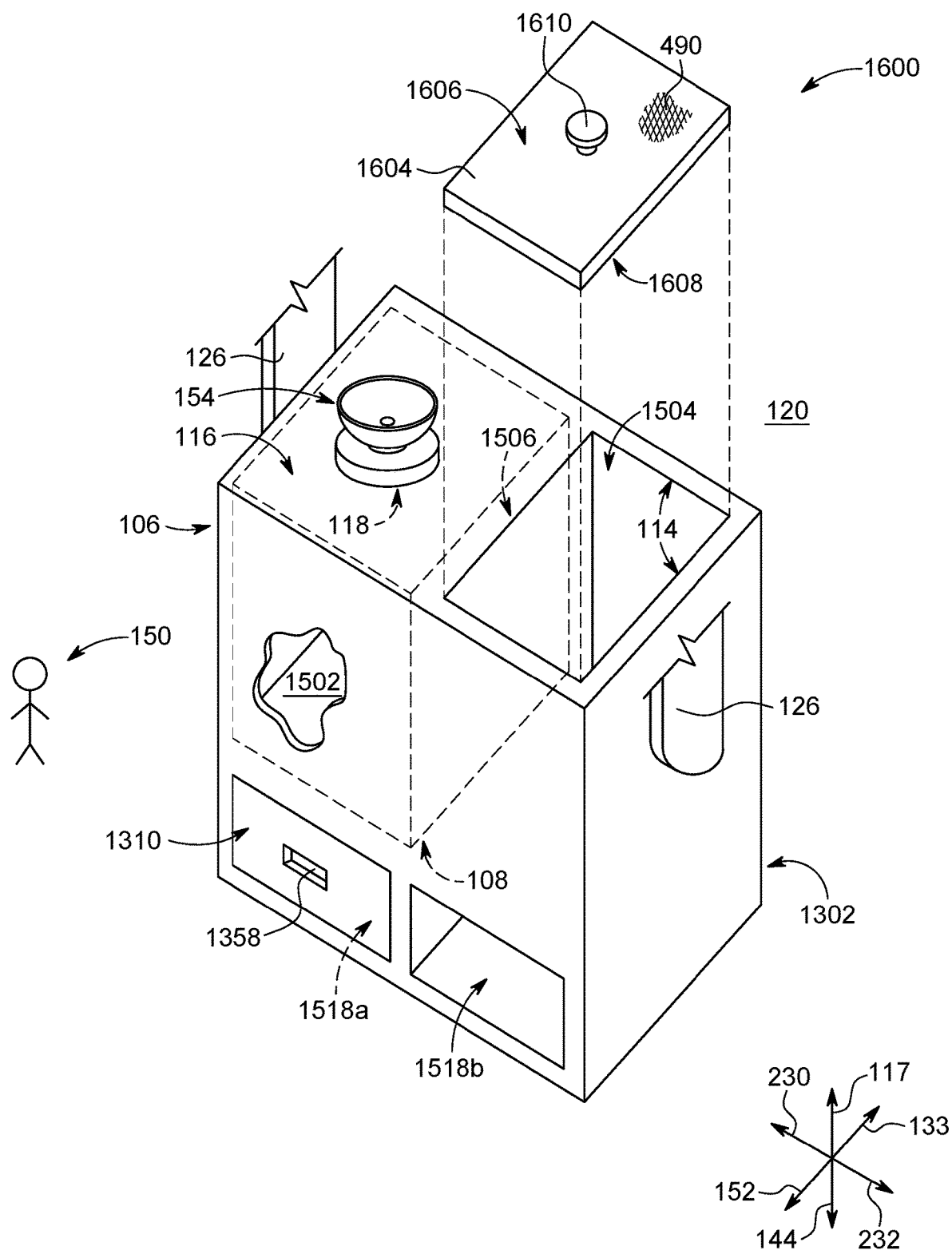
FIG. 16 is a perspective-view diagram of an alternative embodiment of the device shown in FIG. 15.

FIG. 16 is a perspective-view diagram of an alternative embodiment of the device shown in FIG. 15. In the embodiment shown in FIG. 16, in a device 1600, the container top 116 covers the first interior cavity 1502, but the container top 116 does not cover the second interior cavity 1504. Device 1600 also includes one pump assembly 124 (e.g., dish-top pump 154) coupled to the container top 116. The one pump assembly 124 extends through the container opening 118 into the first interior cavity 1502, substantially as shown and described above with reference to FIG. 15. In other embodiments, not shown (e.g., embodiments having three interior cavities 122, where two of the three interior cavities 122 are covered by container top 116, and where a third interior cavity 122 is not covered by container top 116), a plurality of pump assemblies 124 is present in the device. Also, in the embodiment shown in FIG. 16, the pump assembly 124 is coupled to the container top 116 and extends through the container opening 118 into the first interior cavity 1502. Further, the second interior cavity (1504) is exposed to the exterior 120.

Device 1600 includes at least one cover 1604. Cover 1604 includes a cover top 1606 (e.g., a cover top surface) and an opposing cover bottom 1608 (e.g., a cover bottom surface). In the embodiment shown in FIG. 16, cover 1604 also includes a cover grip 1610 coupled to cover top 1606. In other embodiments, not shown, device 1600 does not include cover grip 1610. In still other embodiments, not shown (e.g., embodiments in which more than one of the plurality of interior cavities 122 is not covered by container top 116), the device includes a plurality of covers 1604, with one cover 1604 of the plurality of covers 1604 for each respective interior cavity 122 that is uncovered by container top 116. Also, in the embodiment shown in FIG. 16, the cover 1604 is removably coupled to the second interior cavity 1504 proximate the top edge 114 thereof. In other embodiments, not shown, cover 1604 is hingedly coupled to the second interior cavity 1504 (e.g., coupled using at least one hinge, not shown) proximate the top edge 114 thereof. For example, and without limitation, a hinge coupled to a rearward 133 portion of top edge 114 and coupled to a rearward 133 portion of cover bottom 1608 provides and facilitates user 150 of device 1600 having the ability to alternately open and close cover 1604 (e.g., by manipulating cover grip 1610) to thereby alternately expose and cover second interior cavity 1504 to exterior 120.

Figure 17:
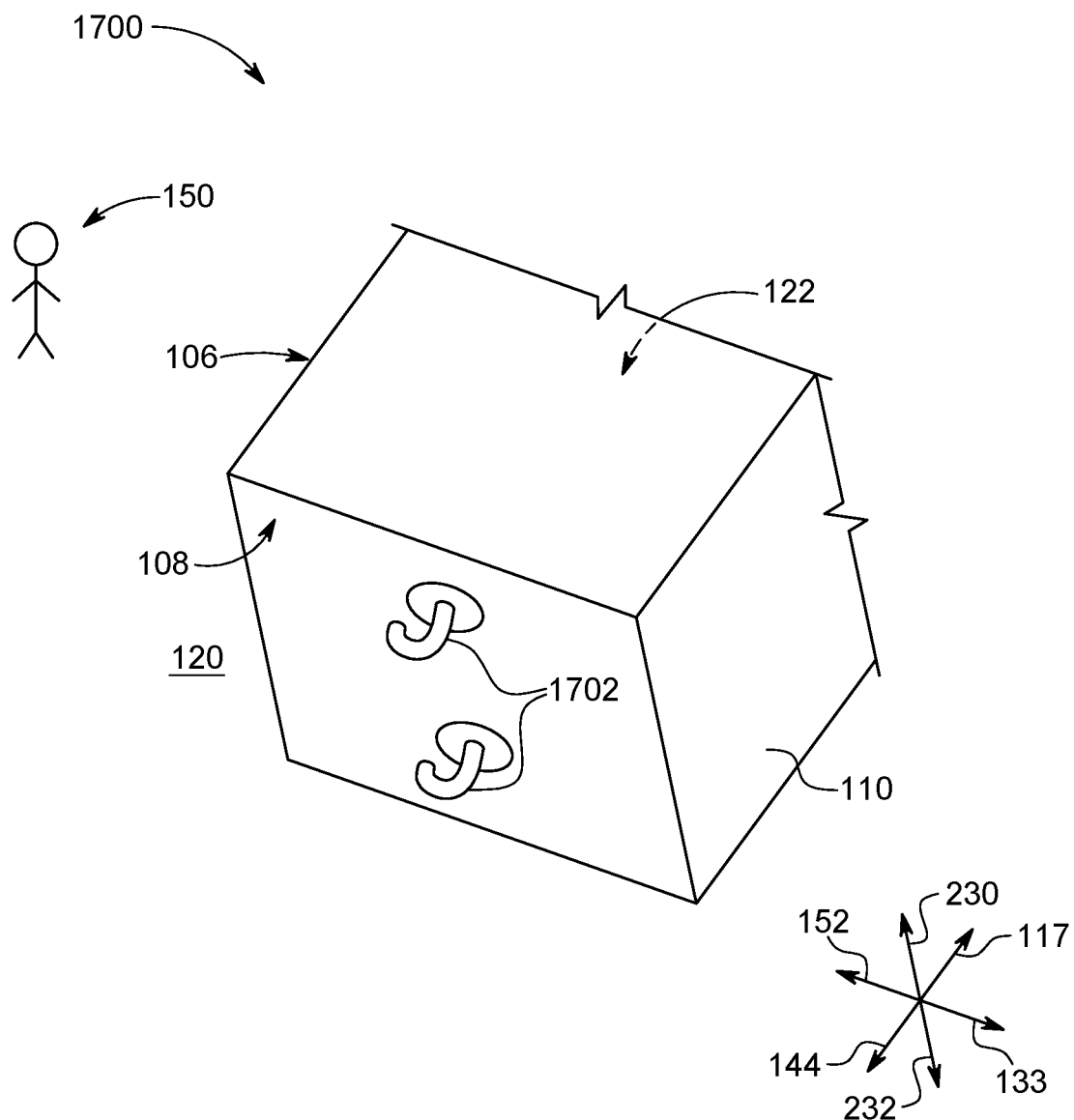
FIG. 17 is a perspective-view diagram of another embodiment of the devices shown in FIGS. 1, 2, 4, 10, 11, 12A, and 13-16.

FIG. 17 is a perspective-view diagram of another embodiment of the devices shown in FIGS. 1, 2, 4, 10, 11, 12A, and 13-16. In the embodiment shown in FIG. 17, a device 1700 includes at least one base hook 1702 coupled to base 108 of container 106. In those embodiments of the device including base extension 1302 (e.g., as shown and described above with reference to FIG. 13), the at least one base hook 1702 is coupled to a downward 144 facing surface of base extension 1302. The at least one base hook 1702 provides and facilitates user 150 having the ability to hang item(s) (e.g., a hand towel, a cleaning implement, etc.) from base hook 1702, including, without limitation, when device 1700 is attached to supportive structure 104 above ground surface 412 (e.g., as shown and described above with reference to FIG. 11).

Some embodiments of the devices shown and described above with reference to FIGS. 1-17 also include an antimicrobial coating 490. In those device embodiments including antimicrobial coating 490, antimicrobial coating 490 is applied to an exterior 120 facing surface of at least a portion of least one of: the container 106, the pump assembly 124, the at least one hanger arm 126, the brace 206, the brace bumper 207, the cross-piece 210, the cross-piece bumper 212, the hook 402, the bumper 132, the hook pad 502, the shank pivot point 907, the pin head 911, the flange 915, the lock mechanism 918, the pin head 1011, the flange 1015, the locking mechanism 1018, the first pin head 1111, the first flange 1115, the coupling pivot point 1122, the coupling lock 1124, the second pin head 1164, the second flange 1171, the second arm section pivot point 1172, the lower sleeve 1202, the lower sleeve lock mechanism 1210, the upper sleeve 1216, the upper sleeve lock mechanism 1230, the base extension 1302, the drawer 1310, the drawer 1410, the drawer grip 1358, the under-base cavity 1304, the under-base cavity 1404, the under-base cavity 1518, the cover 1604, the cover grip 1610, the third hanger arm 1516, and the base hook 1702. In some other embodiments, the device further includes antimicrobial coating 490 applied to surfaces of the device other than and/or in addition to those listed above, and which are subject to undesired microbial growth (e.g., bacteria, fungi, algae, viruses, mold, mildew, and the like). In those devices which include antimicrobial coating 490, the undesired microbial growth is at least one of prevented and substantially slowed by the presence of antimicrobial coating 490. Further embodiments of the above-described devices further include antimicrobial agents impregnated into the material(s) of construction of one or more components and/or portions of the device(s), either instead of or in addition to antimicrobial coating 490 applied to surface(s) thereof.

Figure 18:
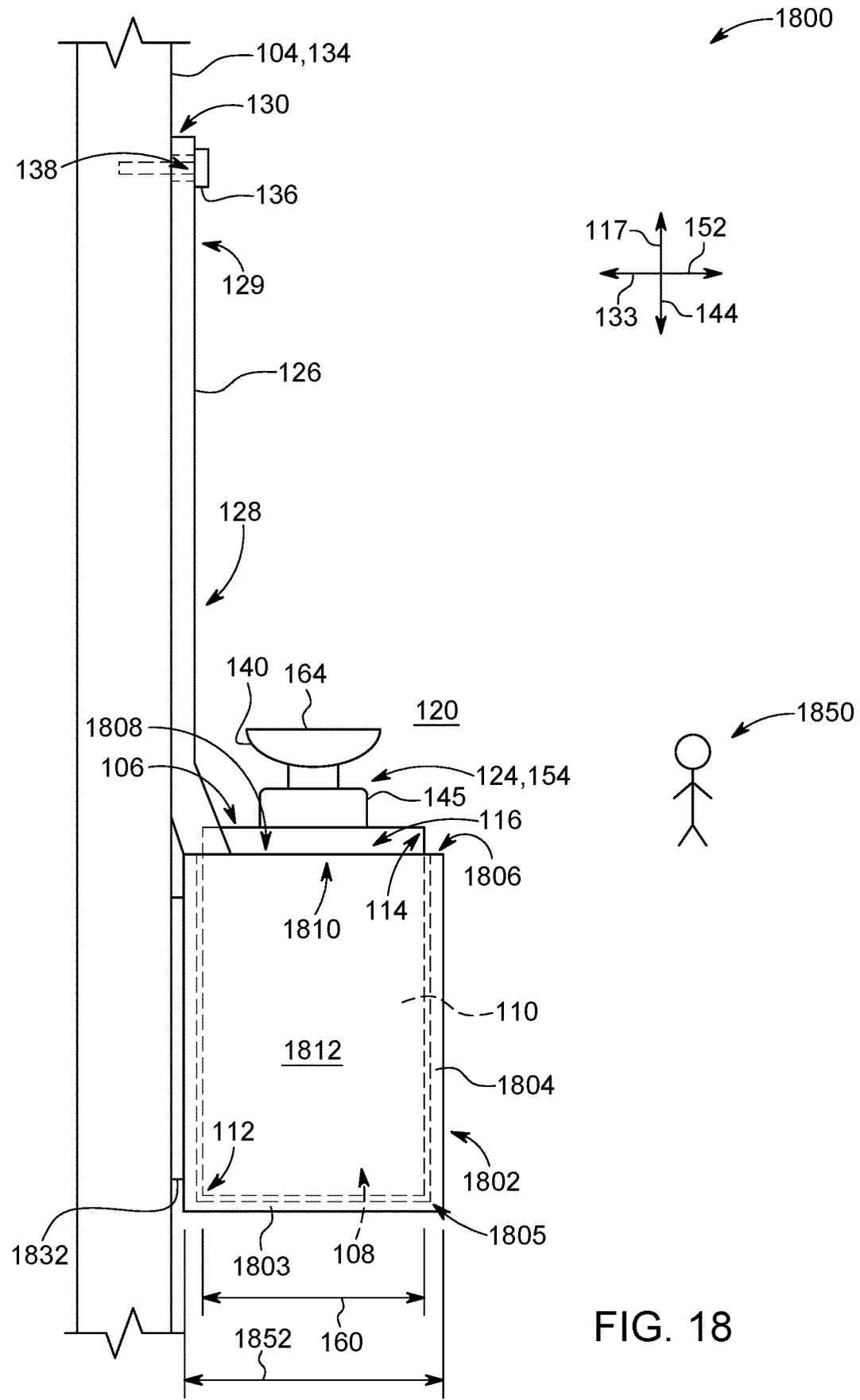
FIG. 18 is a side-view diagram of an embodiment of a system for containing and dispensing a liquid.

FIG. 18 is a side-view diagram of an embodiment of a system (e.g., a system 1800) for containing and dispensing a liquid 102. System 1800 is alternately attachable to and removable from a supportive structure 104 including, for example and without limitation, a substantially vertical surface 134 such as a wall. System 1800 includes a basket 1802. Basket 1802 includes a basket base 1803 and at least one basket side wall 1804. In the embodiment shown in FIG. 18, basket 1802 is substantially cubic in shape and thus includes four basket side walls 1804. In other embodiments, not shown, basket 1802 is circularly cylindrically-shaped or ellipsoidal cylindrically-shaped and thus includes one basket side wall 1804, with basket base 1803 having one side defined by a circumference. In still other embodiments, not shown, basket 1802 has greater than four basket side walls 1804 corresponding to greater than four sides of basket base 1803 (e.g., pentagonal or greater polygonally-shaped basket bases 1803).

Basket side wall 1804 includes a basket base edge 1805 coupled to the basket base 1803. Basket side wall 1804 also includes a basket top edge 1806 positioned opposite basket base edge 1805. Basket top edge 1806 defines an at least partially open basket top 1808 opposite basket base 1803. Basket base 1803 and the at least one basket side wall 1804 extend generally upward 117 from basket base 1803 to define a basket cavity 1812 of the basket 1802 having a predetermined volume. Volume of basket 1802 is thus based on the various dimensions of basket base 1803 and the at least one basket side wall 1804. Basket top 1808 includes a basket opening 1810 defined therein. Basket opening 1810 provides and facilitates access from an exterior 120 of basket 1802 to the basket cavity 1812 of basket 1802. Basket cavity 1812 is, therefore, defined by basket base 1803, the at least one basket side wall 1804, and the at least partially open basket top 1808.

System 1800 also includes at least one container 106 removably coupled to basket 1802 to facilitate nesting therein. Thus, container 106 is selectively inserted and removed into and out of, respectively, from basket 1802 by a user 1850 of system 1800. As shown and described above with reference to FIG. 1, container 106 includes a container base 108 and at least one container side wall 110. In the embodiment shown in FIG. 18, container 106 is substantially cubic in shape and thus includes four container side walls 110, with container base 108 having four sides. In other embodiments, not shown, container 106 is circularly cylindrically-shaped or ellipsoidal cylindrically-shaped and thus includes one container side wall 110, with container base 108 having one side defined by a circumference. In still other embodiments, not shown, container 106 has greater than four container side walls 110 corresponding to greater than four sides of container base 108 (e.g., pentagonal or greater polygonally-shaped container bases 108).

Container side wall 110 includes a base edge 112 coupled to container base 108. Container side wall 110 also includes a top edge 114 positioned opposite base edge 112. Top edge 114 defines an at least partially open container top 116 opposite container base 108. Container base 108 and the at least one container side wall 110 extend generally upward 117 from container base 108 to define a container cavity of the container 106 having a predetermined volume. Volume of container 106 is thus based on the various dimensions of container base 108 and the at least one container side wall 110. Container top 116 includes a container opening 118 defined therein. Container opening 118 provides and facilitates access from an exterior 120 of container 106 to an interior cavity 122 of container 106. Interior cavity 122 is, therefore, defined by container base 108, the at least one container side wall 110, and the at least partially open container top 116.

System 1800 also includes a pump assembly 124 coupled to container top 116, substantially as shown and described above with reference to FIG. 1. In the embodiment shown in FIG. 18, pump assembly 124 is removably coupled to container top 116 as, for example, through screw threads or via a snap-fitting. In other embodiments, not shown, pump assembly 124 is not removably coupled to container top 116. Instead, in such other embodiments, at least a portion of pump assembly 124 is integrally formed with container top 116. Also, container top 116 in the embodiment shown in FIG. 18 is integrally formed with container side wall 110 and container base 108 and, thus, container 106 is one piece. In other embodiments, not shown, container top 116 is not integrally formed with container side wall 110 and container base 108. In such other embodiments, container top 116 is removably coupled to the at least one container side wall 110 as, for example, through screw threads or via a snap-fitting. Also, in the embodiment shown in FIG. 18, pump assembly 124 extends through container opening 118 into interior cavity 122.

System 1800 further includes at least one hanger arm 126 coupled to basket 1802. The at least one hanger arm 126 extends distally from the basket 1802. In one embodiment, the at least one hanger arm 126 extends generally upward 117 from basket 1802. In the embodiment shown in FIG. 18, hanger arm 126 includes a first section 128 proximate basket 1802. Hanger arm 126 also includes a second section 129 positioned adjacent first section 128. Second section 129 is distal basket 1802 and includes a distal end 130. Also, in the embodiment shown in FIG. 18, first section 128 and second section 129 are integrally formed into a one-piece hanger arm 126. In other embodiments, not shown, hanger arm 126 is not integrally formed as one piece, but rather is formed from at least two pieces including first section 128 and second section 129. Further, in the embodiment shown in FIG. 18, hanger arm 126, basket top 1808, the at least one basket side wall 1804, and basket base 1803 are integrally formed as one piece. In other embodiments, not shown, hanger arm 126 is not integrally formed with basket top 1808, the at least one basket side wall 1804, and basket base 1803. In such other embodiments, the at least one hanger arm 126 is removably coupled to at least one of basket top 1808, basket side wall 1804, and basket base 1803, as, for example, through a snap-fit mechanism. In still other embodiments, not shown, at least one hanger arm 126 is non-removably secured to at least one of basket top 1808, basket side wall 1804, and basket base 1803. System 1800 further includes at least one bumper 1832 coupled to at least a portion of a rearward 133 facing portion of at least one of basket 1802 and the at least one hanger arm 126. In other embodiments, not shown, system 1800 does not include bumper 1832.

In the embodiment shown in FIG. 18, and substantially as shown and described above with reference to FIG. 1, pump assembly 124 includes a lid 145 coupled to container top 116. Lid 145 includes a lid opening 139 defined therein which provides and facilitates access from exterior 120 of container 106 to interior cavity 122 of container 106 when lid 145 is coupled to container top 116. Pump assembly 124 also includes a dispenser 140 including a dispenser opening 141 defined therein. Pump assembly 124 further includes a first tubular extension 142 slidingly coupled to lid 145 through the lid opening 139. First tubular extension 142 is further coupled to dispenser 140. First tubular extension 142 extends generally downward 144 from dispenser 140 to lid 145. Lid 145 and dispenser 140 are spaced apart by a predetermined, non-zero-valued distance defined by a length of the first tubular extension 142. First tubular extension 142 includes a first tube section 143 that is generally aligned with dispenser opening 141.

Pump assembly 124 also includes a second tubular extension 146 coupled to the first tubular extension 142. Second tubular extension 146 includes a second tube section 147 that is aligned with first tube section 143. In the embodiment shown in FIG. 18, first tubular extension 142 and second tubular extension 146 are integrally formed as one piece, with the second tubular extension 146 extending generally downward 144 from container top 116 into interior cavity 122 to a predetermined non-zero-valued distance from the container base 108. In other embodiments, not shown, first tubular extension 142 and second tubular extension 146 are not integrally formed as one piece. Instead, in such other embodiments, first tubular extension 142 is slidingly coupled to both lid 145 and to second tubular extension 146, while second tubular extension 146 is securely and non-slidingly coupled to at least one of lid 145 and container top 116.

As shown in FIG. 18, pump assembly 124 of system 1800 is embodied in a dish-top pump 154. Dish-top pump 154 includes lid 145 coupled to container top 116 as described above. Dispenser 140 of dish-top pump 154 includes a dish 156 having dispenser opening 141 defined in a bottom 162 of dish 156 opposite a top 164 of dish 156. Other types of dispensers 140 other than dish-top pump 154 are employed in system 1800 in addition to or instead of dish-top pump 154. Referring now to FIG. 3, for example and without limitation, an alternative embodiment of system 1800 includes pump assembly 124 having dispenser 140 embodied in a faucet-top pump 302. Generally, pump assembly 124 retains common features described above with reference to FIG. 18 and system 1800, except for the particular form taken by dispenser 140 (e.g., dish-top pump 154 versus faucet-top pump 302).

A person having ordinary skill in the art will recognize and appreciate that the disclosed devices and systems readily employ numerous types of pumps to accomplish the functionality described herein, including, without limitation, manually-operated pumps such as those illustrated in FIGS. 1, 3, and 18, but also pumps that employ electromechanical (e.g., motors) and other components (e.g., vacuum, hydraulic) that assist user 1850 of system 1800 to remove a desired amount of liquid from interior cavity 122 of container 106 to exterior 120. Such assistive components for pumping liquid from container 106 are desirable in several contexts, including, without limitation, where system 1800 and the various other embodiments described below are used by individuals having various handicaps and/or injuries that impede manual dexterity and/or strength.

Further, as shown in FIG. 18, container top 116 is embodied in a partially open container top 116. As such, container opening 118 has an opening size 158 that is less than a container width 160 of the container 106. In those embodiments in which container 106 is embodied in a circular or ellipsoidal cylindrically-shaped container 106, container width 160 is defined as a container diameter 203 (e.g., as shown and described below with reference to FIG. 19). Likewise, container width 160 is less than a basket width 1852 to provide and facilitate user 1850 of system 1800 having the ability to selectively and alternately insert and remove the at least one container 106 into and out of, respectively, basket 1802.

Lid 145 covers the container opening 118 of container 106. User 1850 couples lid 145 to container opening 118 to cover container opening 118 during use and/or storage of system 1800. Also, in use of system 1800, lid 145 is removed from container opening 118 when user 1850 desires to add more liquid 102 to container 106, replace the liquid 102 in container 106 with a different liquid 102, and/or wash the interior cavity 122 of container 106. In other embodiments, not shown, container 106 includes a level sensor which provides and facilitates the user 1850 having the ability to determine and/or estimate a present volume of liquid 102 in container 106 without having to open lid 145. Level sensor includes analog and/or digital components which sense the level of liquid 102 in interior cavity 122 and provide a visual indication (e.g., light changing from first color indicating the volume of liquid 102 being greater than a predetermined volume to a second color indicating the volume of liquid 102 being less than or equal to the predetermined volume) to the user 1850 containing this information. In still other embodiments, system 1800 includes a communication subsystem which transmits (e.g., by a wired and/or wireless data communication protocol) the information about the present level and/or the present volume of liquid 102 in interior cavity 122 of container 106 to a location distal container 106 (e.g., to an application, i.e., "app", of a smartphone of the user 1850). Furthermore, communication subsystem, in some system embodiments, communicates with a vendor to place an order for user 1850 to at least one of purchase, initiate shipping, initiate delivery, and receive additional volume(s) of liquid(s) 102 sufficient to refill container 106 when the present volume and/or the present level of liquid 102 in interior cavity 122 becomes less than or equal to the predetermined volume. In yet other embodiments, not shown, container 106 and/or pump assembly 124 includes a counter sensor (e.g., an accelerometer) which counts the number of times user 1850 pumps the pump assembly 124 (e.g., applies the downward 144 force 148 thereto). Through correlation of the factional volume 125 per application of downward 144 force 148 by user 1850, counter sensor notifies user 150 upon the number of pumps reaching a number that is representative of a predetermined remaining volume of liquid 102 in interior cavity 122 (e.g., the fractional volume 125 being less than the maximum volume of liquid 102 that is containable by container 106). This notification includes information, and the notification is transmitted to and/or visualized by user 1850 through one or more of the communication methods described above. User 1850 is also provided with the ability to determine the present volume of liquid 102 in interior cavity 122 of container 106 through utilizing an at least partially transparent material of construction for at least a portion of container side wall 110, container top 116, and/or basket side wall 1804.

Also, in the embodiment shown in FIG. 18, first tubular extension 142 of pump assembly 124 includes a first tube section 143 that is generally aligned with dispenser opening 141 to provide and facilitate access to the interior cavity 122 through the dispenser opening 141 (shown in FIG. 1). Further, in embodiments of system 1800 where first tubular extension 142 and second tubular extension 146 are continuous and substantially formed as a one-piece construction, a bottom 144 end of second tubular extension 146 is positioned above 117 base 108 of container 106 by a distance that is greater than or equal to a length of first tubular extension 142 slidingly coupled to lid 145 through the lid opening 139 (e.g., the distance between top 117 of lid 145 and bottom 144 of dish 156, as shown in FIG. 1). In other embodiments, not shown, second tubular extension 146 and first tubular extension 142 are not continuously formed as a one-piece construction. In such other embodiments, a top 117 end of second tubular extension 146 is nested within a bottom 144 end of first tubular extension 142 and first tubular extension 142 is slidable over the top 117 end of second tubular extension 146. Second tubular extension 146 in these other embodiments is coupled to lid 145 at lid opening 139. As such, the bottom 144 end of second tubular extension 146 is positioned above 117 base 108 by a distance greater than zero, but need not be positioned above 117 base 108 by a distance that is greater than or equal to the length of first tubular extension 142. Further, in such other embodiments described above, pump assembly 124 is able to access liquid 102 from interior cavity 122 down to a lower level and to a lower volume relative to embodiments of the system having the first tubular extension 142 continuously formed with the second tubular extension 146 as a one-piece construction.

Dispenser 140 of pump assembly 124 receives a force 148 having a downward 144 force vector component from user 1850 (substantially as shown and described above with reference to FIG. 1). In the example embodiment, during operation, user 1850 is positioned generally frontward 152 of system 1800 and supportive structure 104. Application by user 1850 of the downward 144 force 148 vector component provides and facilitates pump assembly 124 having the ability to transfer the fractional volume 125 of liquid 102 from interior cavity 122 of container 106 to the exterior 120. By this pumping action of user 1850 manipulating pump assembly 124 in the aforementioned manner, the fractional volume 125 is thus transferred generally upward 117 from interior cavity 122 of container 106 through the second tubular extension 146, the first tubular extension 142, and the dispenser opening 141. In one use case in particular, user 1850 applies the downward 114 force 148 to pump assembly 124 with his or her hand (not shown) holding a fabric cloth or paper towel, the cloth or towel at least partially covering the dispenser opening 141. The fractional volume 125 is thereby transferred from interior cavity 122 to the cloth or the towel, and user 1850 then uses the wetted cloth or towel as desired at a location or locations distal pump assembly 124 (e.g., on his or her body and/or on surfaces located in the vicinity of or distal system 1800). In another example use case, user 1850 of system 1800 applies the fractional volume 125 of liquid 102 directly to the hand (e.g., hand sanitizer) and applies the downward 144 force 148 to pump assembly 124 without also holding a cloth or towel. In yet another use case, pump assembly 124 dispenses fractional volume 125 of liquid 102 as a spray and/or mist (e.g., an air freshener).

In each of the example use cases provided above, and in many others that a person having ordinary skill in the art will recognize and appreciate, user 1850 repeats the application of the downward 144 force 148 to pump assembly 124 if desired to obtained the desired amount of liquid 102 transfer from interior cavity 122 to exterior 120 of system 1800. To reset the pump assembly 124 to its fully upright 117 position after user 1850 applies the downward 144 force 148 to pump assembly 124, pump assembly 124 includes a spring (not shown) positioned proximate dispenser 140 and/or lid 145. Thus, a restoring force of the compressed spring returns the pump assembly 124 to its fully upright 117 position, whereby pump assembly 124 is again ready to dispense an additional aliquot of the fractional volume 125 of liquid 102. In the embodiments of the systems (e.g., system 1800) including dish-top pump 154, the dispenser 140 thereof contains the fractional volume 125 of liquid 102, where, for example, user 1850 can utilize a cloth or towel to wick the factional volume 125 out of the dish 156.

In the systems shown and described herein, bumper 1832 provides several benefits during use. Bumper 1832 is formed of a material that is generally softer and more pliable than materials of construction of the rest of the device (e.g., system 1800). For example, and without limitation, bumper 1832 protects substantially vertical surface 134 (e.g., wall) from wear due to repeated applications of force 148 by user

1850. Also, for example, bumper 1832 mitigates undesired movements of the system (e.g., system 1800) before, during, and after application of force 148 by user 1850. Bumper 1832 further provide additional benefits in the various embodiments of the devices described herein, of which persons having ordinary skill in the art will recognize and appreciate.

Furthermore, the systems shown and described herein (e.g., system 1800) are removably attached to supportive structure 104 through the alternate attachment to and removal of the second portion 129 of the at least one hanger arm 126 (including distal end 130) from the supportive structure 104. In the embodiment shown in FIG. 18, for example, at least one fastener hole 138 is defined (e.g., formed) through at least one portion of hanger arm 126 (e.g., in at least one location on second portion 129 proximate distal end 130). A fastener 136 is selectively insertable and removable through and from, respectively, the fastener hole 138 by user 1850. Thus, fastener 136 and fastener hole 138 provides and facilitates user 1850 having the ability to alternately and selectively attach and remove device 100 to and from, respectively, supportive structure 104.

Figure 19:
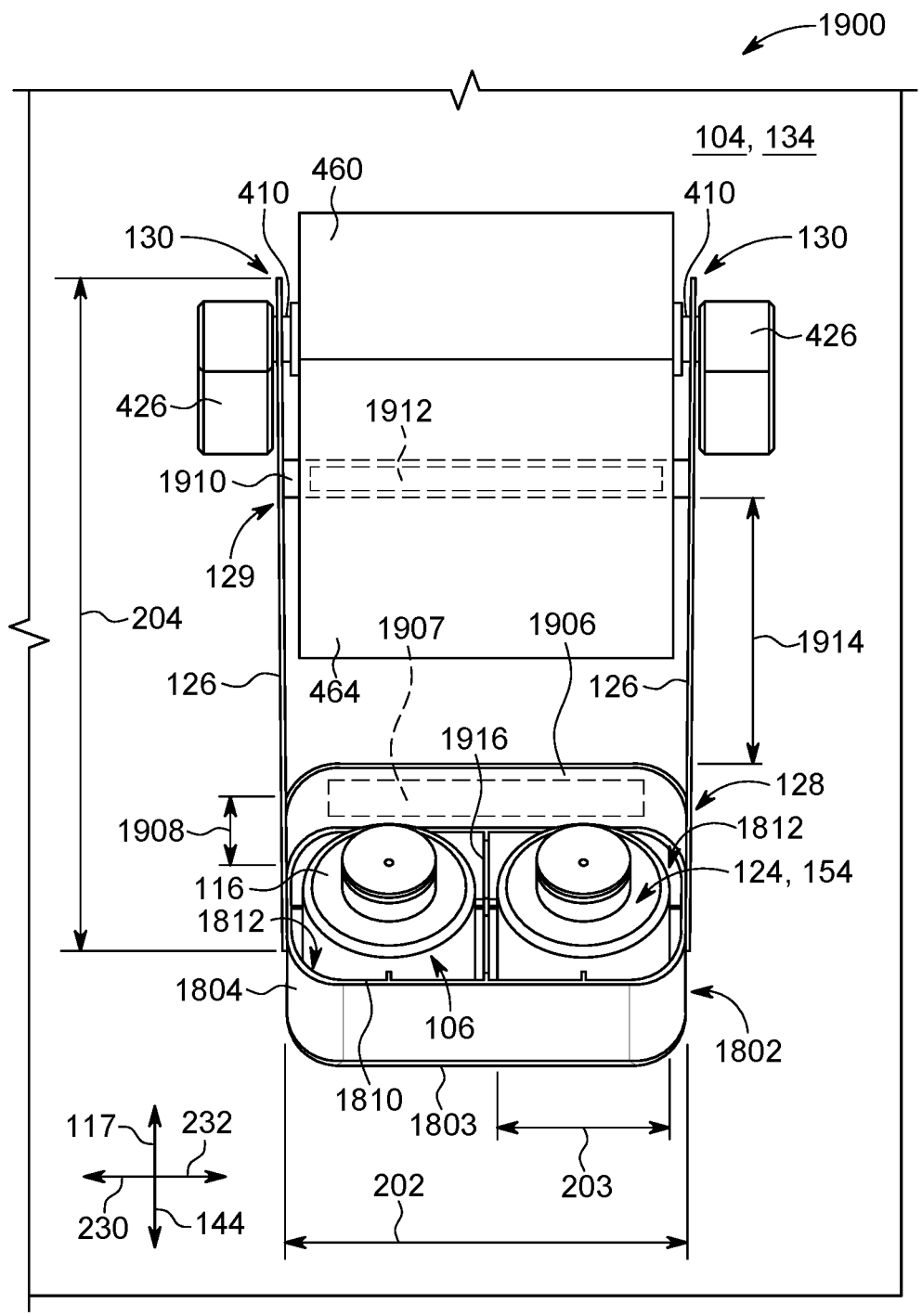
FIG. 19 is a front-view diagram of an alternative embodiment of a system for containing and dispensing a liquid.

FIG. 19 is a front-view diagram of an alternative embodiment of a system (e.g., a system 1900) for containing and dispensing a liquid. System 1900 is alternately attachable to and removable from supportive structure 104. System 1900 includes basket 1802 and at least one container 106, as shown and described above with reference to FIG. 18. As compared to system 1800, system 1900 includes a plurality of containers 106 (e.g., two containers 106), and each container 106 of the plurality of containers 106 is circularly cylindrically-shaped. Further, in system 1900, each container 106 of the two containers 106 has a container diameter 203 that is less than the basket width 1852. Also, in the embodiment shown in FIG. 19, container top 116 is fully open, and container opening 118 has opening size 158 that is substantially equal to the container width 160 (or, in circular or ellipsoidal cylindrically-shaped embodiments of container 106, the container diameter 203). Thus, in embodiments such as system 1800 where container top 116 is fully open, interior cavity 122 is further defined by pump assembly 124.

In the embodiment shown in FIG. 19, system 1900 includes two hanger arms 126 spaced apart by a lateral distance 202. Each hanger arm 126 of the two hanger arms 126 in system 1900 extends generally upward 117 from the basket 1802 by an arm distance 204. System 1900 also includes a brace 1906 coupled to and extending laterally between each hanger arm 126 of the two hanger arms 126 proximate the first sections 128 thereof. Brace 1906 is further coupled to basket 1802 proximate basket top 1808 at a rearward 133 facing side thereof. Brace 1906 extends generally upward 117 from basket top 1808 by a brace height 1908. In other embodiments, not shown, brace 1906 is not further coupled to basket 1802. In still other embodiments, not shown, system 1900 includes a plurality of braces 1906 coupled to and extending laterally between each hanger arm 126 of the two hanger arms 126 proximate the first sections 128 thereof. In such other embodiments having a plurality of braces 1906, one brace 1906 of the plurality of braces 1906 is, optionally, further coupled to basket 1802, as described above. Also, in the embodiment shown in FIG. 19, the brace height 1908 is less than or substantially equal to half the arm distance 204. In other embodiments, not shown, the brace height 1908 is greater than half the arm distance 204, including, for example, the brace height 1908 being substantially equal to the arm distance 204.

System 1900 also includes a brace bumper 1907 coupled to a rearward 133 side of brace 1906. In other embodiments, not shown, system 1900 does not include brace bumper 1907. Also, in the embodiment shown in FIG. 19, system 1900 further includes a cross-piece 1910 coupled to and extending laterally between each hanger arm 126 of the two hanger arms 126 proximate the second sections 129 thereof. In other embodiments, not shown, system 1900 does not include cross-piece 1910. In still other embodiments, not shown, system 1900 includes a plurality of cross-pieces 1910 coupled to and extending laterally between each hanger arm 126 of the two hanger arms 126 proximate the second sections 129 thereof. In embodiments having cross-piece 1910, system 1900 also includes a cross-piece bumper 1912 coupled to a rearward 133 facing portion of cross-piece 1910. In other embodiments, not shown, system 1900 does not include cross-piece bumper 1912. Furthermore, in the embodiment shown in FIG. 19, cross-piece 1910 is spaced from the brace 1906 by a vertical distance 1914.

System 1900 is removably attached to supportive structure 104 (e.g., elongate structure 110) through use of hook 402 on each hanger arm 126 of the two hanger arms 126, substantially as shown and described above with reference to FIG. 4. Moreover, in the embodiment shown in FIG. 19, brace 1906 and cross-piece 1910 provide further structural support and rigidity to the two hanger arms 126 of system 1900. Brace bumper 1907 and cross-piece bumper 1912 provide substantially similar benefits to system 1900 as bumper 1832 provides to system 1800, as shown and described above with reference to FIG. 18. Brace 1906 provides further benefits to user 1850 during operation of system 1900. For example, and without limitation, brace 1906 functions as a splash guard in system 1900. Thus, brace 1906 prevents liquid 102 from contacting, for example, substantially vertical surface 134 to the rear 133 of pump assembly 124 on account of user 1850 inadvertently spilling, spraying, splashing, and/or dripping liquid 102 from dish 156 of dish-top pump 154 during and/or after application of the downward 144 force 148 to pump assembly 124. In one embodiment, not illustrated, the brace 1906 is coupled to the two hanger arms 124, but is not also coupled to the basket 1802. In yet another embodiment, not shown, a splash guard may be coupled to the basket 1802 rearward 133 of the pump assembly 124, extends upward from the basket 1802, but is not also coupled to either or both of the two hanger arms 126.

FIG. 20 is a side-view diagram of another embodiment of a system (e.g., a system 2000) for containing and dispensing a liquid. System 2000 includes basket 1802, container 106, pump assembly 124 (embodied in dish-top pump 154), and at least one hanger arm 126, as shown and described above with reference to FIGS. 18 and 19. Similarly, system 2000 is alternately attachable to and removable from supportive structure 104. In this embodiment, the distal end 130 of hanger arm 126 is formed as a generally downward 144 facing hook 402. Hook 402 includes a shank 406 spaced apart from at least a portion of the second section 129 of hanger arm 126. Shank 406 extends generally downward 144 from an upper 117 extent 408 (an uppermost 117 upward 117 facing surface of the hanger arm 126 of the distal end 130). The space defined by the shank 406 and the second section 129 defines a slot 404 therebetween. In the embodiment shown in FIG. 20, the at least one hanger arm 126 is formed as an arcuate hanger arm 126. Arcuate hanger arm 126 includes a frontward 152 facing convex side 418 and a rearward 133 facing concave side 420. In other embodiments, not shown, arcuate hanger arm 126 has the opposite curvature. In such other embodiments, convex side 418 is the rearward 133 facing side and concave side 420 is the frontward 152 facing side.

Also, in the embodiment shown in FIG. 20, the supportive structure 104 includes an elongate structure 410 positioned substantially parallel to a ground surface 412. For example, and without limitation, elongate structure 410 is embodied in a paper towel roll holder rod 413 and ground surface 412 is embodied in a floor 415 in a home, business, or industrial structure. Referring again to FIGS. 5 and 6, for example and without limitation, elongate structure 410 has a width 512 that is less than or substantially equal to an effective slot width 510 of the slot 404. Furthermore, as shown in FIGS. 5, 6, and 7, the elongate structure 410 includes at least one of a rod 514 having a circular cross-section, a rod having an elliptical cross-section, a bar 702 having a square cross-section, a bar having a rectangular cross-section, a bar having a triangular cross-section, and a bar having a polygon-shaped cross-section, the polygon having greater than four sides. Depending upon particular shapes of at least one of the supportive structure 104 and the elongate structure 410, the shape of the hook 402 is correspondingly formed to conform to the particular shape to facilitate a secure, yet removable attachment of system 2000. Moreover, system 2000 further includes a hook pad 502 coupled to a downward 144 facing surface of the hook 402, substantially as shown in FIGS. 5 and 6. In other embodiments, not shown, system 2000 does not include hook pad 502.

Further, in the embodiment shown in FIG. 4, at least a portion of the second section 129, the distal end 130, and the shank 406 define an arcuate hook 402 structure. The arcuate hook 402 structure is intended for user 150 to fit around upper 117 portion(s) of elongate structure(s) 410 (e.g., a rod) having at least one of a circular cross-section and an elliptical cross-section. In other embodiments (e.g., as shown and described below with reference to FIG. 7), hook 402 is not arcuately formed, but rather is formed with shank 406 having substantially square corners and in shape(s) intended for user 150 to fit around upper 117 portion(s) of elongate structure(s) 410 (e.g., a bar) having at least one of a square cross-section and a rectangular cross-section. In still other embodiments, not shown, hook 402 is formed with a triangularly and/or polygonally-shaped (greater than four sides) shaped shank 406 and in shape(s) intended for user 150 to fit around upper 117 portion(s) of elongate structure(s) 410 (e.g., a bar) having at least one of a triangular cross-section and a polygonal cross-section having greater than four sides.

Further, in the embodiments shown in FIGS. 5 and 20, shank 406 is positioned frontward 152 relative to the second section 129 in system 2000. In other embodiments, such as is shown in FIG. 6, shank 406 has the opposite positioning, with shank 406 being positioned rearward 133 relative to the second section 129. Moreover, in the embodiment shown in FIG. 20, the supportive structure 104 also includes at least one offset structure 426 coupled to the substantially vertical surface 134 and extending frontward 152 therefrom. The elongate structure 410 is coupled to the at least one offset structure 426 to provide and facilitate a spacing of the elongate structure 410 from the substantially vertical surface 134 by a predetermined offset distance 432.

Also, in the embodiment illustrated in FIG. 20, the first section 128 includes an arm axis 437 and the basket 1802 includes a basket axis 2039. In this embodiment, the at least one hanger arm 126 is coupled to basket 1802 with arm axis 437 and basket axis 2039 oriented at a coupling angle 2040 that is greater than zero degrees and less than about forty-five degrees. In other embodiments, such as system 1800 shown and described above with reference to FIG. 18, coupling angle 2040 (not shown in FIG. 18) is substantially equal to zero degrees (e.g., the at least one hanger arm 126 is straight, rather than arcuately curved). In still other embodiments, not shown, coupling angle 2040 is greater than zero degrees and less than about ninety degrees.

Figure 21:
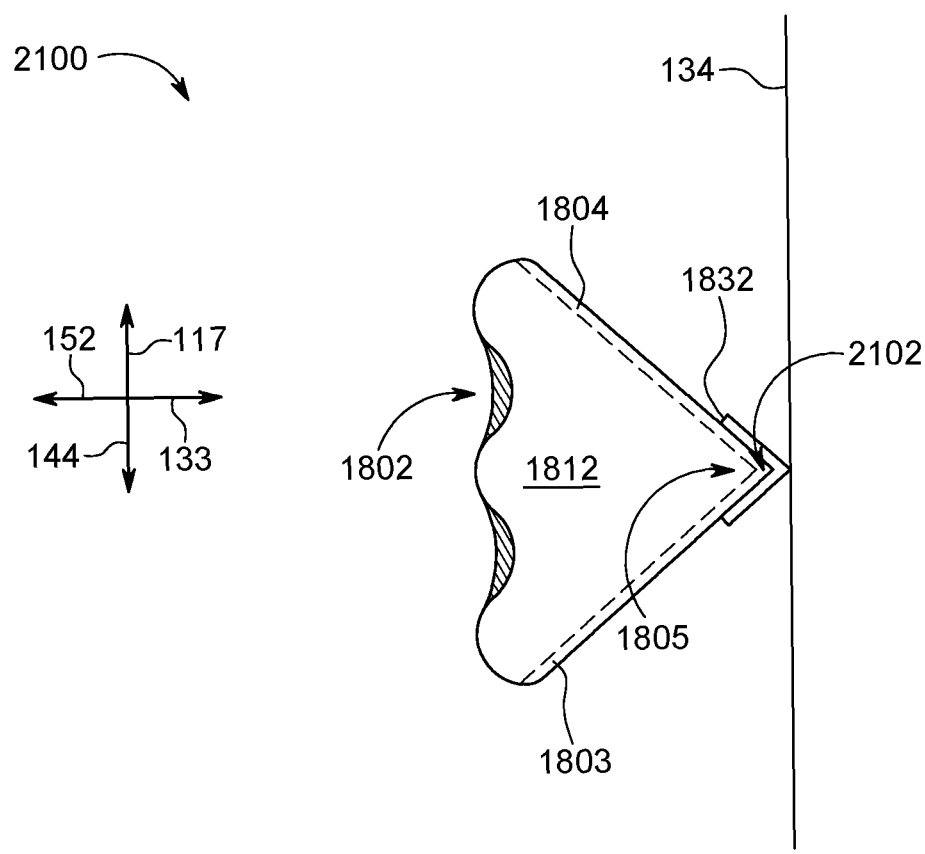
FIG. 21 is a side-view diagram of an alternative embodiment of a portion of the basket shown in FIG. 20.

As shown in FIG. 20, a rearward 133 facing portion of basket 1802 includes an arcuate fillet 2038. Arcuate fillet 2038 is formed at a juncture of a rearward 133 facing portion of the basket base 1803 and a rearward 133 facing portion of the at least one basket side wall 1804. The arcuate fillet 2038 is thus concavely formed with respect to the basket cavity 1812 of the basket 1802. In the embodiment shown in FIG. 20, system 2000 further includes bumper 1832 coupled to an exterior 120 rearward 133 facing surface of the arcuate fillet 2038. In other embodiments (e.g., as shown in FIG. 21), the systems shown and described herein do not include the arcuate fillet 2038. For example, in a system 2100, a rearward 133 facing portion of basket 1802 includes a substantially square corner 2102 formed at a juncture of a rearward 133 facing portion of the basket base 1803 and a rearward 133 facing portion of the at least one basket side wall 1804. When hanging from the elongate structure 410, system 2100, for example, further contacts the substantially vertical surface 134 at the square corner 2102.

Moreover, in system 2100, square corner 2102 includes a square corner bumper 1832 coupled thereto, substantially as shown and described above with reference to bumper 1832 coupled to arcuate fillet 2038 (e.g., FIG. 20).

System 2000, and other embodiments of the systems described herein which include hook 402, hangs from elongate structure 410 through removable coupling of hook 402 to elongate structure 410 through the slot 404. Depending upon particular shapes of at least one of the supportive structure 104 and the elongate structure 410 (e.g., rod as compared to bar, as shown and described above), the shape of hook 402 is correspondingly formed to conform to the particular shape to facilitate a secure, yet removable attachment of system 2000. In the systems (e.g., system 2000) shown and described herein, hook 402 includes hook pad 502 as shown and described above with reference to FIG. 5). Hook pad 502 is formed of a softer and generally more pliable material of construction than the rest of hook 402. For example, and without limitation, hook pad 502 protects elongate structure 410 (e.g., bath tissue holder rod 413 holding a bath tissue roll 460, where bath tissue holder rod 413 is inserted through a center cavity 462 of bath tissue roll 460) from wear due to repeated attachment and removal of system 2000 to and from, respectively, elongate structure 410 by user 1850. Also, for example, hook pad 502 mitigates undesired movements of the system (e.g., system 2000) during use thereof (e.g., before, during, and/or after application of force 148 by user 1850 to pump assembly 124 and/or prior to, during, and/or after user 1850 removes a sheet 464 from bath tissue roll 460). Hook pad 502 further provide additional benefits in the various embodiments of the devices described herein, of which persons having ordinary skill in the art will recognize and appreciate.

When hanging from elongate structure 410, system 2000 exerts upon elongate structure 410 a gravity force 414 having a downward 144 force vector component. In addition to the gravity force 414, when hanging from elongate structure 410, system 2000 further exerts a lateral force 421 upon elongate structure 410. Lateral force 421 includes downward 144 and rearward 133 force vector components. The coupling of the hook 402 to the elongate structure 410 defines a fulcrum 422 of system 2000, and the hanger arm 126 (e.g., the arcuate hanger arm 126 in system 2000) generally defines a pivot arm 424 of system 2000.

Also, in the embodiment shown in FIG. 20, the at least one offset structure 426 provides and facilitates system 2000 (e.g., when hanging from elongate structure 410) having the ability to further exert a contact force 434 to at least one of a contact point 436 and a contact region 436 upon the substantially vertical surface 134. The removable attachment 428 of offset structure 426 to the substantially vertical surface 134 is sufficiently load-bearing to support system 2000 hanging therefrom, including system 2000 having one or more containers 106 filled to capacity with liquid 102. The contact force 434 has at least one of rearward 133 force vector component and a downward 144 force vector component. The at least one hanger arm 126 extending distally (e.g., generally upward) from the basket 1802 facilitates providing a cancellation of torque when the user 1850 applies force 148 on the pump assembly 124.

Furthermore, as shown in FIG. 20, when hanging from elongate structure 410, system 2000 contacts the substantially vertical surface 134 at a rearward 133 facing portion of the basket 1802. In combination, gravity force 414 and lateral force 434 provide and facilitate system 2000 having the ability to remain securely, yet removably attached to supportive structure 104 (e.g., elongate structure 410) including before, during, and after application of force 148 by user 1850 to pump assembly 124. Inclusion of at least one of bumper 1832 and hook pad 502 in systems described herein (e.g., system 2000) further provides structural stability when the systems are hanging from elongate structure 410 and being manipulated by user 1850. This structural stability is provided by, for example and without limitation, at least one of bumper 1832 and hook pad 502 damping forces experienced during use and which have force vector components in at least one direction (e.g., at least one of frontward 152, rearward 133, upward 117, downward 144, leftward 230, and rightward 232).

Gravity force 414 and lateral force 434 further provide and facilitates system 2000 having the ability to remain securely, yet removably attached to supportive structure 104 including before, during, and/or after user 1850 operates pump assembly 124, manipulates container 106 (e.g., to fill it with liquid, to remove it from basket 1802, and/or to check the remaining volume of liquid therein), handles bath tissue roll 460 to remove at least one sheet 464 therefrom, and/or manipulates various other features of the systems described herein (e.g., adjustable features, including, without limitation, those shown and described herein with reference to FIGS. 9 and 22-24, and also, e.g., drawers, cavities, covers, and/or hooks including, without limitation, those shown and described below with reference to FIGS. 25-29). In other embodiments, not shown (e.g., embodiments not including at least one of bumper 1832 and hook pad 502), user 1850 affixes pads and other types of materials (e.g., materials that are softer and generally more pliable than the rest of basket 1802, hanger arm 126, and/or hook 402) to surface(s) of supportive structure 104 (e.g., elongate structure 410 and/or substantially vertical surface 134) where the systems described herein (e.g., system 2000) are expected to make contact with supportive structure 104 during use. For example, and without limitation, user 1850 couples at least one rubber pad (not shown) to substantially vertical surface 134 at the contact region 436 thereof.

Moreover, in the embodiment shown in FIG. 20, when system 2000 is hanging from elongate structure 410, system 2000 further contacts the substantially vertical surface 134 (e.g., at at least one of contact point 436 and contact region 436) at the arcuate fillet 2038, including, without limitation, arcuate fillet 2038 having bumper 1832 coupled thereto. Arcuate fillet 2038 provides and facilitates mitigation of wear to substantially vertical surface 134 on account of application of at least one of gravity force 414, and lateral force 434, and force 148. Inclusion of bumper 1832 coupled to arcuate fillet 2038 enhances the aforementioned wear-mitigative effect.

Another embodiment of the system shown and described above with reference to FIG. 20 includes shank 406 of hook 402 rotatably coupled to the second section 129 of the at least one hanger arm 126 (as shown and described above with reference to FIG. 9). The shank 406 is rotatably coupled to second section 129 proximate the distal end 130 of hanger arm 126. Shank 406 includes a shank axis 904, and second section 129 includes a second section axis 906. A shank angle 902 is defined by an angle of shank axis 904 relative to second section axis 906. Shank angle 902 is selectively adjustable by user 1850 of system 2000 by rotating (e.g., pivoting) shank 406 about a shank pivot point 907. Selectively adjusting shank angle 902 through rotation of shank 406 about shank pivot point 907 thereby provides and facilitates alternate increasing and decreasing of shank angle 902 by user 1850.

To provide and facilitate adjustment of shank angle 902 by user 1850, this embodiment of system 2000 includes a bore 908 defined through at least one of shank 406 and second section 129. This embodiment of system 2000 also includes a pivot pin 910 slidingly coupled to at least one of shank 406 and second section 129. This embodiment of system 2000 also includes a pivot pin 910 including a pin head 911 and a pin shaft 913. Pivot pin 910 is inserted through bore 908 from a first side 912 of distal end 130 toward a second side 914 of distal end. In other embodiments, not shown, pivot pin 910 is inserted through bore 908 from second side 914 toward first side 912. The pin shaft 913 has a width substantially equal to a width of bore 908. Pin head 911 has a width greater than the width of pin shaft 913 to prevent a complete travel of pin shaft 913 through bore 908. This embodiment of system 2000 further includes a flange 915 coupled to pin shaft 913 on one side thereof, for example and without limitation, proximate a surface of the second side 914. Flange 915 has a width that is greater than the width of bore 908.

Also, in embodiments of system 2000 including shank 406 of hook 402 rotatably coupled to the second section 129, shank angle 902 is securable in a substantially fixed position following adjustment of shank angle 902 by user 1850. To secure shank 406 and to fix shank angle 902 at the value (e.g., position of shank 406) selected by user 1850, this embodiment of system 2000 includes a lock mechanism 918 coupled to at least one of pin head 911 and flange 915. Lock mechanism 918 provides and facilitates user 1850 having the ability to selectively couple and decouple at least one of pin head 911 and flange 915 to and from at least one of first side 912 and second side 914. Moreover, adjustment of shank angle 902 provides and facilitates user 1850 having the ability to selectively adjust the effective slot width 510 of the slot 404 of hook 402.

Referring again to FIG. 9, the supportive structure 104 includes elongate structure 410 positioned substantially parallel to ground surface 412, not shown. Elongate structure 410 has a width 920 that is less than or substantially equal to the effective slot width 510 of slot 404. Thus, system 2000 is hangable from elongate structure 410 through a removable coupling of hook 402 to elongate structure 410 through the slot 404. Lock mechanism 918 present in embodiments of system 2000 including shank 406 of hook 402 rotatably coupled to the second section 129, provides and facilitates rotatable shank 406 having the ability to form a secure, but removable, load-bearing attachment of system 2000 from elongate structure 410. Lock mechanism 918 thereby prevents detachment of system 2000 from elongate structure 410 by reducing a probability of decoupling of hook 402 from elongate structure 410 (e.g., due to slippage and/or undesired rotation of shank 402 about shank pivot point 907). Furthermore, lock mechanism 918 provides and facilitates user 1850 having the ability to securely and conveniently accommodate varying widths 920 of different elongate structures 410.

In other embodiments, not shown, shank 406 is not rotatable about a shank pivot point 907, but rather is formed of a flexible material of construction. In such other embodiments, shank angle 902 of shank axis 904 relative to second section axis 906 is selectively adjustable to facilitate alternately increasing and decreasing the shank angle 902 and the effective slot width 510. The flexible material of construction of shank 406 is flexible enough to be manually manipulated by user 1850 in at least one direction (e.g., frontward 152, rearward 133, upward 1 17, downward 144, leftward 230, and rightward 232). Although the flexible material of construction of shank 406 in such other embodiments is manually manipulatable, it retains its shape and its load-bearing properties after being manipulated by user 1850. For example, and without limitation, user 1850 of such embodiments of system 2000 selectively adjusts the shank angle 902 by alternately flexing the shank 406 frontward 152 and rearward 133. Thus, the flexible material of construction of shank 406 provides and facilitates shank 406 having the ability to form a secure, but removable, load-bearing attachment of this embodiment of system 2000 from elongate structure 410. System 2000 having the flexible material of construction of shank 406 (e.g., instead of, or in addition to rotatable shank 406 and/or lock mechanism 918) thereby prevents detachment of such system embodiments from elongate structure 410 by reducing a probability of decoupling of hook 402 from elongate structure 410 (e.g., due to slippage, breakage, and/or undesired changes in shape and/or load-bearing properties of shank 402).

Furthermore, the flexible material of construction of shank 406 provides and facilitates user 150 having the ability to securely and conveniently accommodate varying widths 920 of different elongate structures 410. Flexible material of construction of shank 406 also provides and facilitates user 1850 having the ability to conform the shape of the hook 402 to varying shapes and widths 920 of different elongate structures 410. In other embodiments, not shown, at least one portion of the at least one hanger arm 126 other than or in addition to hook 402 is formed of the flexible material of construction to provide similar benefits to user 1850 of the systems (e.g., systems 2000) described herein. For example, and without limitation, in such other embodiments, at least one of first section 128 and second section 129 is formed of the flexible material of construction to provide and facilitate the user 1850 having the ability to selectively and alternately transition hanger arm 126 from a substantially straight and vertical hanger arm 126 (e.g., having an angle of arm axis 437 relative to second section axis 906 that is substantially equal to zero degrees, as shown in FIG. 18) to the arcuately curved hanger arm 126 (e.g., where an angle of arm axis 437 relative to second section axis is not substantially equal to zero degrees, as shown in FIG. 20).

In those system embodiments having shank angle 902 that is adjustable by user 1850, pin head 911 has a width that is greater than the width of pin shaft 913 to prevent a complete travel of pin shaft 913 through bore 908. As shown in FIG. 9, flange 915 has a width that is greater than the width of bore 908 in order to facilitate preventing detachment of the pivot pin 910 from the bore 908 when inserted therein. Thus, for example, and without limitation, a first end of pin shaft 913 (e.g., opposite a second end thereof to which pin head 911 is coupled to) is inserted through bore 908 from first side 912, and when so inserted, pin head 911 rests upon first side 912. Flange 915 is then coupled to the first end of pin shaft 913 such that flange 915 is positioned proximate second side 914. In the hook 402 shown in FIG. 9, both of flange 915 and pin head 911 are not further coupled to first side 912 and second side 914, respectively. In other hook 402 embodiments, not shown, at least one of flange 915 and pin head 911 is further coupled to at least one of first side 912 and second side 914, respectively. Thus, in the example embodiment, shank 406 is rotatably coupled to the second section 129 of hanger arm 126 proximate the distal end 130 thereof. For example, and without limitation, flange 915 is coupled to both the first end of the pin shaft 913 and the second side 914, where the second side 914 is defined and positioned on the shank 906. The pin head 91 1 rests upon, but is not coupled to, the first side 912, where the first side 912 is defined and positioned on the second section 129 proximate the distal end 130 thereof. Also, as shown in FIG. 9, shank 906 thus rotates about an axis defined by pin shaft 913 relative to distal end 130 of second section 129, and through a plurality of shank positions 930 (e.g., a first shank position 930a and a second shank position 930b).

Selective and alternating rotation (e.g., pivoting) of shank 906 by user 1850 provides and facilitates user 1850 having the ability to adjust (e.g., selectively and alternately increase and decrease) a shank angle 902 of a shank axis 904 relative to a second section axis 906, which thereby provides and facilitates user 1850 having the ability to adjust (e.g., selectively and alternately increase and decrease) the shank angle 902 through a plurality of values (e.g., a first shank angle 902a, and a second shank angle 902b having a value that is greater than the first shank angle 902a). As user 1850 adjusts shank angle 902 from the first shank angle value 902a to the second shank angle value 902a, the position of the shank axis 904 is likewise adjusted by user 1850 from a first shank axis 904a position to a second shank axis 904b position. Similarly, as user 1850 adjusts shank angle 902 from the first shank angle value 902a to the second shank angle value 902a, the position of shank 406 is adjusted by user 1850 from a first shank 406a position to a second shank 406b position that is different from the first shank 406a position.

System 2000 having rotatable shank 406 is hangable from elongate structure 410 through a removable coupling of hook 402 to elongate structure 410 through the slot 404. As described above, elongate structures 410 intended by user 1850 for use with the systems described herein include various shapes and sizes (e.g., widths 920, and lengths). In an example use case, user 1850 desires to transfer system 2000 having rotatable shank 906 from a first elongate structure 410a having a first width 920a to a second elongate structure 410b having a second width 920b that is greater than the first width 920a. User 1850 having the ability to adjust shank angle 902 (e.g., by alternately pivoting the shank 406 frontward 152 and rearward 133 relative to the position of distal end 130 of second section 129) further provides and facilitates him or her having the ability to securely and conveniently accommodate varying widths 920 of elongate structure 410. In the example use case, user 1850 removes system 2000 having rotatable shank 406 from first elongate structure 410a, and then adjusts shank angle 902 from the first shank angle 902a value (selected to accommodate the first width 920a) to the second shank angle 902b value (selected to accommodate the second width 920b). User 1850 then hangs system 2000 having rotatable shank 406 with shank angle 902 having the second shank angle 902b value from the second elongate structure 410b having the second width 920b. The selective and alternating adjustment of shank angle 902 through a plurality of values (e.g., first shank angle 902a value and second shank angle 902b value) further provides and facilitates the user 1850 having the ability to adjust (e.g., selectively and alternately increase and decrease) the effective slot width 510 of the slot 404 of hook 402. In the example use case provided above, the first shank angle 902a corresponds to a first slot width 510b (accommodating the first width 920a) and the second shank angle 902b corresponds to a second slot width 510b (accommodating the second slot width 920b).

Lock mechanism 918 included in system 2000 having rotatable shank 406 provides and facilitates user 1850 having the ability to selectively couple and decouple at least one of pin head 911 and flange 915 to and from at least one of first side 912 and second side 914, respectively, to further facilitate the selective and alternating increasing and decreasing of shank angle 902. In other embodiments, not shown (e.g., system embodiments where flange 915 is positioned proximate first side 912 and pin head 911 is positioned proximate second side 914), lock mechanism 918 provides and facilitates user 1850 having the ability to selectively couple and decouple at least one of flange 915 and pin head 911 to and from at least one of first side 912 and second side 914, respectively, to further facilitate the selective and alternating increasing and decreasing of shank angle 902.

In one embodiment of the systems (e.g., system 2000 including rotatable shank 406) described herein, lock mechanism 918 includes a peg (not shown) that is selectively and alternately inserted and removed into and out of a correspondingly and nestingly shaped peg receptacle (not shown) defined and formed in a surface of at least one of second side 914 of shank 906 and first side 912 of second section 129 proximate distal end 130. Thus, for example, user 1850 maintains the peg inserted into peg receptacle when he or she desires to maintain the otherwise rotatable shank 406 in a secured and fixed position (e.g., to prevent pivoting of shank 406 and to maintain shank angle 402 at a first predetermined shank angle 402a value).

To adjust shank angle 402 from the first shank angle 402a value to the second shank angle 402b value (e.g., as described in the use case example provided above), user 1850 removes (e.g., retracts) the peg from peg receptacle, thereby permitting the otherwise non-pivotable shank 406 to pivot about the shank pivot point 907 to the desired second shank angle 402b value. Upon reaching the second shank angle 402b value, user 1850 inserts the peg back into the peg receptacle to secure and affix the otherwise rotatable shank 406 in the second shank 406b position (e.g., to again prevent pivoting of shank 406 and to maintain shank angle 402 at a second predetermined shank angle 402b value). During such times when system 2000 having rotatable shank 406 is hanging from elongate structure 410, lock mechanism 918 prevents and/or reduces a probability of detachment (e.g., slippage) of system 2000 having rotatable shank 406 (and, similarly, other embodiments of the systems described herein having the rotatable shank 406). Lock mechanism 918 further provides and facilitates user 1850 having the ability to securely and conveniently accommodate varying widths 920 of different elongate structures 410, substantially as described above.

Figure 22:
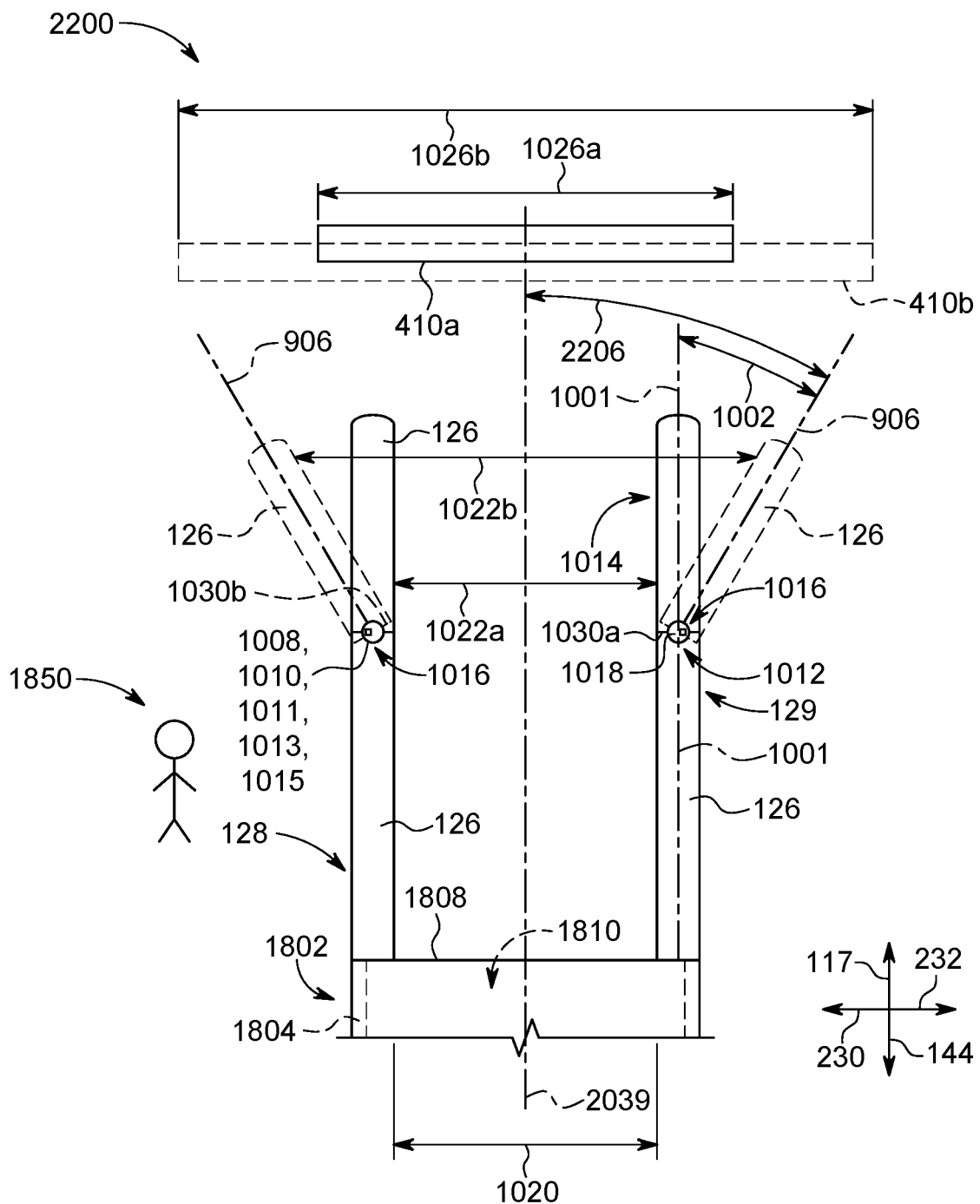
FIG. 22 is a front view diagram of an alternative embodiment of the hanger arms shown in FIG. 19.

FIG. 22 is a front view diagram of an alternative embodiment of the hanger arms shown in FIG. 19. In the embodiment shown in FIG. 22, a system 2200 includes two hanger arms 126. The first sections 128 of the two hanger arms 126 are spaced apart by a first lateral distance 1020, and the second sections 129 of the two hanger arms 126 are spaced apart by a second lateral distance 1022. The first section 128 and the second section 129 of each hanger arm 126 of the two hanger arms 126 are rotatably coupled together at a first arm section pivot point 1016. First section 128 includes a first section axis 1001, and second section 129 includes second section axis 906. A first angle 1002 is defined by an angle of second section axis 906 relative to first section axis 1001. First angle 1002 is selectively adjustable by user 1850 of system 2200 by rotating (e.g., pivoting) second section 129 about the first arm section pivot point 1016. Selectively adjusting first angle 1002 through rotation of second section 129 about the first arm section pivot point 1016 thereby provides and facilitates alternate increasing and decreasing of first angle 1002 by user 1850.

Also, in the embodiment shown in FIG. 22, basket 1802 includes a basket axis 2039. A second angle 2206 is defined by an angle of second section axis 906 relative to basket axis 2039. Second angle 2206 is selectively adjustable by user 1850 of system 2200 by rotating (e.g., pivoting) second section 129 about the first arm section pivot point 1016. Selectively adjusting second angle 2206 through rotation of second section 129 about the first arm section pivot point 1016 thereby provides and facilitates alternate increasing and decreasing of second angle 2206 by user 1850.

To provide and facilitate adjustment of first angle 1002 and second angle 2206 by user 1850, system 2200 includes a bore 1008 defined through at least one of the first section 128 and the second section 129. System 2200 also includes a pivot pin 1010 slidingly coupled to at least one of the first section 128 and the second section 129. Pivot pin 1010 includes a pin head 1011 and a pin shaft 1013. Pivot pin 1010 is inserted through bore 1008 from a first side 1012 of each hanger arm 126 of the two hanger arms 126 toward a second side 1014 of each hanger arm 126 of the two hanger arms 126. In other embodiments, not shown, pivot pin 1010 is inserted through bore 1008 from second side 1014 toward first side 1012. The pin shaft 1013 has a width substantially equal to a width of bore 1008. Pin head 1011 has a width greater than the width of pin shaft 1013 to prevent a complete travel of pin shaft 1013 through bore 1008. System 2200 also includes a flange 1015 coupled to pin shaft 1013 on one side thereof, for example and without limitation, proximate a surface of the second side 1014. Flange 1015 has a width that is greater than the width of bore 1008.

Also, in system 2200, first angle 1002 and second angle 2206 are securable in a substantially fixed position following adjustment of first angle 1002 and second angle 2206 by user 1850. To secure second section 129 and to fix first angle 1002 and second angle 2206 at the value (e.g., position of second section 129) selected by user 1850, system 2200 includes a locking mechanism 1018 coupled to at least one of pin head 1011 and flange 1015. Locking mechanism 1018 provides and facilitates user 1850 having the ability to selectively couple and decouple at least one of pin head 1011 and flange 1015 to and from at least one of first side 1012 and second side 1014, respectively. Moreover, adjustment of first angle 1002 and second angle 2206 provides and facilitates user 1850 having the ability to selectively adjust (e.g., alternately increase and decrease) the second lateral distance 1022.

In the embodiment shown in FIG. 22, the supportive structure 104 includes elongate structure 410 positioned substantially parallel to ground surface 412, not shown. Elongate structure 410 has a length 1026 that is greater than or substantially equal to the second lateral distance 1022. Thus, system 2200, like system 2000, is hangable from elongate structure 410 through a removable coupling of at least one of first section 128 and second section 128 (e.g., using hook 402) to elongate structure 410. Locking mechanism 1018, described above, provides and facilitates rotatable second section 129 having the ability to form a secure, but removable, load-bearing attachment of system 2200 from elongate structure 410. Locking mechanism 918 thereby prevents detachment of system 2200 from elongate structure 410 by reducing a probability of at least one of decoupling of system 2200 from elongate structure 410, undesired change of position of system 2200 when hanging from elongate structure 410, and uneven downward 144 forces exerted by a weight of system 2200 through a first hanger arm 126 as compared to a second hanger arm 126 (e.g., due to slippage and/or undesired rotation of second section 129 about first arm section pivot point 1016). Furthermore, locking mechanism 1018 provides and facilitates user 1850 having the ability to securely and conveniently accommodate varying lengths 1026 of different elongate structures 410.

In other embodiments, not shown, second section 129 of each hanger arm 126 of the two hanger arms 126 includes at least one fastener hole 138, substantially as shown and described above with reference to FIG. 1. In such other embodiments, systems not having hooks 402 are alternately attachable to and removable from supportive structure 104, including, without limitation, substantially vertical surface 134, substantially as shown and described above with reference to FIG. 1. User 1850 having the ability to selectively adjust the second lateral distance 1022 provides him or her benefits including, without limitation, conforming second lateral distance 1022 to locations of studs in wall(s) to which the disclosed devices and systems are desired to be attached to.

In still other embodiments, not shown, second section 129 is not rotatable about a first arm section pivot point 1016. Rather, at least a portion of the at least one hanger arm 126 is formed of a flexible material of construction. In such other embodiments, first angle 1002 and second angle 2206 are selectively adjustable to facilitate alternately increasing and decreasing the first angle 1002 and second angle 2206, and the second lateral distance 1022. The flexible material of construction of the at least a portion of the at least one hanger arm 126 is flexible enough to be manually manipulated by user 1850 in at least one direction (e.g., frontward 152, rearward 133, upward 117, downward 144, leftward 230, and rightward 232). Although the flexible material of construction of the at least a portion of the at least one hanger arm 126 in such other embodiments is manually manipulatable, it retains its shape and its load-bearing properties after being manipulated by user 1850. For example, and without limitation, user 1850 of system 2200 selectively adjusts the first angle 1002 and second angle 2206 by alternately flexing the second section 129 leftward 230 and rightward 232. Thus, the flexible material of construction of the at least a portion of the at least one hanger arm 126 provides and facilitates the at least one hanger arm 126 having the ability to form a secure, but removable, load-bearing attachment of this embodiment of system 2200 from elongate structure 410.

System 2200 having the flexible material of construction of the at least a portion of the at least one hanger arm 126 (e.g., instead of, or in addition to rotatable second section 129 and/or lock mechanism 1018) thereby prevents detachment of such system embodiments from elongate structure 410 by reducing a probability of decoupling of the system (e.g., at hook 402) from elongate structure 410 (e.g., due to slippage, breakage, and/or undesired changes in shape and/or load-bearing properties of hanger arm 126). Furthermore, the flexible material of construction of the at least a portion of the at least one hanger arm 126 provides and facilitates user 1850 having the ability to securely and conveniently accommodate varying lengths 1026 of different elongate structures 410.

In those embodiments (e.g., system 2200) having second angle 2206 that is adjustable by user 1850, pin head 1011 has a width that is greater than the width of pin shaft 1013 to prevent a complete travel of pin shaft 1013 through bore 1008 (substantially as shown and described above with reference to FIG. 10). Also, in the embodiment shown in FIG. 22, flange 1015 has a width that is greater than the width of bore 1008 in order to facilitate preventing detachment of the pivot pin 1010 from the bore 1008 when inserted therein 1008 (substantially as shown and described above with reference to FIG. 10). Thus, for example, and without limitation, a first end of pin shaft 1013 (e.g., opposite a second end thereof to which pin head 1011 is coupled to) is inserted through bore 1008 from first side 1012, and when so inserted, pin head 101 1 rests upon first side 1012. Flange 1015 is then coupled to the first end of pin shaft 1013 such that flange 1015 is positioned proximate second side 1014. In the embodiment shown in FIG. 22, both of flange 1015 and pin head 1011 are not further coupled to first side 1012 and second side 1014, respectively. In other embodiments, not shown, at least one of flange 1015 and pin head 1011 is further coupled to at least one of first side 1012 and second side 1014, respectively. Thus, in the example embodiment, the first section 128 and the second section 129 of each hanger arm 126 of the two hanger arms 126 are rotatably coupled together at a first arm section pivot point 1016. For example, and without limitation, flange 1015 is coupled to both the first end of the pin shaft 1013 and the second side 1014, where the second side 1014 is defined and positioned on the second section 129. The pin head 1011 rests upon, but is not coupled to, the first side 1012, where the first side 1012 is defined and positioned on an end of the first section 128 distal the basket 1802. As shown in FIG. 22, second section 129 thus rotates about an axis defined by pin shaft 1013 (substantially as shown in FIG. 10) relative to the first section axis 1001, and through a plurality of second section positions 1030 (e.g., a first second section position 1030a and a second second section position 1030b that is different from the first second section position 1030a, substantially as shown and described above with reference to FIG. 10).

Selective and alternating rotation (e.g., pivoting) of second section 129 by user 1850 provides and facilitates user 1850 having the ability to adjust (e.g., selectively and alternately increase and decrease) a second angle 2206 of a second section axis 906 relative to a basket axis 2039, which thereby provides and facilitates user 1850 having the ability to adjust (e.g., selectively and alternately increase and decrease) the second angle 2206 through a plurality of values (e.g., a first second angle 2206 value that is substantially equal to zero degrees, and a second second angle 2206 value having a value that is not equal to zero degrees). As user 1850 adjusts second angle 2206 from the first second angle value 2206 to the second second angle value 2206, the position of the second section 129 is likewise adjusted by user 1850 from a first second section position 1030*a* to a second second section position 1030*b* (substantially as shown and described above with reference to FIG. 10). Similarly, as user 1850 adjusts second angle 2206 from the first second angle value 2206 to the second second angle value 2206, a value of first angle 1002 is adjusted by user 1850 from a first first angle 1002 value (e.g., substantially equal to zero) to a second first angle 1002 value (e.g., not equal to zero degrees).

System 2200 is removably attached to supportive structure 104 (e.g., hangable from elongate structure 410 through a removable coupling of hook(s) 402 to elongate structure 410 through slot(s) 404). As described above, elongate structures 410 intended by user 1850 for use with the systems described herein include various shapes and sizes (e.g., widths 920, and lengths 1026). In an example use case, user 1850 desires to transfer system 2200 from a first elongate structure 410*a* having a first length 1026*a* to a second elongate structure 410*b* having a second length 1026*b* that is greater than the first length 1026*a*. User 1850 having the ability to adjust second angle 2206 (e.g., by alternately pivoting the second section 129 leftward 230 and rightward 232 relative to the basket axis 2039) further provides and facilitates him or her having the ability to securely and conveniently accommodate varying lengths 1026 of elongate structure 410. In the example use case, user 1850 removes system 2200 from first elongate structure 410*a*, and then adjusts second angle 2206 from the first second angle 2206 value (selected to accommodate the first length 1026*a*) to the second second angle 2206 value (selected to accommodate the second length 1026*b*). User 1850 then hangs system 2200 with second angle 2206 having the second second angle 2206 value from the second elongate structure 410*b* having the second length 1026*b*. The selective and alternating adjustment of second angle 2206 through a plurality of values (e.g., first second angle 2206 value and second second angle 2206 value) further provides and facilitates the user 1850 having the ability to adjust (e.g., selectively and alternately increase and decrease) the effective second lateral distance 1022. In the example use case provided above, the first second angle 2206 corresponds to a first second lateral distance 1022*a* (accommodating the first length 1026*a*) and the second second angle 2206 corresponds to a second second lateral distance 1022*b* (accommodating the second length 1026*b*).

Locking mechanism 1018 included in system 2200 provides and facilitates user 1850 having the ability to selectively couple and decouple at least one of pin head 1011 and flange 1015 to and from at least one of first side 1012 and second side 1014, respectively, to further facilitate the selective and alternating increasing and decreasing of second angle 2206. In other embodiments, not shown (e.g., system embodiments where flange 1015 is positioned proximate first side 1012 and pin head 1011 is positioned proximate second side 1014), locking mechanism 1018 provides and facilitates user 1850 having the ability to selectively couple and decouple at least one of flange 1015 and pin head 1011 to and from at least one of first side 1012 and second side 1014, respectively, to further facilitate the selective and alternating increasing and decreasing of second angle 2206.

In one embodiment of the systems (e.g., system 2200) described herein, locking mechanism 1018 includes a peg (not shown) that is selectively and alternately inserted and removed into and out of a correspondingly and nestingly shaped peg receptacle (not shown) defined and formed in a surface of at least one of second side 1014 of second section 129 and first side 1012 of first section 128 at the end thereof that is distal basket 1802. Thus, for example, user 1850 maintains the peg inserted into peg receptacle when he or she desires to maintain the otherwise rotatable second section 129 in a secured and fixed position (e.g., to prevent pivoting of second section 129 and to maintain second angle 2206 at a desired second angle 2206 value). To adjust second angle 2206 from the first second angle 2206 value to the second second angle 2206 value (e.g., as described in the use case example provided above), user 1850 removes (e.g., retracts) the peg from peg receptacle, thereby permitting the otherwise non-pivotable second section 129 to pivot about the first arm section pivot point 1016 to the desired second second angle 2206 value. Upon reaching the second second angle 2206 value, user 1850 inserts the peg back into the peg receptacle to secure and affix the otherwise rotatable second section 129 in the second second section position 1030*b* (e.g., to again prevent pivoting of second section 129 and to maintain second angle 2206 at a second predetermined second angle 2206 value). During such times when system 2200 is hanging from elongate structure 410, locking mechanism 1018 prevents and/or reduces a probability of detachment (e.g., slippage) of system 2200 (and, similarly, other embodiments of the systems described herein having the rotatable second section 129). Locking mechanism 1018 further provides and facilitates user 1850 having the ability to securely and conveniently accommodate varying lengths 1026 of different elongate structures 410, substantially as described above.

Figure 23:
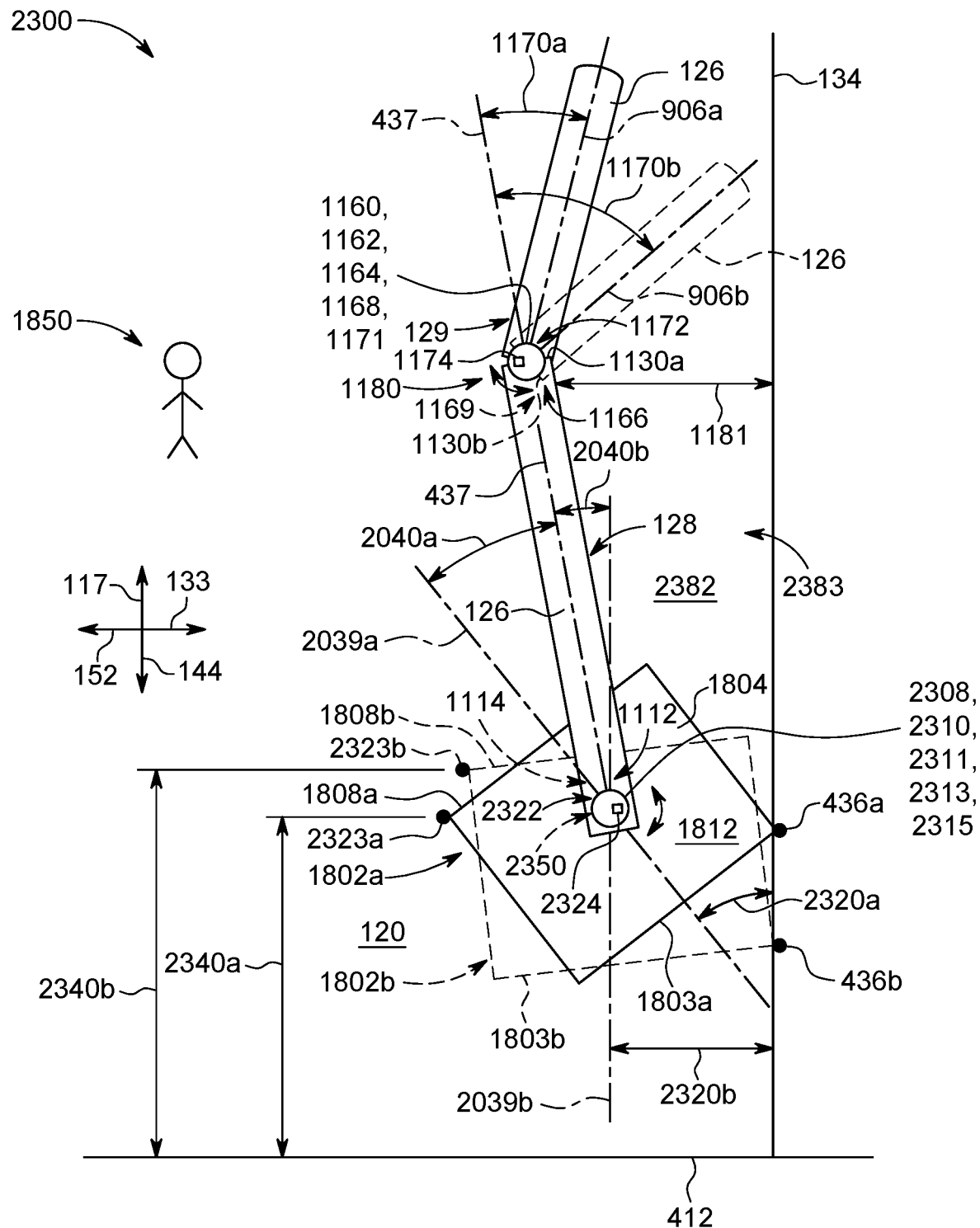
FIG. 23 is a side-view diagram of an alternative embodiment of the system shown in FIG. 20.

FIG. 23 is a side-view diagram of an alternative embodiment of the system shown in FIG. 20. In the embodiment shown in FIG. 23, a system 2300 includes the at least one hanger arm 126 coupled to the basket 1802. In system 2300, hanger arm 126 is further rotatably coupled to the basket 1802 at a coupling pivot point 2322. First section 128 of hanger arm 126 includes arm axis 437, and basket 1802 includes basket axis 2039. A coupling angle 2040 of arm axis 437 relative to basket axis 2039 is selectively adjustable by user 1850 of system 2300. Coupling angle 2040, in the embodiment shown in FIG. 23, is adjustable by user 1850 through at least one full rotation (e.g., greater than or equal to 360 degrees) of basket 1802 about coupling pivot point 2322. In other embodiments, not shown, coupling angle 2040 is adjustable by user 1850 through a range of rotational motion that is less than one full rotation of basket 1802 about coupling pivot point 2322. Further, in the embodiment shown in FIG. 23, basket 1802 is rotatable about coupling pivot point 2322 in both clockwise and counterclockwise directions to thereby enable and facilitate user 1850 to alternately increase and decreasing coupling angle 2040. In other embodiments, not shown, basket 1802 is rotatable by user 1850 in one of clockwise and counterclockwise directions.

Also, in the embodiment shown in FIG. 23, when system 2300 is attached to the supportive structure 104, a rearward 133 facing portion of basket 1802 contacts the substantially vertical surface 134 at at least one of a contact point 436 and a contact region 436. In consequence of this contact, a contact angle 2320 is formed and defined between basket axis 2039 and the substantially vertical surface 134. Basket 1802 being rotatable about coupling pivot point 2322, as described above, thereby provides and facilitates user 1850 having the ability to alternately increase and decrease the contact angle 2320. Furthermore, when system 2300 is attached to the supportive structure 104 (not shown), a point 2323 on basket top 1808 is positioned above ground surface 412 by a height 2340 (e.g., measured in centimeters). The selective adjustment of the coupling angle 2040 as described above further provides and facilitates user 1850 having the ability to selectively increase and decrease the height 2340.

[00233] To provide and facilitate adjustment of at least one of the coupling angle 2040 and the contact angle 2320 by user 1850, system 2300 includes a first bore 2308 defined through at least one of the first section 128 and at least a portion of the basket 1802. System 2300 also includes a first pivot pin 2310 slidingly coupled to at least one of the first section 128 and the at least a portion of the container 106. First pivot pin 2310 includes a first pin head 2311 and a first pin shaft 2313. First pivot pin 2310 is inserted through first bore 2308 from a first side 1112 of the first section 128 toward a second side 1114 of first section 128. In other embodiments, not shown, first pivot pin 2310 is inserted through first bore 2308 from second side 1114 toward first side 1112. The first pin shaft 2313 has a width substantially equal to a width of first bore 2308. First pin head 2311 has a width greater than the width of first pin shaft 2313 to prevent a complete travel of first pin shaft 2313 through first bore 2308. System 2300 also includes a first flange 2315 coupled to first pin shaft 2313 on one side thereof, for example and without limitation, proximate a surface of the second side 1114 coupled to basket 1802. First flange 2315 has a width that is greater than the width of first bore 2308.

Also, in system 2300, at least one of coupling angle 2040 and contact angle 2320 are securable in a substantially fixed position following adjustment of at least one of coupling angle 2040 and contact angle 2320 by user 1850. To secure first section 128 to basket 1802, and to fix at least one of coupling angle 2040 and contact angle 2320 at the value (e.g., position of first section 128) selected by user 1850, system 2300 includes a coupling lock 2324 coupled to at least one of first pin head 2311 and first flange 2315. Coupling lock 2324 provides and facilitates user 1850 having the ability to selectively couple and decouple at least one of first pin head 2311 and first flange 2315 to and from at least one of first side 1112 and second side 1114, respectively. Moreover, adjustment of at least one of coupling angle 2040 and contact angle 2320 provides and facilitates user 1850 having the ability to selectively adjust (e.g., alternately increase and decrease) at least one of coupling angle 2040 and contact angle 2320.

Further, in system 2300, first bore 2308 is further defined through the at least one basket side wall 1804. This embodiment of system 2300 further includes a seal 2350 positioned between first pin shaft 2313 and the at least one basket side wall 1804. Seal 2350 is further positioned proximate first flange 2315. In other embodiments, not shown, system 2300 does not include seal 2350 and first bore 2308 is not defined entirely through the at least one basket side wall 1804 (e.g., first bore 2308 does not extend through the entirety of basket side wall 1804).

In still other embodiments, not shown, basket 1802 and first section 128 are not rotatable relative to one another about coupling pivot point 2322. Rather, at least a portion of the at least one hanger arm 126 including, without limitation, at least a portion of first section 128, is formed of the flexible material of construction. In such other embodiments, at least one of coupling angle 2040 and contact angle 2320 are selectively adjustable to facilitate alternately increasing and decreasing at least one of coupling angle 2040 and the contact angle 2320. The flexible material of construction of the at least a portion of the at least one hanger arm 126 is flexible enough to be manually manipulated by user 1850 in at least one direction (e.g., frontward 152, rearward 133, upward 117, downward 144, leftward 230, and rightward 232).

Although the flexible material of construction of the at least a portion of the at least one hanger arm 126 in such other embodiments is manually manipulatable, it retains its shape and its load-bearing properties after being manipulated by user 1850. For example, and without limitation, user 1850 of system 2300 selectively adjusts at least one of the coupling angle 2040 and the contact angle 2320 by alternately flexing the first section 128 frontward 152 and rearward 133. Thus, the flexible material of construction of the at least a portion of the at least one hanger arm 126 provides and facilitates the at least one hanger arm 126 having the ability to form a secure, but adjustable, load-bearing attachment of this embodiment of system 2300 from supportive structure 104. System 2300 having the flexible material of construction of the at least a portion of the at least one hanger arm 126 (e.g., instead of, or in addition to coupling pivot point 2322 and/or coupling lock 2324) thereby prevents detachment of basket 1802 from hanger arm 126 in such system embodiments.

In still further embodiments, not shown, at least a portion of second section 129 is formed of a flexible material of construction. In such other embodiments, the flexible material of construction of the at least a portion of the second section 129 provides and facilitates user 1850 having the ability to manually manipulate second section 129 in at least one direction (e.g., frontward 152, rearward 133, upward 117, downward 144, leftward 230, and rightward 232). At least a portion of the second section 129 formed of the flexible material of construction further provides and facilitates user 1850 having the ability to selectively adjust (e.g., alternately increase and decrease) a third angle 1170 of a second section axis 906 of second section 129 relative to arm axis 437. For example, and without limitation, by alternately flexing the at least a portion of the second section 129 frontward 152 and rearward 133, user 1850 alternately decreases and increases third angle 1170.

Furthermore, in the embodiment shown in FIG. 23, when system 2300 is attached to supportive structure 104 (e.g., substantially vertical surface 134), the at least one hanger arm 126 is spaced from vertical surface 134 (e.g., wall) by an arm-to-vertical surface distance 1181. For example, and without limitation, the at least one hanger arm 126 further includes a midsection 1180 positioned between the distal end 130 (not shown) and the basket 1802. The midsection 1180 defines an approximate boundary between first section 128 and second section 129. Midsection 1180 is further positioned approximately equidistant between distal end 130 and basket 1802. In other embodiments, not shown, midsection 1180 is positioned closer to distal end 130 than to basket 1802. In still other embodiments, not shown, midsection 1180 is positioned nearer to basket 1802 than to distal end 130. Further, in those embodiments, not shown, including the at least a portion of the at least one hanger arm 126 formed of the flexible material of construction, the flexible material of construction further provides and facilitates user 1850 having the ability to selectively adjust (e.g., alternately increase and decrease) the arm-to-vertical surface distance 1181 by the alternate flexing manipulations by user 1850, as described above.

Also, when system 2300 is attached to the supportive structure 104 (e.g., substantially vertical surface 134), a first plane 2383 is approximately defined between the container 106, the at least one hanger arm 126, and the supportive structure 104 (e.g., the substantially vertical surface 134). The first plane 2383 has an area 2382. In those embodiments, not shown, including the at least a portion of the at least one hanger arm 126 formed of the flexible material of construction, the flexible material of construction further provides and facilitates user 1850 having the ability to selectively adjust (e.g., alternately increase and decrease) the area 2382 by the alternate flexing manipulations by user 1850, as described above.

Moreover, in the embodiment shown in FIG. 23, first section 128 and second section 129 are rotatably coupled together at a second arm section pivot point 1172. Third angle 1170, in the embodiment shown in FIG. 23, is adjustable by user 1850 through at least one full rotation (e.g., greater than or equal to 360 degrees) of second section 129 about second arm pivot point 1172. In other embodiments, not shown, third angle 1170 is adjustable by user 1850 through a range of rotational motion that is less than one full rotation of container about second arm pivot point 1172. Further, in the embodiment shown in FIG. 23, second section 129 is rotatable about coupling pivot point 2322 in both clockwise and counterclockwise directions to thereby enable and facilitate user 1850 to alternately increase and decreasing third angle 1170.

In other embodiments, not shown, second section 129 is rotatable by user 1850 in one of clockwise and counterclockwise directions. By manipulating at least one of the first section 128 and the second section 129 (e.g., by pivoting one of them relative to the other about second arm pivot point 1172), user 1850 of system 2300 selectively adjusts (e.g., alternately increases and decreases) third angle 1170 of second section axis 906 relative to arm axis 437 to facilitate alternately increasing and decreasing the third angle 1170. When system 2300 is attached to supportive structure 104 (e.g., vertical surface 134), the selective adjustment of the third angle 1170 further provides and facilitates the user 1850 having the ability to alternately increase and decrease the arm-to-vertical surface distance 1181, and thereby alternately increase and decrease the area 2382 of the first plane 2383. Likewise, when system 2300 is attached to supportive structure 104 (e.g., vertical surface 134), the selective adjustment of the third angle 1170 further provides and facilitates the user 1850 having the ability to alternately increase and decrease the height 1140 and the contact angle 2320, substantially as described above with reference to pivoting the basket 1802 about the coupling pivot point 2322.

To provide and facilitate adjustment of at least one of the third angle 1170 by user 1850, system 2300 includes a second bore 1160 defined through at least one of the first section 128 and the second section 129. System 2300 also includes a second pivot pin 1162 slidingly coupled to at least one of the first section 128 and the second section 129. Second pivot pin 1162 includes a second pin head 1164 and a second pin shaft 1168. Second pivot pin 1162 is inserted through second bore 1160 from a first side 1166 of the at least one hanger arm 126 toward a second side 1169 of the at least one hanger arm 126. In other embodiments, not shown, second pivot pin 1162 is inserted through second bore 1160 from second side 1169 toward first side 1166. The second pin shaft 1168 has a width substantially equal to a width of second bore 1160. Second pin head 1164 has a width greater than the width of second pin shaft 1168 to prevent a complete travel of second pin shaft 1168 through second bore 1160. System 2300 also includes a second flange 1171 coupled to second pin shaft 1168 on one side thereof, for example and without limitation, proximate a surface of the second side 1169. Second flange 1171 has a width that is greater than the width of second bore 1160.

Also, in system 2300, third angle 1170 is securable in a substantially fixed position following adjustment of the third angle 1170 by user 1850. For example, and without limitation, to secure first section 128 to second section 129, and to fix third angle 1170 at the value (e.g., position of second section 129 relative to first section 128) selected by user 1850, system 2300 includes an arm lock mechanism 1174 coupled to at least one of second pin head 1164 and second flange 1171. Arm lock mechanism 1174 provides and facilitates user 1850 having the ability to selectively couple and decouple at least one of second pin head 1164 and second flange 1171 to and from at least one of first side 1166 and second side 1169, respectively. Moreover, adjustment of third angle 1170 provides and facilitates user 1850 having the ability to selectively adjust (e.g., alternately increase and decrease) third angle 1170. When system 2300 is attached to the supportive structure 104 (e.g., substantially vertical surface 134), arm lock mechanism 1174 further provides and facilitates the user 1850 having the ability to selectively adjust (e.g., alternately increase and decrease) the arm-to-vertical distance 1181 and thereby the area 2382 of the first plane 2383.

Furthermore, the flexible material of construction of the at least a portion of the first section 128 provides and facilitates user 1850 having the ability to selectively and alternately adjust at least one of the coupling angle 2040, the contact angle 2320, the area 2382, the height 2340, and the arm-to-vertical surface distance 1181. In other embodiments, not shown, at least one portion of the at least one hanger arm 126 other than or in addition to the at least a portion of the first section 128 is formed of the flexible material of construction to provide similar benefits to user 1850 of the systems (e.g., system 2300) described herein. For example, and without limitation, in such other embodiments, at least one of first section 128 and second section 129 is formed of the flexible material of construction to provide and facilitate the user 1850 having the ability to selectively and alternately transition hanger arm 126 from a substantially straight and vertical hanger arm 126 (e.g., having an angle of arm axis 437 relative to second section axis 906 that is substantially equal to zero degrees, as shown in FIG. 18) to the arcuately curved hanger arm 126 (e.g., where an angle of arm axis 437 relative to second section axis is not substantially equal to zero degrees, as shown in FIG. 20). User 1850 transitioning the curvature of hanger arm 126 further provides and facilitates user 1850 having the ability to selectively and alternately adjust at least one of the third angle 1170, the coupling angle 2040, the contact angle 2320, the area 2382, the height 2340, and the arm-to-vertical surface distance 1181.

In those embodiments (e.g., system 2300) having at least one of coupling angle 2040 and contact angle 2320 that is adjustable by user 1850, first pin head 2311 has a width that is greater than the width of first pin shaft 2313 to prevent a complete travel of first pin shaft 2313 through first bore 2308. Also, in the embodiment shown in FIG. 23, first flange 2315 has a width that is greater than the width of first bore 2308 in order to facilitate preventing detachment of the first pivot pin 2310 from the first bore 2308 when inserted therein. Thus, for example, and without limitation, a first end of first pin shaft 2313 (e.g., opposite a second end thereof to which first pin head 2311 is coupled to) is inserted through first bore 2308 from first side 1112, and when so inserted, first pin head 2311 rests upon first side 1112. First flange 2315 is then coupled to the first end of first pin shaft 2313 such that first flange 2315 is positioned proximate a portion of a surface of basket 1802 (e.g., a portion of basket side wall 1804) that faces into the basket cavity 1812. Inclusion of seal 2350 proximate at least one of first flange 2315, first pin head 2311, and first pin shaft 2313 prevents and/or mitigates leakage of fluid 102 from and/or into basket cavity 1812 to and/or from exterior 120.

In the embodiment shown in FIG. 23, both of first flange 2315 and first pin head 2311 are not further coupled to first side 1112 and the portion of a surface of basket 1802 106 that faces into basket cavity 1812, respectively. In other embodiments, not shown, at least one of first flange 2315 and first pin head 2311 is further coupled to at least one of first side 1112 and the portion of a surface of basket 1802 that faces into basket cavity 1812, respectively. Thus, in the example embodiment, first section 128 is rotatably coupled to the basket 1802. For example, and without limitation, first flange 2315 is coupled to both the first end of the first pin shaft 2313 and the portion of a surface of basket 1802 that faces into basket cavity 1812. The first pin head 2311 rests upon, but is not coupled to, the first side 1112, where the first side 1112 is defined and positioned on the first section 128 proximate the basket 1802 and the coupling pivot point 2322.

As shown in FIG. 23, first section 128 thus rotates about an axis defined by first pin shaft 2313 relative to basket axis 2039, and through a plurality of coupling angle 2040 values (e.g., a first coupling angle 2040a value and a second coupling angle 2040b value that is different from the first coupling angle 2040a value). User 1850 pivoting first section 128 about coupling pivot point 2322 also transitions system 2300 through a plurality of contact angle 2320 values (e.g., a first contact angle 2320a value and a second contact angle 2320b value that is different from the first contact angle 2320a value). Furthermore, user 1850 pivoting first section 128 about coupling pivot point 2322 also transitions system 2300 through a plurality of height 2340 values (e.g., a first height 2340a value and a second height 2340b value that is different from the first height 2340a value). Moreover, adjustment of coupling angle 2040 by user 1850 pivoting first section 128 about coupling pivot point 2322 transitions basket 1802 through a plurality of positions (e.g., a first basket 1802a position and a second basket 1802b position that is different from the first basket 1802a position), and further transitions system 2300 through a plurality of area 2382 values (e.g., a first area 2382 value and a second area 2382 value that is different from the first area 2382 value). Similarly, adjustment of coupling angle 2040 by user 1850 pivoting first section 128 about coupling pivot point 2322 transitions system 2300 through a plurality of arm-to-vertical surface distance 1181 values (e.g., a first arm-to-vertical surface distance 1181 value and a second arm-to-vertical surface distance 1181 value that is different from the first arm-to-vertical surface distance 1181 value).

In the embodiment illustrated in FIG. 23, coupling lock 2324 included in system 2300 provides and facilitates user 1850 having the ability to selectively couple and decouple at least one of first pin head 2311 and first flange 2315 to and from at least one of first side 1112 and the aforementioned portion of a surface of basket 1802 that faces into basket cavity 1812, respectively, to further facilitate the selective and alternating increasing and decreasing of at least one of the coupling angle 2040, the contact angle 2320, the area 2382, the height 2340, and the arm-to-vertical surface distance 1181. In other embodiments, not shown (e.g., system embodiments where first flange 2315 is positioned proximate first side 1112 and first pin head 2311 is positioned proximate the portion of a surface of basket 1802 that faces into basket cavity 1812), coupling lock 2324 provides and facilitates user 1850 having the ability to selectively couple and decouple at least one of first flange 2315 and first pin head 2311 to and from at least one of first side 1112 and portion of a surface of basket 1802 that faces into basket cavity 1812, respectively, to further facilitate the selective and alternating increasing and decreasing of at least one of the coupling angle 2040, the contact angle 2320, the area 2382, the height 2340, and the arm-to-vertical surface distance 1181.

In one embodiment of the systems (e.g., system 2300) described herein, coupling lock 2324 includes a peg (not shown) that is selectively and alternately inserted and removed into and out of a correspondingly and nestingly shaped peg receptacle (not shown) defined and formed in a surface of at least one of a portion of an exterior 120 facing surface of basket 1802 proximate coupling pivot point 2322 and first side 1112 of first section 128 proximate coupling pivot point 2322. Thus, for example and without limitation, user 1850 maintains the peg inserted into peg receptacle when he or she desires to maintain the rotatable first section 128 in a secured and fixed position (e.g., to prevent pivoting of first section 128 and to maintain coupling angle 2040 at a first predetermined coupling angle 2040a value).

In an example use case, to adjust coupling angle 2040 from the first coupling angle 2040a value to the second coupling angle 2040b value, user 1850 removes (e.g., retracts) the peg from peg receptacle, thereby permitting the otherwise non-pivotable first section 128 to pivot about the coupling pivot point 2322 to the desired second coupling angle 2040b value.

Upon reaching the second coupling angle 2040b value, user 1850 inserts the peg back into the peg receptacle to secure and affix the otherwise rotatable first section 128 at the second coupling angle 2040b value (e.g., to again prevent pivoting of first section 128 and to maintain coupling angle 2040 and basket 1802 at a second predetermined coupling angle 2040b value and a second basket 1802b position, respectively). During such times when system 2300 (and, similarly, other embodiments of the systems described herein having the rotatable first section 128) is hanging from elongate structure 410, coupling lock 2324 prevents and/or reduces a probability of pivoting (e.g., slippage) of first section 128 relative to basket 1802. Coupling lock 2324 further provides and facilitates user 1850 having the ability to securely and conveniently accommodate system 2300 to different offset structures 432 having, for example and without limitation, varying distances 432 of elongate structure(s) 410 from substantially vertical surface(s) 134.

Moreover, in some embodiments of the systems described herein, the flexible material of construction of the at least a portion of the second section 129 provides and facilitates user 1850 having the ability to selectively and alternately adjust at least one of the third angle 1170, the contact angle 2320, the area 2382, the height 2340, and the arm-to-vertical surface distance 1181. In other embodiments, not shown, at least one portion of the at least one hanger arm 126 other than or in addition to the at least a portion of the second section 129 is formed of the flexible material of construction to provide similar benefits to user 1850 of the systems (e.g., system 2300) described herein. For example, and without limitation, in such other embodiments, at least one of first section 128 and second section 129 is formed of the flexible material of construction to provide and facilitate the user 1850 having the ability to selectively and alternately transition hanger arm 126 from a substantially straight and vertical hanger arm 126 (e.g., having an angle of arm axis 437 relative to second section axis 906 that is substantially equal to zero degrees, as shown in FIG. 18) to the arcuately curved hanger arm 126 (e.g., where an angle of arm axis 437 relative to second section axis is not substantially equal to zero degrees, as shown in FIG. 20). User 1850 transitioning the curvature of hanger arm 126 further provides and facilitates user 1850 having the ability to selectively and alternately adjust at least one of the third angle 1170, the coupling angle 2040, the contact angle 2320, the area 2382, the height 2340, and the arm-to-vertical surface distance 1181.

In those embodiments (e.g., system 2300) having third angle 1170 that is adjustable by user 1850, second pin head 1164 has a width that is greater than the width of second pin shaft 1168 to prevent a complete travel of second pin head 1164 through second bore 1160.

Also, in the embodiment shown in FIG. 23, second flange 1171 has a width that is greater than the width of second bore 1160 in order to facilitate preventing detachment of the second pivot pin 1162 from the second bore 1160 when inserted therein. Thus, for example, and without limitation, a first end of second pin head 1164 (e.g., opposite a second end thereof to which second pin head 1164 is coupled to) is inserted through second bore 1160 from first side 1166, and when so inserted, second pin head 1164 rests upon first side 1166. Second flange 1171 is then coupled to the first end of second pin head 1164 such that second flange 1171 is positioned proximate second side 1169. In the embodiment shown in FIG. 23, both of second flange 1171 and second pin head 1164 are not further coupled to first side 1166 and second side 1169, respectively. In other embodiments, not shown, at least one of second flange 1171 and second pin head 1164 is further coupled to at least one of first side 1166 and second side 1169, respectively. Thus, in the example embodiment, the first section 128 and the second section 129 of each hanger arm 126 of the two hanger arms 126 are rotatably coupled together at second arm section pivot point 1172. For example, and without limitation, second flange 1171 is coupled to both the first end of the second pin shaft 1168 and the second side 1169, where the second side 1169 is defined and positioned on the second section 129. The second pin head 1164 rests upon, but is not coupled to, the first side 1166, where the first side 1166 is defined and positioned on an end of the first section 128 distal the basket 1802. As shown in FIG. 23, second section 129 thus rotates about an axis defined by second pin shaft 1168 relative to the arm axis 437, and through a plurality of second section positions 1130 (e.g., a first second section position 1130a and a second second section position 1130b that is different from the first second section position 1130a).

As shown in FIG. 23, second section 129 thus rotates about an axis defined by second pin shaft 1168 relative to arm axis 437 and relative to basket axis 2039, and second section 129 rotates through a plurality of third angle 1170 values (e.g., a first third angle 1170a value and a second third angle 1170b value that is different from the first third angle 1170a value). User 1850 pivoting second section 129 about second arm section pivot point 1172 also transitions system 2300 through a plurality of contact angle 2320 values (e.g., a first contact angle 2320a value and a second contact angle 2320b value that is different from the first contact angle 2320a value). Furthermore, user 1850 pivoting second section 129 about second arm section pivot point 1172 also transitions system 2300 through a plurality of height 2340 values (e.g., a first height 2340a value and a second height 2340b value that is different from the first height 2340a value). Moreover, adjustment of third angle 1170 by user 1850 pivoting second section 129 about second arm section pivot point 1172 transitions basket 1802 through a plurality of positions (e.g., a first basket 1802a position and a second basket 1802b position that is different from the first basket 1802a position), and further transitions system 2300 through a plurality of area 2382 values (e.g., a first area 2382 value and a second area 2382 value that is different from the first area 2382 value). Similarly, adjustment of third angle 1170 by user 1850 pivoting second section 129 about second arm section pivot point 1172 transitions system 2300 through a plurality of arm-to-vertical surface distance 1181 values (e.g., a first arm-to-vertical surface distance 1181 value and a second arm-to-vertical surface distance 1181 value that is different from the first arm-to-vertical surface distance 1181 value).

In the embodiment illustrated in FIG. 23, arm lock mechanism 1174 included in system 2300 provides and facilitates user 1850 having the ability to selectively couple and decouple at least one of second pin head 1164 and second flange 1171 to and from at least one of first side 1166 and second side 1169, respectively, to further facilitate the selective and alternating increasing and decreasing of at least one of the third angle 1170, the contact angle 2320, the area 2382, the height 2340, and the arm-to-vertical surface distance 1181. In other embodiments, not shown (e.g., system embodiments where second flange 1171 is positioned proximate first side 1166 and second pin head 1164 is positioned proximate second side 1169), arm lock mechanism 1174 provides and facilitates user 1850 having the ability to selectively couple and decouple at least one of second flange 1171 and second pin head 1164 to and from at least one of first side 1166 and second side 1169, respectively, to further facilitate the selective and alternating increasing and decreasing of at least one of the third angle 1170, the contact angle 2320, the area 2382, the height 2340, and the arm-to-vertical surface distance 1181.

In one embodiment of the systems (e.g., system 2300) described herein, arm lock mechanism 1174 includes a peg (not shown) that is selectively and alternately inserted and removed into and out of a correspondingly and nestingly shaped peg receptacle (not shown) defined and formed in a surface of at least one of a portion of a portion of second section 129 facing second pin head 1164 and proximate second arm section pivot point 1172, and first side 1166 of first section 128 proximate second arm section pivot point 1172. Thus, for example and without limitation, user 1850 maintains the peg inserted into peg receptacle when he or she desires to maintain the otherwise rotatable second section 129 in a secured and fixed position (e.g., to prevent pivoting of second section 129 and to maintain third angle 1170 at a first predetermined third angle 1170a value).

In another example use case, to adjust third angle 1170 from the first third angle 1170a value to the second third angle 1170b value, user 1850 removes (e.g., retracts) the peg from peg receptacle, thereby permitting second section 129 to pivot about the second arm section pivot point 1172 to the desired second third angle 1170b value. Upon reaching the second third angle 1170b value, user 1850 inserts the peg back into the peg receptacle to secure and affix the otherwise rotatable second section 129 at the second third angle 1170b value (e.g., to again prevent pivoting of second section 129 and to maintain third angle 1170 at a second predetermined third angle 1170b value). During such times when system 2300 (and, similarly, other embodiments of the systems described herein having the rotatable second section 129) is hanging from elongate structure 410, arm lock mechanism 1174 prevents and/or reduces a probability of pivoting (e.g., slippage) of second section 129 relative to first section 128. Arm lock mechanism 1174 further provides and facilitates user 1850 having the ability to securely and conveniently accommodate system 2300 to different offset structures 432 having, for example and without limitation, varying distances 432 of elongate structure(s) 410 from substantially vertical surface(s) 134.

Figure 24A:
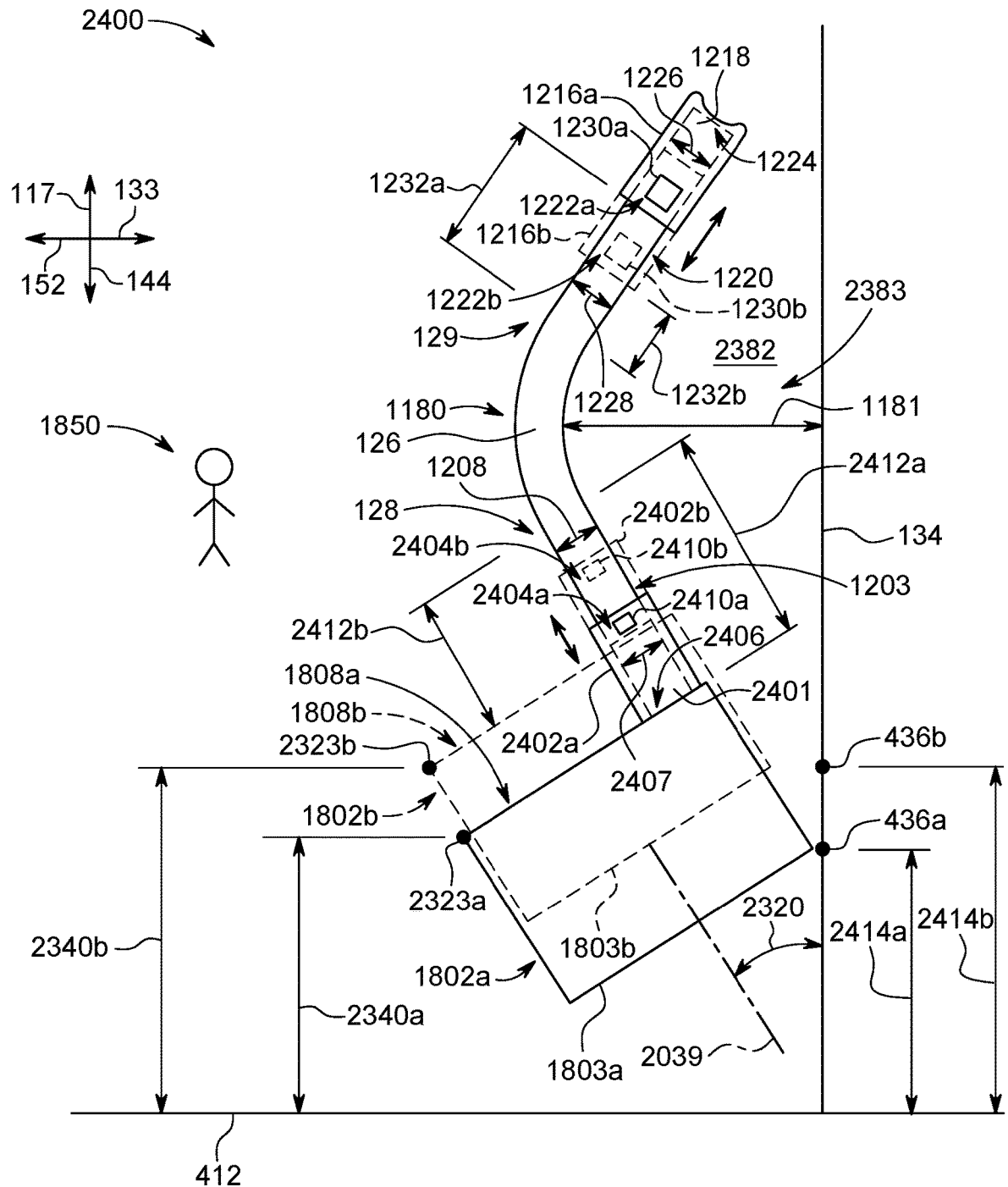
FIG. 24A is a side-view diagram of another embodiment of the system shown in FIG. 20.

FIG. 24A is a side-view diagram of another embodiment of the system shown in FIG. 20. In the embodiment shown in FIG. 24A, a system 2400 includes a lower sleeve 2402. Lower sleeve 2402 is at least one of coupled to and formed within at least a portion of at least one of the basket 1802 and the first section 128. In the embodiment shown in FIG. 24A, first section 128 is a two-piece first section 128, with a first part including lower sleeve 2402 positioned proximate basket 1802, and with a second part of first section 128 positioned proximate midsection 1180 of hanger arm 126. The lower sleeve 2402 extends generally upward 117 from the basket 1802. In other embodiments, not shown, lower sleeve 2402 is positioned proximate midsection 1180, and the second part of first section 128 (e.g., which does not include lower sleeve 2402) is positioned proximate basket 1802. In such other embodiments, lower sleeve 2402 extends generally downward 144 from hanger arm 126 proximate midsection 1180.

The lower sleeve 2402 includes a lower sleeve cavity 2401 defined within the lower sleeve 2402. Lower sleeve cavity 2401 includes a lower sleeve opening 2404 facing generally upward 117. Lower sleeve cavity 2401 extends generally downward 144 from the lower sleeve opening 2404 to a lower sleeve bottom 2406 proximate basket 1802. Lower sleeve cavity 2401 has a lower sleeve interior width 2407 that is substantially equal to a first section width 1208 of the first section 128. The first section 128 includes a proximate end 1203 slidingly coupled to the lower sleeve 2402 through (e.g., inside of) the lower sleeve cavity 2401.

Also, in the embodiment shown in FIG. 24A, when system 2400 is attached to supportive structure 104 (e.g., substantially vertical surface 134), the at least one hanger arm 126 is spaced from vertical surface 134 (e.g., wall) by an arm-to-vertical surface distance 1181. For example, and without limitation, the at least one hanger arm 126 further includes a midsection 1180 positioned between the distal end 130 (not shown) and the basket 1802. The midsection 1180 defines an approximate boundary between first section 128 and second section 129. Midsection 1180 is further positioned approximately equidistant between distal end 130 and basket 1802. In other embodiments, not shown, midsection 1180 is positioned closer to distal end 130 than to basket 1802. In still other embodiments, not shown, midsection 1180 is positioned nearer to basket 1802 than to distal end 130. By manipulating at least one of the first section 128 and the lower sleeve 2402, user 1850 of system 2400 selectively adjusts a position of proximate end 1203 in lower sleeve cavity 2401 to facilitate alternately increasing and decreasing a first section distance 2412 between the basket top 1808 and the midsection 1180. Furthermore, when system 2400 is attached to supportive structure 104 (e.g., substantially vertical surface 134), point 2323 on basket top 1808 is positioned above ground surface 412 by height 2340, and the selective adjustment of the position of proximate end 1203 in lower sleeve cavity 2401 further facilitates selectively increasing and decreasing the height 2340.

Further, in the embodiment shown in FIG. 24A, when system 2400 is attached to the supportive structure 104 (e.g., substantially vertical surface 134), a rearward 133 facing portion of basket 1802 contacts the substantially vertical surface 134 at at least one of contact point 436 and contact region 436. The at least one of the contact point 436 and the contact region 436 is positioned above ground surface 412 by an elevation 2414. The above described selective adjustment of the position of proximate end 1203 in lower sleeve cavity 2401 further facilitates selectively increasing and decreasing the elevation 2414 by user 1850. Also, when said system 2400 is attached to supportive structure 104 (e.g., substantially vertical surface), first plane 2383 (having area 2382) is approximately defined between basket 1802, the at least one hanger arm 126, and the substantially vertical surface 134. The above described selective adjustment of the position of proximate end 1203 in lower sleeve cavity 2401 further facilitates selectively increasing and decreasing the area 2382 by the user 1850 when system 2400 is attached to supportive structure (e.g., substantially vertical surface 134). Likewise, the above described selective adjustment of the position of proximate end 1203 in lower sleeve cavity 2401 further facilitates selectively increasing and decreasing the contact angle 2320 by the user 1850 when system 2400 is attached to supportive structure (e.g., substantially vertical surface 134).

To provide and facilitate adjustment of the position of proximate end 1203 in lower sleeve cavity 2401 by user 1850, system 2400 includes a lower sleeve lock mechanism 2410 coupled to the lower sleeve 2402. Lower sleeve lock mechanism 2410 is selectively coupled to the first section 128 when proximate end 1203 is slidingly coupled to the lower sleeve 2402 through the lower sleeve cavity 2401. By the action and manipulation by user 1850 of system 2400, lower sleeve lock mechanism 2410 selectively and alternately couples and decouples the first section 128 from the lower sleeve 2402 to further facilitate selectively and alternately increasing and decreasing at least one of the height 2340, the area 2382, and the elevation 2414.

In the embodiment shown in FIG. 24A, system 2400 also includes an upper sleeve 1216. Upper sleeve 1216 is at least one of coupled to and formed within at least a portion of the second section 129 of the at least one hanger arm 126. In the embodiment shown in FIG. 24A, second section 129 is a two-piece second section 129, with a first part including upper sleeve 1216 positioned proximate distal end 130 (not shown), and with a second part of second section 129 positioned proximate midsection 1180 of hanger arm 126. The upper sleeve 1216 extends generally downward 144 from distal end 130. In other embodiments, not shown, upper sleeve 1216 is positioned proximate midsection 1180, and the second part of second section (e.g., which does not include upper sleeve 1216) is positioned proximate distal end 130. In such other embodiments, upper sleeve 1216 extends generally upward 117 from hanger arm 126 proximate midsection 1180.

The upper sleeve 1216 includes an upper sleeve cavity 1218 defined within the upper sleeve 1216. Upper sleeve opening 1222 includes an upper sleeve opening 1222 facing generally downward 144. Upper sleeve cavity 1218 extends generally upward 117 from the upper sleeve opening 1222 to an upper sleeve top 1224 proximate distal end 130. Upper sleeve cavity 1218 has an upper sleeve interior width 1226 that is substantially equal to a second section width 1228 of the second section 129. The second section 129 includes an upper end 1220 slidingly coupled to the upper sleeve 1216 through (e.g., inside of) the upper sleeve cavity 1218.

Also, in the embodiment shown in FIG. 24A, by manipulating at least one of the second section 129 and the upper sleeve 1216, user 1850 of system 2400 selectively adjusts a position of upper end 1220 in upper sleeve cavity 1218 to facilitate alternately increasing and decreasing a second section distance 1232 between the distal end 130 and the midsection 1180. Furthermore, when system 2400 is attached to supportive structure 104 (e.g., substantially vertical surface 134), point 2323 on basket top 1808 is positioned about ground surface 412 by height 2340, and the selective adjustment of upper end 1220 in upper sleeve cavity 1218 further facilitates selectively increasing and decreasing the height 2340.

Further, in the embodiment shown in FIG. 24A, when system 2400 is attached to the supportive structure 104 (e.g., substantially vertical surface 134), the rearward 133 facing portion of basket 1802 contacts the substantially vertical surface 134 at at least one of contact point 436 and contact region 436. The at least one of the contact point 436 and the contact region 436 is positioned above ground surface 412 by the elevation 2414. The above described selective adjustment of the position of upper end 1220 in upper sleeve cavity 1218 further facilitates selectively increasing and decreasing the elevation 2414 by user 1850. Also, when said system 2400 is attached to supportive structure 104 (e.g., substantially vertical surface), first plane 2383 (having area 2382) is approximately defined between basket 1808, the at least one hanger arm 126, and the substantially vertical surface 134. The above described selective adjustment of the position of upper end 1220 in upper sleeve cavity 1218 further facilitates selectively increasing and decreasing the area 2382 by the user 1850 when system 2400 is attached to supportive structure (e.g., substantially vertical surface 134). Likewise, the above described selective adjustment of the position of upper end 1220 in upper sleeve cavity 1218 further facilitates selectively increasing and decreasing the contact angle 2320 by the user 1850 when system 2400 is attached to supportive structure (e.g., substantially vertical surface 134).

To provide and facilitate adjustment of the position of upper end 1220 in upper sleeve cavity 1218 by user 1850, system 2400 includes an upper sleeve lock mechanism 1230 coupled to the upper sleeve 1216. Upper sleeve lock mechanism 1230 is selectively coupled to the second section 129 when upper end 1220 is slidingly coupled to the upper sleeve 1216 through the upper sleeve cavity 1218. By the action and manipulation by user 1850 of system 2400, upper sleeve lock mechanism 1230 selectively and alternately couples and decouples the second section 129 from the upper sleeve 1216 to further facilitate selectively and alternately increasing and decreasing at least one of the height 2340, the area 2382, and the elevation 2414.

Figure 24B:
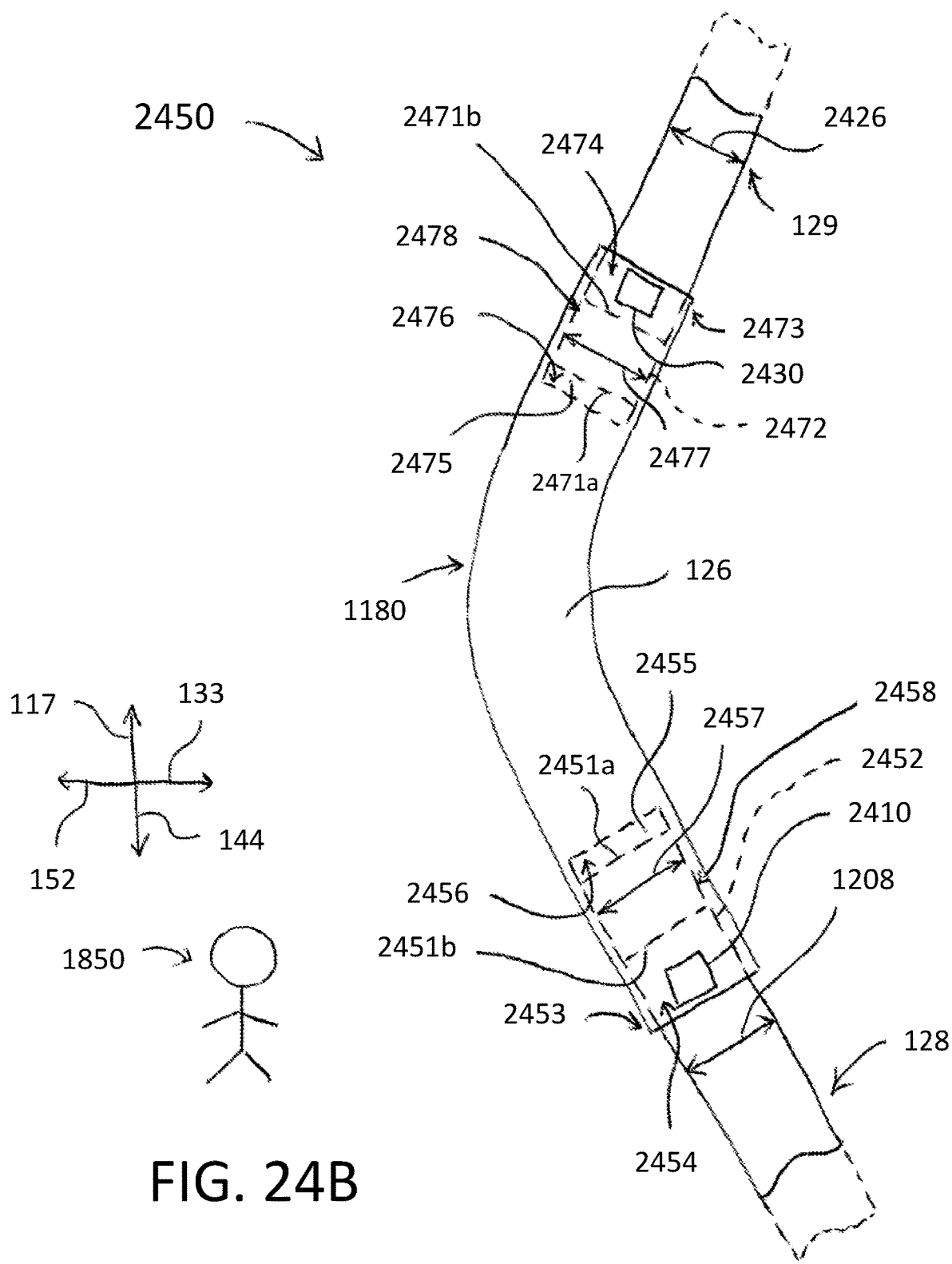
FIG. 24B is a side-view diagram of an alternative embodiment of the system shown in FIG. 24A.

FIG. 24B is a side-view diagram of an alternative embodiment of the system shown in FIG. 24A. As shown in FIG. 24B, a system 2450 includes a lower sleeve 2452 at least one of coupled to and formed in a first end 2453 of the midsection 1180. The lower sleeve 2452 extends distally (e.g., generally downwardly 144) from the first end 2453 toward the basket 1802 (not shown in FIG. 24B). The lower sleeve 2452 includes a lower sleeve cavity 2455 defined within the lower sleeve 2452. The lower sleeve cavity 2455 includes a lower sleeve opening 2454 positioned opposite from the midsection 1180 and facing away from the midsection 1180. The lower sleeve opening 2454 extends distally from the lower sleeve opening 2454 to a lower sleeve bottom 2456 proximate the midsection 1180. The lower sleeve cavity 2455 has a lower sleeve interior width 2457 that is greater than or substantially equal to the first section width 1208 of the first section 128. In system 2450, the first section 128 includes a distal end 2458 slidingly coupled to the lower sleeve 2452 through the lower sleeve cavity 2455.

By manipulating at least one of the first section 128 and the lower sleeve 2452, the user 1850 of system 2450 selectively adjusts a position of the distal end 2458 in the lower sleeve cavity 2455 to facilitate alternately increasing and decreasing the first section distance 2412 between the basket 1802 and the midsection 1180, substantially as shown and described with reference to FIG. 24A. System 2450 also includes lower sleeve lock mechanism 2410 coupled to the lower sleeve 2452 and selectively coupled to the first section 128 when the distal end 2458 is slidingly coupled to the lower sleeve 2452 through the lower sleeve cavity 2455. The lower sleeve lock mechanism 2410 is configured to selectively couple and decouple the first section 128 to the lower sleeve 2452 to further facilitate selectively increasing and decreasing the first section distance 2412 (e.g., from a first position 2451*a* to a second position 2451*b*).

System 2450 includes an upper sleeve 2472 at least one of coupled to and formed in a second end 2473 of the midsection 1180. The upper sleeve 2472 extends distally (e.g., generally upward 117) from the second end 2473 toward the distal end 130 (not shown in FIG. 24B). The upper sleeve 2472 includes an upper sleeve cavity 2475 defined within the upper sleeve 2472. The upper sleeve cavity 2475 includes an upper sleeve opening 2474 positioned opposite from the midsection 1180 and facing away from the midsection 1180. The lower upper opening 2474 extends distally from the upper sleeve opening 2474 to an upper sleeve bottom 2476 proximate the midsection 1180. The upper sleeve cavity 2475 has an upper sleeve interior width 2477 that is greater than or substantially equal to the second section width 2426 of the second section 129. In system 2450, the second section 129 includes a distal end 2478 slidingly coupled to the upper sleeve 2472 through the upper sleeve cavity 2475.

By manipulating at least one of the second section 129 and the upper sleeve 2472, the user 1850 of system 2450 selectively adjusts a position of the distal end 2478 in the upper sleeve cavity 2475 to facilitate alternately increasing and decreasing the second section distance 1232 between the distal end 130 and the midsection 1180, substantially as shown and described above with reference to FIG. 24A. System 2450 also includes upper sleeve lock mechanism 2430 coupled to the upper sleeve 2472 and selectively coupled to the second section 129 when the distal end 2478 is slidingly coupled to the upper sleeve 2472 through the upper sleeve cavity 2475. The upper sleeve lock mechanism 2430 is configured to selectively couple and decouple the second section 129 to the upper sleeve 2472 to further facilitate selectively increasing and decreasing the second section distance 1232 (e.g., from a first position 2471*a* to a second position 2471*b*).

Figure 25:
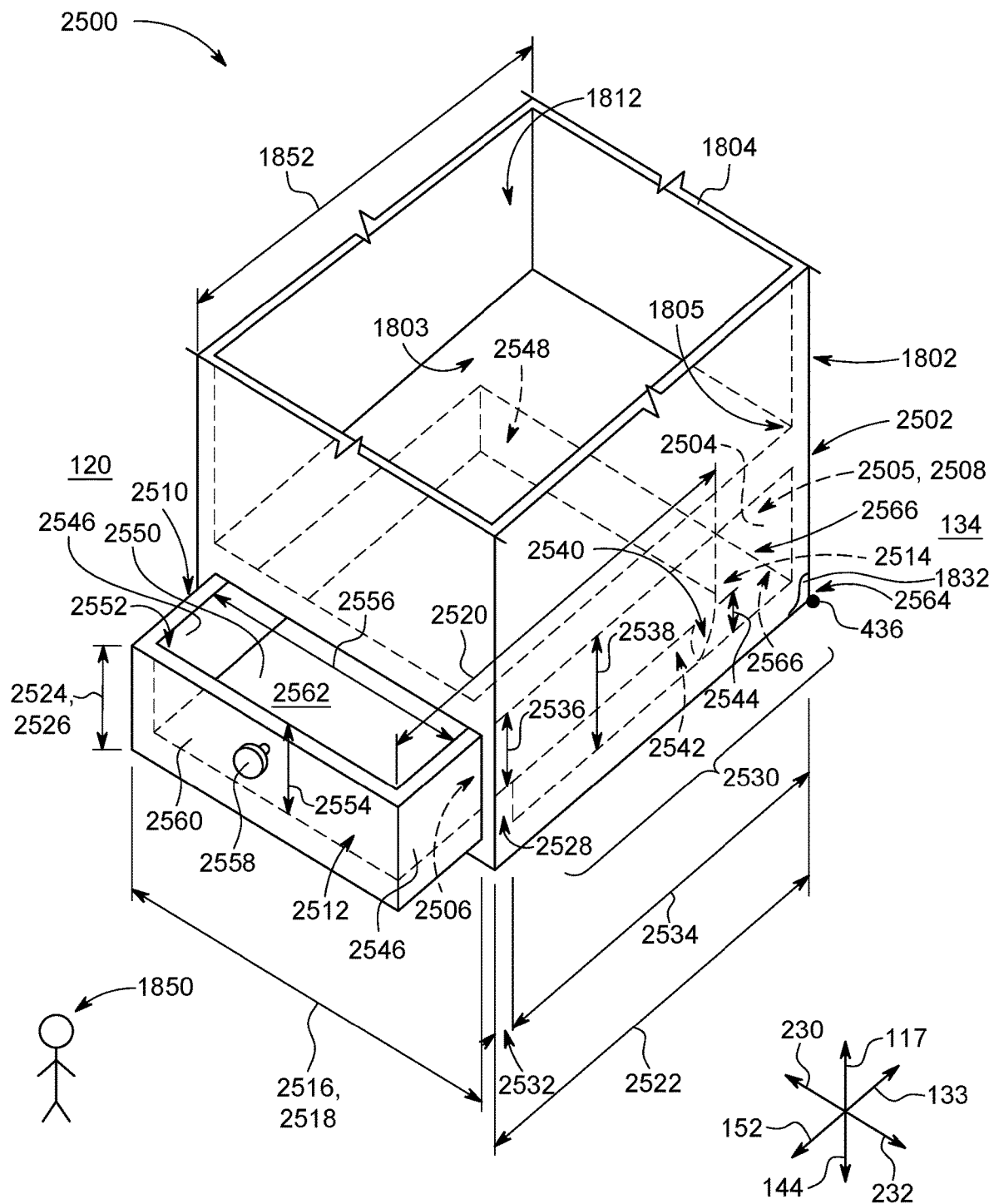
FIG. 25 is a perspective-view diagram of an alternative embodiment of the devices shown in FIGS. 18, 19, 20, 22, 23, and 24A.

FIG. 25 is a perspective-view diagram of an alternative embodiment of the systems shown in FIGS. 18, 19, 20, 22, 23, and 24. In the embodiment shown in FIG. 25, a system 2500 includes a base extension 2502 coupled to the basket base 1803 of basket 1802. Base extension 2502 extends generally downward 144 from the basket base 1803. Base extension 2502 includes an under-base cavity 2504 defined within the base extension 2502. The under-base cavity 2504 includes a first under-base opening 2506 facing generally frontward 152. The under-base cavity 2504 extends generally rearward 133 through at least a portion of the base extension 2502 to a cavity rearward 133 extent 2505.

Also, in the embodiment shown in FIG. 25, the under-base cavity 2504 extends generally rearward 133 entirely through the base extension 2502 from the first under-base opening 2506 to a second under-base opening 2508. The second under-base opening 2508 faces generally rearwardly 133. In other embodiments, not shown, under-base cavity 2504 does not extend entirely through base extension 2502, but, rather, extends rearwardly 133 from first under-base opening 2506 only part way through base extension 2502 (e.g., extending between half and seven eights through the base extension 2502). In such other embodiments, system 2500 does not include the second under-base opening 2508.

System 2500 also includes at least one drawer 2510. Drawer 2510 includes a generally frontward 152 facing drawer front 2512 and a generally rearward 133 facing drawer back 2514. Drawer 2510 has a drawer width 2516 that is less than or substantially equal to a cavity width 2518 of the under-base cavity 2504. Drawer 2510 also has a drawer length 2520 defined as a distance between the drawer front 2512 and the drawer back 2514. The drawer length 2520 is less than or substantially equal to a cavity length 2522, the cavity length 2522 defined as a distance between the first under-base opening 2506 and the cavity rearward 133 extent 2505. The drawer 2510 is slidingly inserted into the under-base cavity 2504 with the drawer back 2514 facing the cavity rearward 133 extent 2505.

Also, in system 2500, drawer 2510 also has a drawer height 2524 that is less than or substantially equal to an opening height 2526 of the first under-base opening 2506. The under-base cavity 2504 also includes a frontward section 2528 and a rearward section 2530. The frontward section 2528 has a first length 2532, and the rearward section 2530 has a second length 2534. The first length 2532 is less than the second length 2534, and a sum of the first length 2532 and the second length 2534 is substantially equal to the cavity length 2522. The frontward section 2528 also has a first height 2536 that is greater than or substantially equal to the drawer height 2524, and the rearward section 2530 has a second height 2538. In the embodiment shown in FIG. 25, the second height 2538 is greater than the first height 2536. In other embodiments, not shown, the second height 2538 is substantially equal to the first height 2536.

Further, in the embodiment shown in FIG. 25, drawer 2510 includes a drawer stop 2540 coupled to a generally downward 144 facing drawer surface 2542 of the drawer 2510. The drawer stop 2510 extends generally downward 144 from the drawer surface 2542 by a stop distance 2544. The stop distance 2544 is greater than zero. The stop distance 2544 is also less than or substantially equal to a difference between the second height 2538 and the first height 2536. Drawer 2510 further includes at least two drawer side walls 2546 coupled to and between the drawer front 2512 and the drawer back 2514. The at least two drawer side walls 2546 are positioned opposite one another, and the at least two drawer side walls 2546 are separated by a distance that is less than or substantially equal to the drawer width 2516. Drawer 2510 further includes one drawer cavity 2548 defined by the drawer front 2512, the drawer back 2514, and a drawer base 2550. The drawer cavity 2548 includes a drawer cavity opening 2552 facing generally upward 117, and the drawer cavity 2548 extends generally downward 144 through at least a portion of the drawer 2510 to the drawer base 2550. The at least one drawer cavity 2548 has a drawer cavity depth 2554 that is less than the drawer height 2524 and the drawer cavity 2548 also has a drawer cavity width 2556 that is less than the drawer width 2516. In other embodiments, not shown, drawer 2510 does not include drawer stop 2540. In such other embodiments, the height of the under-base cavity 2504 is substantially equal to first height 2536, and under-base cavity 2504 does not include a separate frontward section 2528 and separate rearward section 2530.

Although illustrated as a drawer 2510 that alternately may be pushed and pulled into and out of the under-base cavity 2504 in the disclosed embodiments of system 2500 in frontward 152 and rearward 133 directions, respectively, a person of ordinary skill in the art will recognize and appreciate that the drawer 2510 may alternatively by positioned in system 2500 from a leftward 230 to rightward 232 direction, or similarly, in a rightward 232 to leftward 230 direction. Furthermore, a person of ordinary skill in the art will recognize and appreciate that, in additional embodiments of the disclosed system having one or more drawers and/or under-base cavity 2504 (e.g., as shown and described herein), the orientation of the drawer(s) and/or the at least one under-base cavity 2504 may be similarly varied in the aforementioned manner.

Figure 26A:
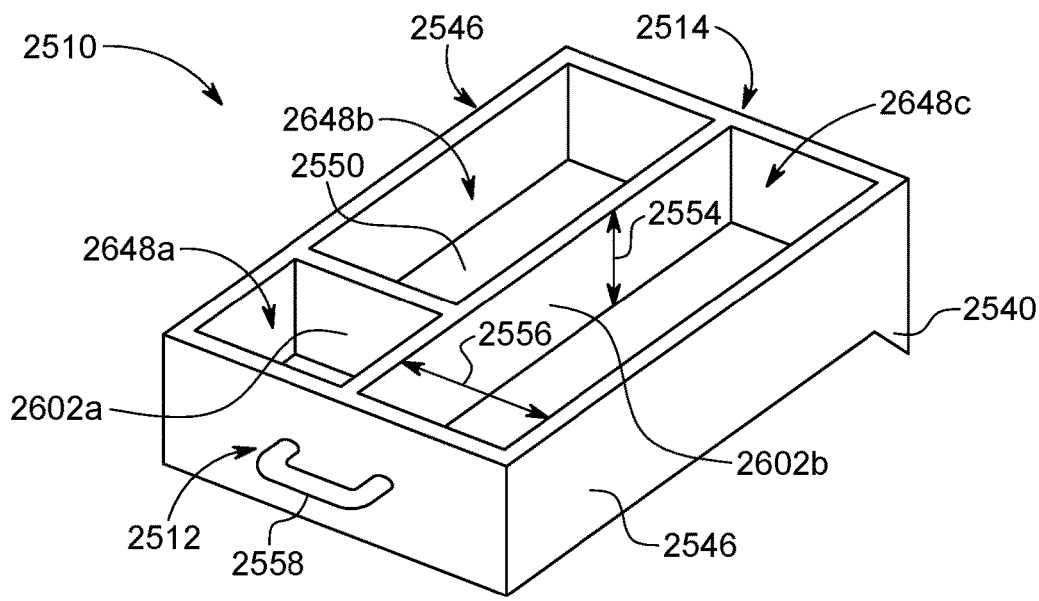
FIG. 26A is a perspective-view diagram of an alternative embodiment of the drawer shown in FIG. 25.

In another embodiment shown in FIG. 26A, drawer 2510 includes a plurality of drawer cavities 2648 (e.g., a first drawer cavity 2648a, a second drawer cavity 2648b, and a third drawer cavity 2648c). In the embodiment shown in FIG. 26A, first drawer cavity 2648a is defined by a first portion of the drawer front 2512, a first drawer cavity divider 2604a, a first portion of a second drawer divider 2604b, a first portion of a first one of the two drawer side walls 2546, and the drawer base 2550. Second drawer cavity 2648b is defined by a first portion of the drawer back 2514, the first drawer cavity divider 2604a, a second portion of the second drawer divider 2604b, a second portion of the first one of the two drawer side walls 2546, and the drawer base 2550. Third drawer cavity 2648c is defined by a second portion of the drawer back 2514, the second drawer divider 2604b, a second one of the two drawer side walls 2546, and the drawer base 2550.

Also, in the embodiment shown in FIG. 26A, each drawer cavity 2648 of the plurality of drawer cavities 2648 has substantially equivalent drawer cavity depths 2554 and drawer cavity widths 2556, but each drawer cavity 2648 of the plurality of drawer cavities 2648 has a different volume. In other embodiments, not shown, each drawer cavity 2648 of the plurality of drawer cavities 2648 has a substantially equivalent volume (e.g., embodiments in which the plurality of drawer cavities 2648 includes an even number of drawer cavities 2648). In still other embodiments, not shown, each drawer cavity 2648 of the plurality of drawer cavities 2648 does not have substantially drawer cavity depth 2554, and in yet other embodiments, not shown, each drawer cavity 2648 of the plurality of drawer cavities 2648 does not have substantially drawer cavity width 2556.

Drawer 2510 further includes at least one drawer grip 2558. Drawer grip 2558 is at least one of formed in and coupled to a frontward 152 facing drawer front surface 2560 of the drawer front 2512. Drawer grip 2558 provides and facilitates user 1850 of system 2500 to selectively and alternately slide the drawer 2510 rearwardly 133 and frontwardly 152 into and out of, respectively, the under-base cavity 2504. User 1850 sliding the drawer 2510 frontward also facilitates increasing a drawer cavity opening area 2562 exposed to the exterior 120 of system 2500. Similarly, user 1850 sliding the drawer 2510 rearward 133 further facilitates decreasing the drawer cavity opening area 2562 exposed to exterior 120.

Moreover, when system 2500 is attached to supportive structure 104 (e.g., substantially vertical surface 134, not shown) through at least one hanger arm 126, not shown, a rearward 133 facing portion of the base extension 2502 contacts the substantially vertical surface 134 at the at least one of the contact point 436 and the contact region 436. The rearward 133 facing portion of the base extension 2502 includes an arcuate fillet 2564 formed at a rearward 133 downward 144 corner 2566 of the base extension 2502. The arcuate fillet 2564 is convexly formed with respect to the substantially vertical surface 134 and is concavely formed with respect to the under-base cavity 2504. When attached to the supportive structure 104, system 2500 further contacts the substantially vertical surface 134 at the arcuate fillet 2564. In other embodiments, not shown, system 2500 does not include arcuate fillet 2564. In such other embodiments, in place of arcuate fillet 2564, corner 2566 of base extension 2502 includes, for example, and without limitation, a substantially square corner, substantially as shown and described above with reference to FIG. 21.

System 2500 also includes bumper 1832 coupled to an exterior 120 surface of the rearward 133 facing portion of the base extension 2502. When system 2500 is attached to supportive structure 104 (e.g., substantially vertical surface 134), system 2500 further contacts the substantially vertical surface 134 at the bumper 1832. In the embodiment shown in FIG. 25, bumper 1832 is coupled to the exterior 120 rearward 133 facing surface of arcuate fillet 2564 and, when hanging from supportive structure 104 (e.g., substantially vertical surface 134), system 2500 further contacts the substantially vertical surface 134 at the bumper 1832.

Figure 26B:
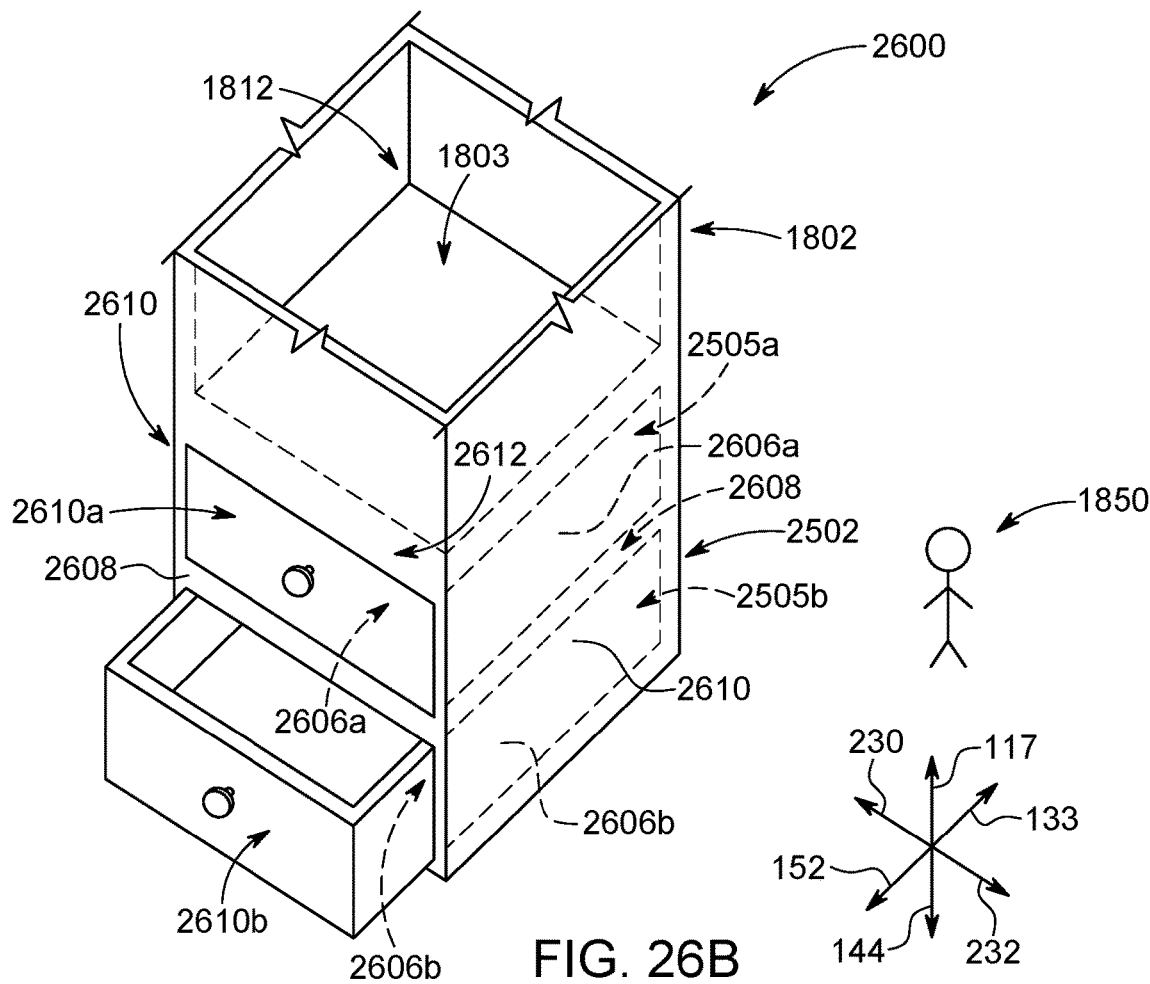
FIG. 26B is a perspective-view diagram of an alternative embodiment of the system shown in FIG. 25.

In yet another embodiment shown in FIG. 26B, a system 2600 includes a plurality of drawers 2610 (e.g., a first drawer 2610*a* and a second drawer 2610*b*). In the embodiment shown in FIG. 26B, each drawer 2610 of the plurality of drawers 2610 are stacked vertically beneath basket base 1803. For example, and without limitation, immediately beneath (e.g., downward 144 from) basket base 1803, first drawer 2610*a* is slidingly inserted into a first under-base cavity 2606*a*, substantially as shown and described above with reference to FIG. 25. Second drawer 2610*b* is positioned beneath (e.g., downward 144 from) first drawer 2610*a*. Second drawer 2610*b* is slidingly inserted into a second under-base cavity 2606*b*, substantially as shown and described above with reference to FIG. 25. System 2600 also includes a horizontal drawer separation 2608 positioned between first drawer 2610*a* and second drawer 2610*b*. Horizontal drawer separation 2608 extends from a left 230 base extension side wall 2610 to a right 232 base extension side wall 2610. Horizontal drawer separation 2608 further extends from a base extension front surface 2612 to the respective cavity rearward 133 extent 2505 of first under-base cavity 2604*a* and second under-base cavity 2604*b*.

Figure 27:
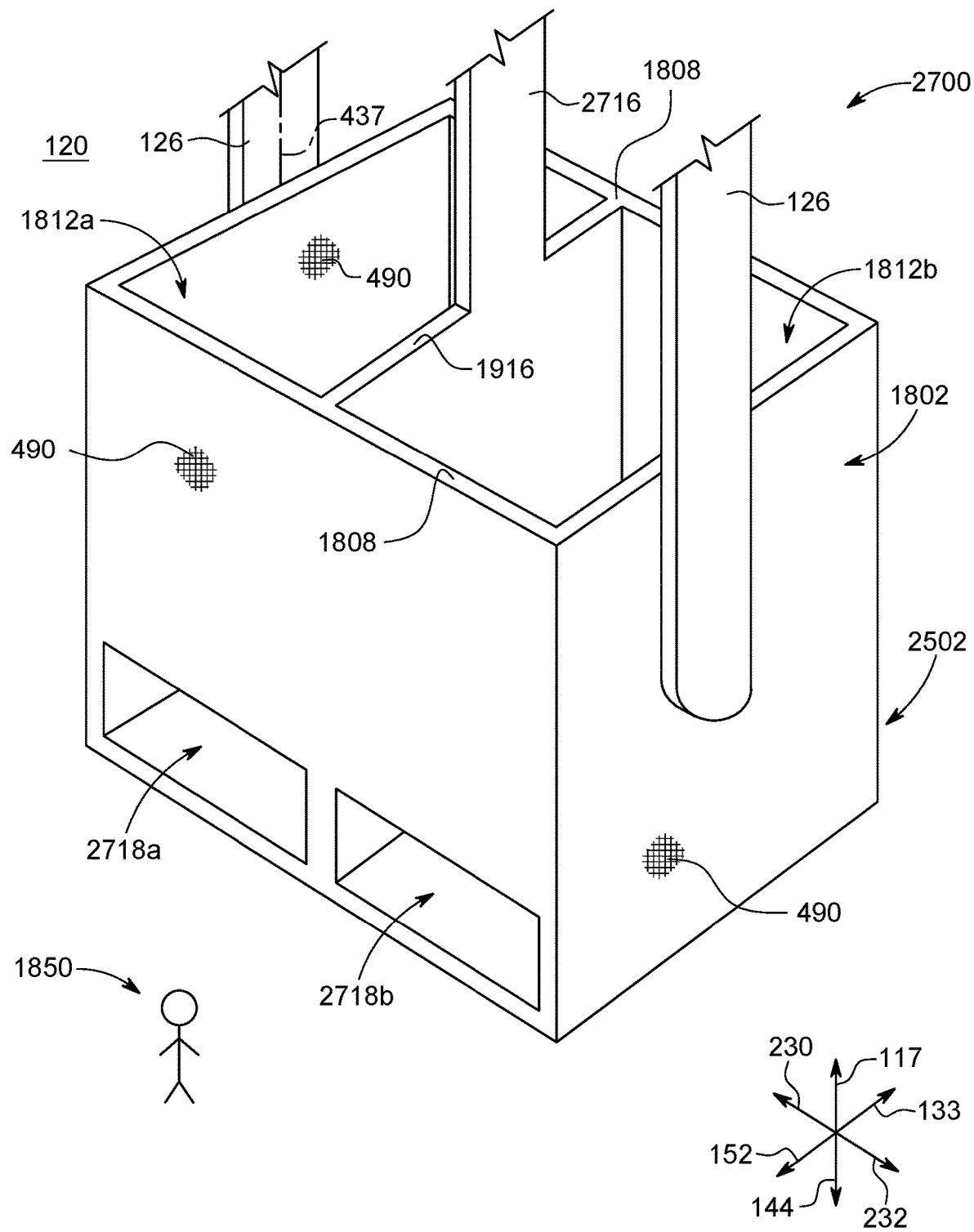
FIG. 27 is a perspective-view diagram of another embodiment of the device shown in FIGS. 18-20, 22, 23, 24A, 25, and 26B.

FIG. 27 is a perspective-view diagram of another embodiment of the device shown in FIGS. 18-20, 22-25, and 26B. In the embodiment shown in FIG. 27, basket 1802 of a system 2700 includes a plurality of basket cavities 1812. The plurality of basket cavities 1812 includes a first basket cavity 1812*a* and a second basket cavity 1812*b*. In other embodiments, not shown, the plurality of basket cavities 1812 includes more than two basket cavities 1812. The first basket cavity 1812*a* is positioned adjacent the second interior cavity 1812*b*. System 2700 also includes a partition wall 1916 coupled to and between a frontward 152 facing portion of the at least one basket side wall 1804 and a rearward facing portion of the at least one basket side wall 1804, with partition wall 1916 further coupled to basket base 1803. In other embodiments, not shown, partition wall 1916 is not further coupled to basket base 1803. In still other embodiments, not shown, partition wall 1916 is coupled to and between a leftward 230 facing portion of the at least one basket side wall 1804 and a rightward 232 facing portion of the at least one basket side wall 1804, with partition wall 1916 further coupled to basket base 1803. Partition wall 1916 separates (e.g., structurally isolates) the first basket cavity 1812*a* from the second basket cavity 1812*b*.

Also, in the embodiment shown in FIG. 27, system 2700 includes a third hanger arm 2716 coupled to the basket 1802. In system 2700, for example and without limitation, third hanger arm 2716 is coupled to and extends generally upward 117 from partition wall 1916. Third hanger arm 2716 is thereby positioned laterally between the first and the second hanger arms 126. In other embodiments, not shown, third hanger arm 2716 is coupled to basket base 1803. In still other embodiments, not shown, third hanger arm 2716 is coupled to a rearward portion of basket top 1808. Furthermore, in system 2700, the third hanger arm 2716 further extends generally upward 117 from the basket 1802 by the arm distance 204, substantially as shown and described above with reference to FIG. 19. In other embodiments, not shown, the first and second hanger arms 126 extend generally upward 117 from basket 1802 by a distance that is less than arm distance 204. In such other embodiments, third hanger arm 2716 extends generally upward 117 from basket 1802, and at least one of first and second hanger arms 126 is coupled to third hanger arm 2716 at a point (not shown) on third hanger arm 2716 positioned between basket 1802 and distal end 130 (not shown) of third hanger arm 2716.

In yet other embodiments, not shown, third hanger arm 2716 further includes one or more of the several features shown and described above with reference to FIG. 18 (e.g., a substantially straight third hanger arm 2716 that extends generally upward 117 and substantially vertically from basket 1802), FIG. 19 (e.g., a third hanger arm 2716 including hook 402), FIG. 20 (e.g., an arcuately curved third hanger arm 2716), FIG. 22 (e.g., a third hanger arm 2716 having a second angle 2206 that is selectively and alternately increasable and decreasable by user 1850), FIG. 23 (e.g., a third hanger arm 2716 having at least one of a third angle 1170 and a coupling angle 2040 that is selectively and alternately increasable and decreasable by user 1850), and FIG. 24A (e.g., a third hanger arm 2716 having at least one of a lower sleeve 2402 and an upper sleeve 1216). Moreover, in still more embodiments, not shown, the systems shown and described above include more than three hanger arms coupled to basket 1802 at one or more positions different from where third hanger arm 2716 is coupled to basket 1802 and different from where first and second hanger arms 126 are coupled to basket 1802.

System 2700 further includes a plurality of under-base cavities 2718. The plurality of under-base cavities 2718 includes a first under-base cavity 2718*a* and a second under-base cavity 2718*b*. In other embodiments, not shown, the plurality of under-base cavities 2718 includes more than two under-base cavities 2718. In the embodiment shown in FIG. 27, the first under-base cavity 2718*a* is positioned adjacent to and to the left 230 of the second under-base cavity 2718. In other embodiments, the first under-base cavity 2718*a* is positioned adjacent to and atop 117 the second under-base cavity 2718*b*, substantially as shown and described above with reference to FIG. 26B. Also, in the embodiment shown in FIG. 27, each under-base cavity 2718 of the plurality of under-base cavities 2718 does not include a drawer 2610 and/or a drawer 2510. In other embodiments, not shown, system 2700 further includes at least one drawer 2610 and/or at least one drawer 2510, slidingly inserted into at least one under-base cavity 2718 of the plurality of under-base cavities 2718.

Figure 28:
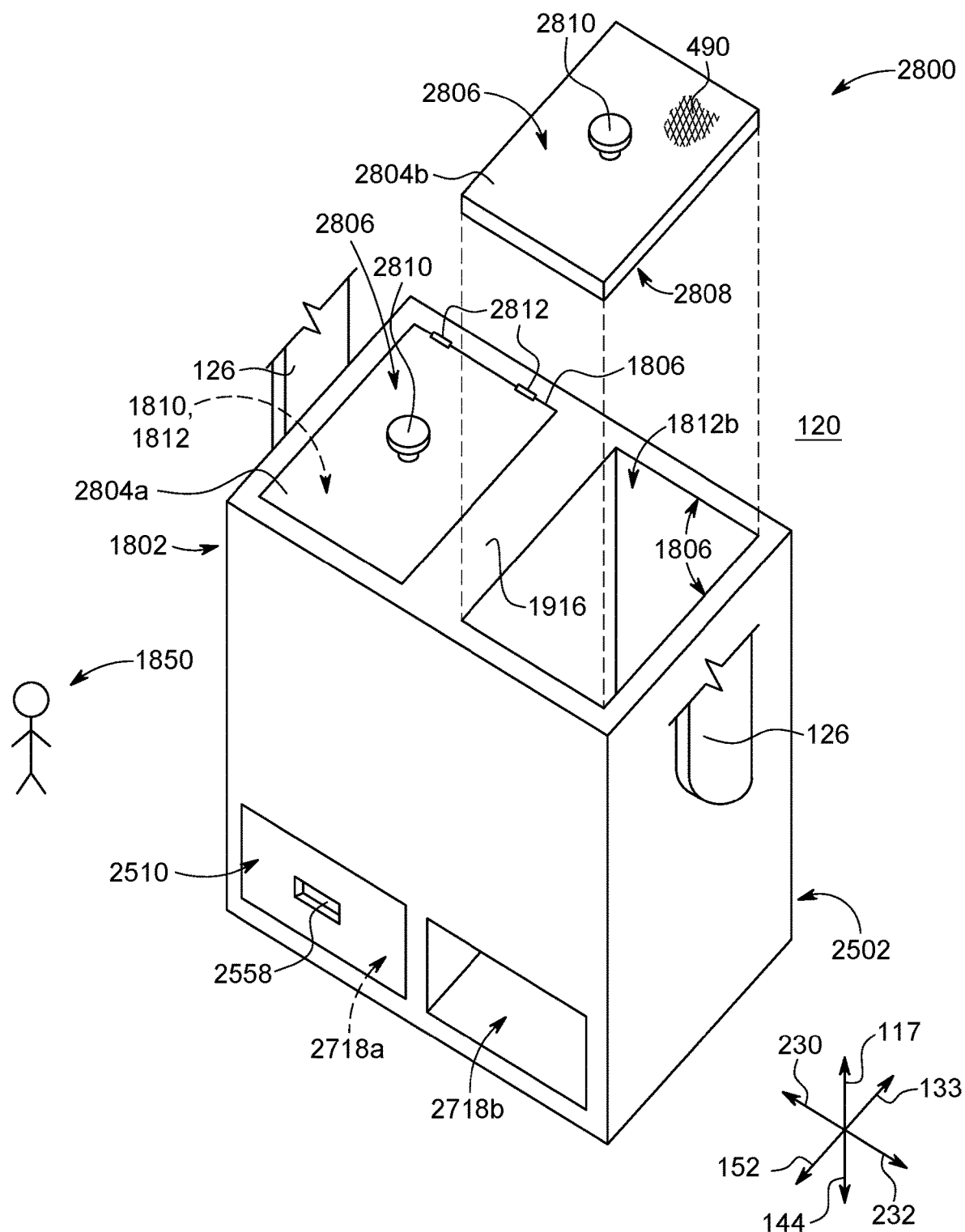
FIG. 28 is a perspective-view diagram of an alternative embodiment of the system shown in FIG. 27.

FIG. 28 is a perspective-view diagram of an alternative embodiment of the system shown in FIG. 27. In the embodiment shown in FIG. 28, in a system 2800, basket 1802 includes at least two basket cavities 1812 separated by at least one partition wall 1916, as shown and described above with reference to FIG. 27. System 2800 includes a plurality of covers 2804. Each cover 2804 of the plurality of covers 2804 includes a cover top 2806 (e.g., a cover top surface) and an opposing cover bottom 2808 (e.g., a cover bottom surface). In the embodiment shown in FIG. 28, at least one cover 2804 of the plurality of covers 2804 also includes a cover grip 2810 coupled to cover top 2806. In other embodiments, not shown, system 2800 does not include cover grip 2810, but rather includes a different structure or structures that provides and facilitates the user 1850 of system 2800 having the ability to grasp, hold, and manipulate cover 2806.

Also, in the embodiment shown in FIG. 28, a first cover 1604a is hingedly coupled to the first basket cavity 1812a (e.g., coupled using at least one hinge 2812) proximate the basket top edge 1806 thereof. For example, and without limitation, a hinge coupled to a rearward 133 portion of basket top edge 114 and coupled to a rearward 133 portion of cover bottom 2808 provides and facilitates user 1850 of device 1600 having the ability to alternately open and close cover 2804 (e.g., by manipulating cover grip 2810) to thereby alternately expose and cover first basket cavity 1812a to exterior 120. Further, in the embodiment shown in FIG. 28, a second cover 2804b is removably coupled to the second basket cavity 1812b proximate the basket top edge 1806 thereof. In still other embodiments, not shown (e.g., embodiments having at least three basket cavities 1812 and at least two partition walls 1916 separating each basket cavity 1812 from each other), at least one basket cavity 1812 of the plurality of basket cavities 1812 does not include cover 2804. Furthermore, in the embodiment shown in FIG. 28, system 2800 includes the at least one container 106 (not shown in FIG. 28) removably coupled to the basket 1802 to facilitate nesting therein through the basket opening 1810. For example, and without limitation, container 106 is nested into first basket cavity 1812 through basket opening 1810 thereof, and is alternately exposed to and covered from exterior 120 by the aforementioned manipulation(s) of first cover 2804a by user 1850.

Figure 29:
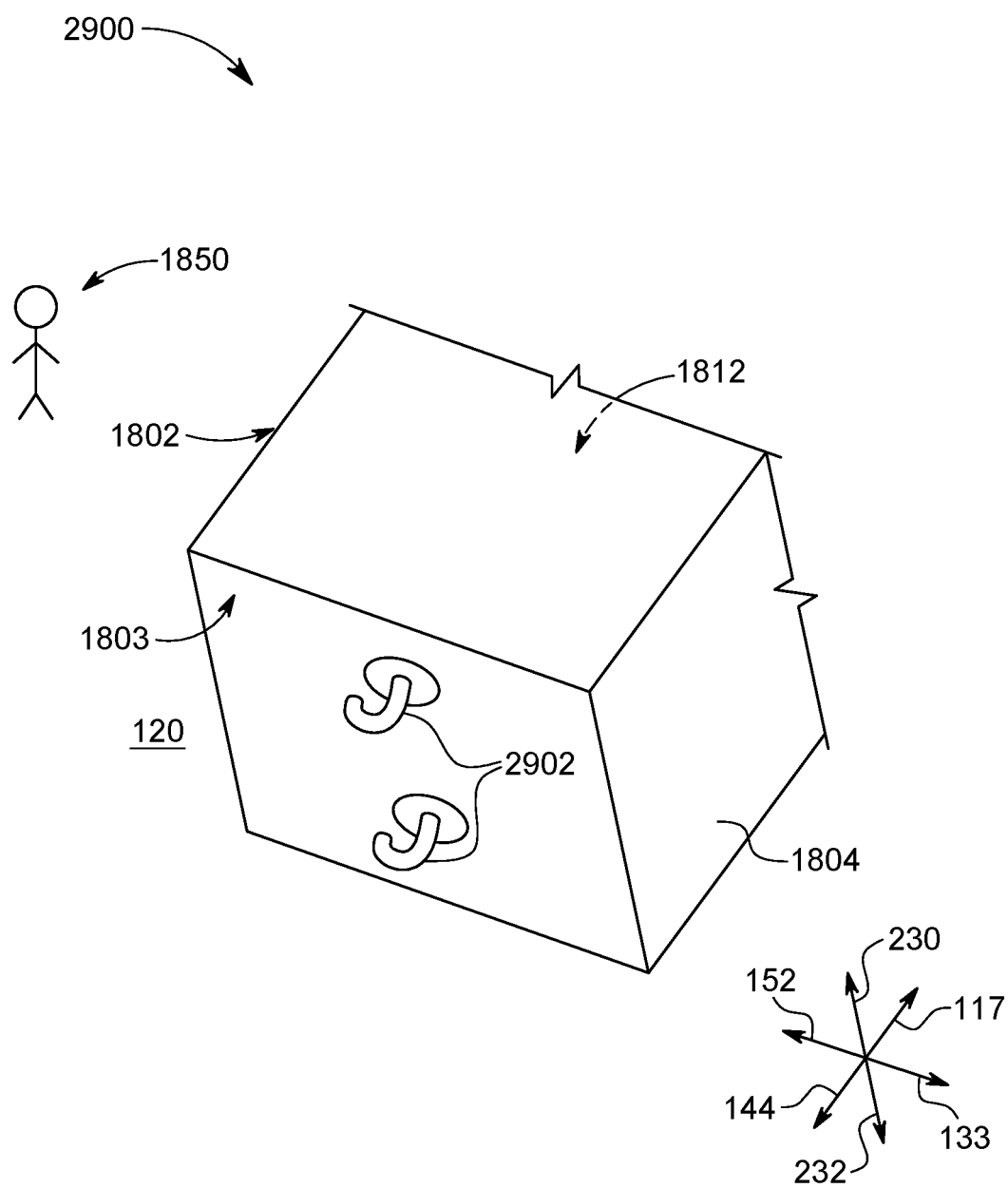
FIG. 29 is a front to rear perspective-view diagram of another embodiment of the devices shown in FIGS. 18-20 and 22, 23, 24A, and 25-28.

FIG. 29 is a front to rear perspective-view diagram of another embodiment of the devices shown in FIGS. 18-20 and 22-28. In the embodiment shown in FIG. 29, a system 2900 includes at least one base hook 2902 coupled to basket base 1803 of basket 1802. In those embodiments of the system including base extension 2502 (e.g., as shown and described above with reference to FIG. 25), the at least one base hook 2902 is coupled to a downward 144 facing surface of base extension 2502. The at least one base hook 2902 provides and facilitates user 1850 having the ability to hang item(s) (e.g., a hand towel, a cleaning implement, etc.) from base hook 2902, including, without limitation, when system 2900 is attached to supportive structure 104 above ground surface 412 (e.g., as shown and described above with reference to FIG. 23).

Figure 30:
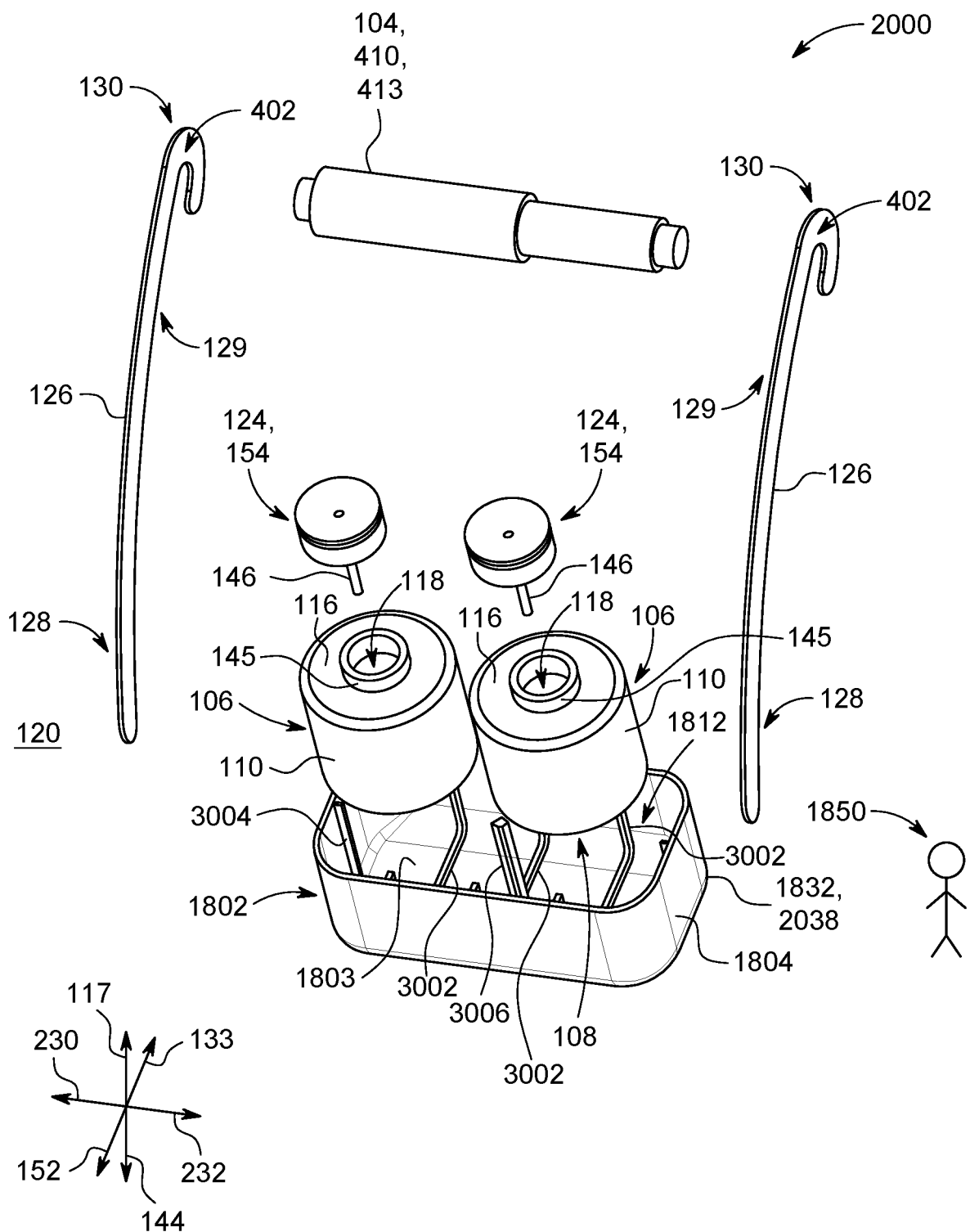
FIG. 30 is a front to rear perspective assembly-view diagram of the system shown in FIG. 20.

FIG. 30 is a front to rear perspective assembly-view diagram of the system (e.g., system 2000) shown in FIG. 20. The assembly view shown in FIG. 30 illustrates several features of basket 1802 that were not depicted in the systems (e.g., system 2000) shown and described above. In the embodiment shown in FIG. 30, basket 1802 includes one basket cavity 1812. At least one longitudinal rib 3002 is formed upon and/or coupled to interior (e.g., facing into basket cavity 1812 from the basket base 1803 and the at least one basket side wall 1804) surfaces of basket 1802. The embodiment shown in FIG. 30 includes three longitudinal ribs 3002 spaced apart from one another in substantially equidistant intervals from the left 230 to the right 232 side of basket 1802.

Longitudinal rib 3002 extends generally upward 117 from the interior facing surface of basket base 1803. Longitudinal rib 3002 also extends generally inward into basket cavity 1812 from the at least one basket side wall 1804. In the embodiment shown in FIG. 30, longitudinal rib 3002 extends upward 117 from basket base 1803 and inward from basket side wall 1804 by a substantially equivalent distance. In other embodiments, not shown, the distance by which longitudinal rib 3002 extends upward 117 from basket base 1803 is not equal to the distance by which longitudinal rib 3002 extends inward from basket side wall 1804. Moreover, longitudinal rib 3002 is formed as one-piece and includes three segments, where one segment of the three segments is coupled to and/or formed upon the interior facing surface of basket base 1803, and two segments of the three segments are coupled to and/or formed upon the interior facing surfaces of the front 152 and rear 133 portions of basket side wall 1804. In other embodiments, not shown, longitudinal rib 3004 is formed in more than one piece, where at least one segment of at least three segments is coupled to and/or formed upon at least one of basket base 1803 and basket side wall 1804 discontinuously with at least one other segment of the at least three segments.

Furthermore, longitudinal rib 3002 does not extend upward from basket base 1803 by the same distance that basket side wall 1804 extends upward from basket base 1803. In other words, a depth of basket cavity 1812 from basket top edge 1806 to basket base 1803 is greater than a height of an upward 117-most surface of longitudinal rib 3002 above basket base 1803. For example, in the embodiment shown in FIG. 30, a ratio of the distance by which longitudinal rib 3002 extends upward 117 from basket base 1803 (and, likewise, the distances by which longitudinal rib 3002 extend frontward 152 from the interior facing surface of the rearward 133 basket side wall 1804 and rearward 133 from the interior facing surface of the frontward 152 basket side wall 1804) as compared to the distance by which basket side wall 1804 extends upward 117 from basket base 1803 is approximately equal to one to forty-eight. For example, and without limitation, in a system 2000 embodiment in which the at least one basket side wall 1804 extends upward 117 from basket base 1803 by six inches (e.g., the depth of basket cavity 1812), the aforementioned height of longitudinal rib 3002 is one-eighth of one inch. In other embodiments, not shown, the height of longitudinal rib 3002 is greater than zero and less than one-eighth of one inch. In still other embodiments, not shown, the height of longitudinal rib 3002 is greater than one-eighth of one inch and less than the basket cavity 1812 depth.

Also, in the embodiment shown in FIG. 30, at least one lateral rib 3004 is formed upon and/or coupled to interior (e.g., facing into basket cavity 1812 from the basket base 1803 and the at least one basket side wall 1804) surfaces of basket 1802. The embodiment shown in FIG. 30 includes one lateral rib 3004 positioned substantially equidistant between the rearward 133 basket side wall 1804 and the frontward 152 basket side wall 1804. In other embodiments, not shown, basket 1802 includes a plurality of lateral ribs 3004 including, without limitation, two or more lateral ribs 3002 spaced apart from one another in substantially equidistant intervals from the front 152 to the rear 133 side of basket 1802.

Lateral rib 3004 extends generally upward 117 from the interior facing surface of basket base 1803. Lateral rib 3002 also extends generally inward into basket cavity 1812 from the at least one basket side wall 1804. In the embodiment shown in FIG. 30, lateral rib 3004 extends upward 117 from basket base 1803 and inward from basket side wall 1804 by a substantially equivalent distance. In other embodiments, not shown, the distance by which lateral rib 3004 extends upward 117 from basket base 1803 is not equal to the distance by which lateral rib 3004 extends inward from basket side wall 1804. Moreover, lateral rib 3004 is formed as one-piece and includes three segments, where one segment of the three segments is coupled to and/or formed upon the interior facing surface of basket base 1803, and two segments of the three segments are coupled to and/or formed upon the interior facing surfaces of the left 230 and right 232 portions of basket side wall 1804. In other embodiments, not shown, lateral rib 3002 is formed in more than one piece, where at least one segment of at least three segments is coupled to and/or formed upon at least one of basket base 1803 and basket side wall 1804 discontinuously with at least one other segment of the at least three segments. [00295] Furthermore, lateral rib 3004 does not extend upward from basket base 1803 by the same distance that basket side wall 1804 extends upward from basket base 1803. In other words, the depth of basket cavity 1812 from basket top edge 1806 to basket base 1803 is greater than a height of an upward 117-most surface of lateral rib 3004 above basket base 1803. For example, in the embodiment shown in FIG. 30, a ratio of the distance by which lateral rib 3004 extends upward 117 from basket base 1803 (and, likewise, the distances by which lateral rib 3004 extend rightward 232 from the interior facing surface of the leftward 230 basket side wall 1804 and leftward 230 from the interior facing surface of the rightward 232 basket side wall 1804) as compared to the distance by which basket side wall 1804 extends upward 117 from basket base 1803 is approximately equal to one to forty-eight. For example, and without limitation, in a system 2000 embodiment in which the at least one basket side wall 1804 extends upward 117 from basket base 1803 by six inches (e.g., the depth of basket cavity 1812), the aforementioned height of lateral rib 3004 is one-eighth of one inch. In other embodiments, not shown, the height of lateral rib 3004 is greater than zero and less than one-eighth of one inch. In still other embodiments, not shown, the height of lateral rib 3004 is greater than one-eighth of one inch and less than the basket cavity 1812 depth.

Further, in the embodiment shown in FIG. 30, basket 1802 does not include partition wall 1916. Rather, system 2000 shown in FIG. 30 includes at least one post 3006 coupled to and/or formed upon basket base 1803 at substantially a center point of the interior facing surface of basket base 1803. In the embodiment shown in FIG. 30, post 3006 is coupled to and/or formed upon basket base 1803 over one of the plurality of longitudinal ribs 3002. In other embodiments, not shown, post 3006 is coupled to and/or formed upon basket base 1803 in a position other than substantially at the center point of the interior facing surface of basket base 1803 (e.g., immediately to the left 230 or to the right 232 of the longitudinal rib 3002 positioned proximate the center point of the interior facing surface of basket base 1803). Post 3006 extends generally upward 117 from basket base 1803 by a height that is substantially equal to the depth of basket cavity 1812. In other embodiments, not shown, post 3006 extends generally upward 117 from basket base 1803 by a height that is greater than zero and less than the depth of basket cavity 1812. In still other embodiments, not shown (e.g., a basket 1802 including one basket cavity 1812 and intended to further include just one container 106 for nesting therein), basket 1802 does not include post 3006.

Figure 31:
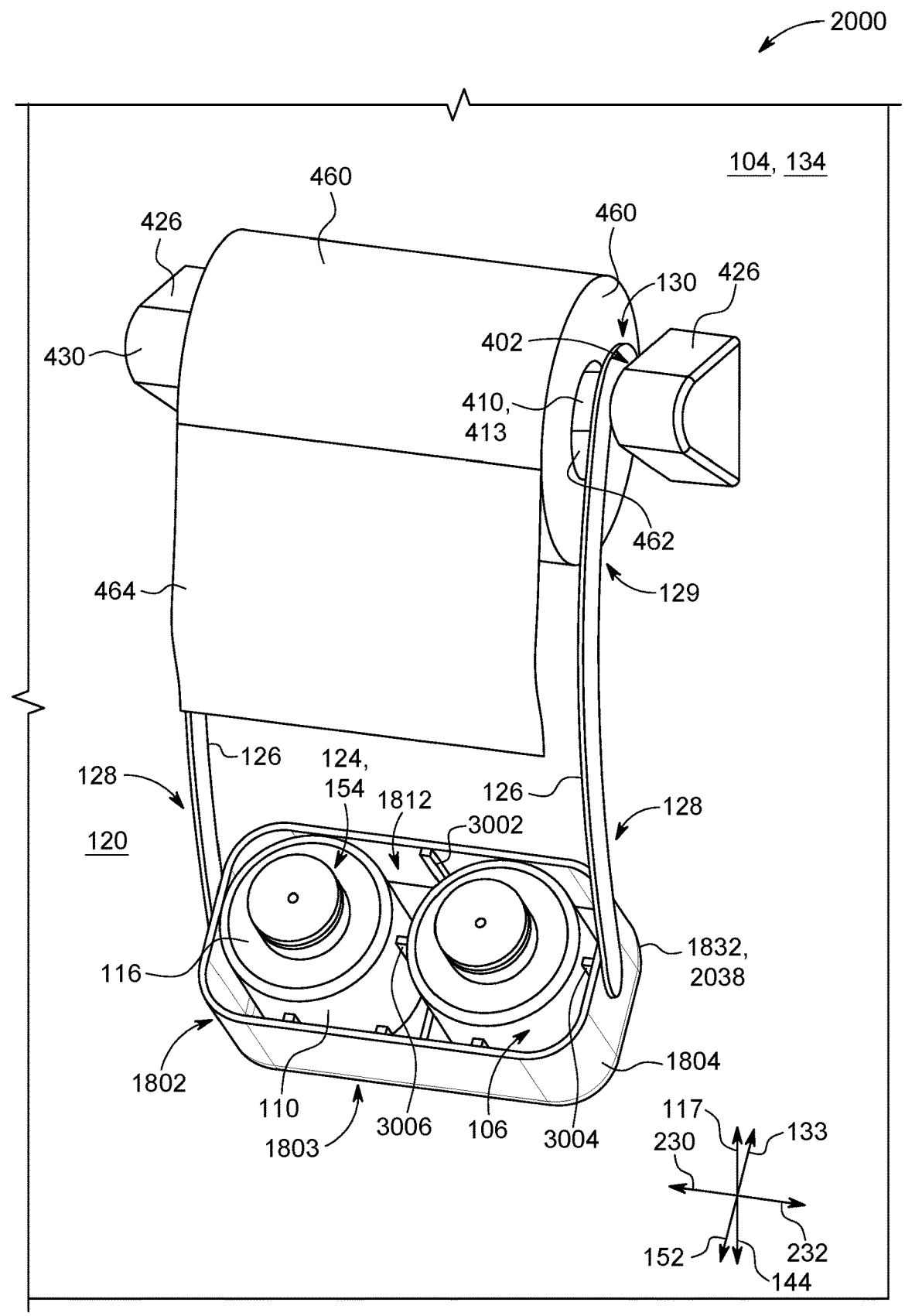
FIG. 31 is a front to rear perspective view diagram of the assembled system shown in FIG. 30.
Figure 32:
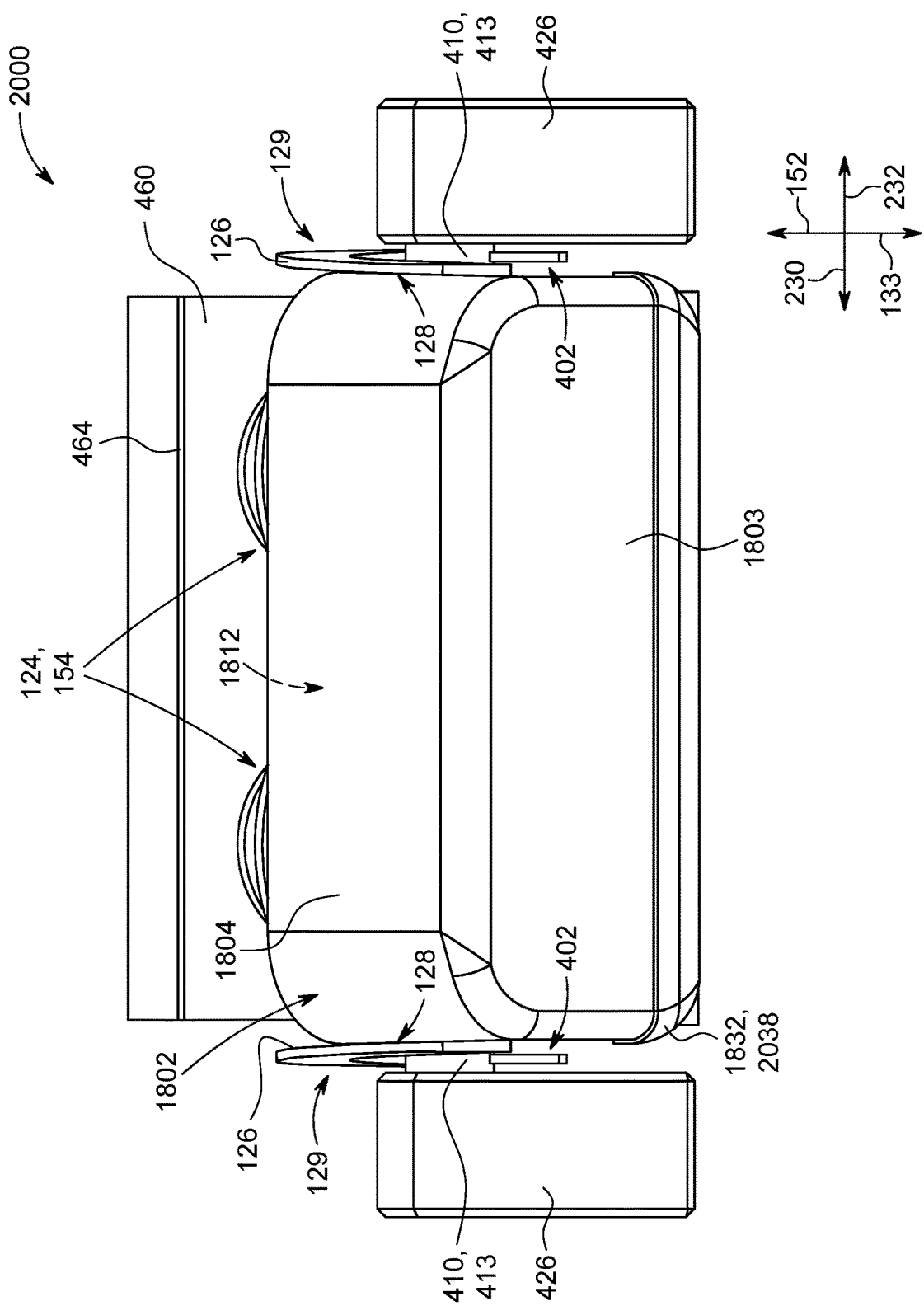
FIG. 32 is a bottom pan view diagram of the assembled system shown in FIG. 30.

FIG. 31 is a front to rear perspective view diagram of the assembled system (e.g., system 2000) shown in FIG. 30. FIG. 32 is a bottom pan view diagram of the assembled system (e.g., system 2000) shown in FIG. 30. In the embodiments of shown in FIGS. 31 and 32, system 2000 is assembled with two containers 106 nested adjacently into basket 1802. Each hanger arm 126 of the two hanger arms 126 includes hook 402 proximate distal end 130. System 2000 is further attached to elongate structure 410 (e.g., bath tissue holder rod 413), and system 2000 hangs therefrom as shown and described above with reference to FIG. 20.

Some embodiments of the systems shown and described above with reference to FIGS. 18-31 also include an antimicrobial coating 490. In those system embodiments including antimicrobial coating 490, antimicrobial coating 490 is applied to an exterior 120 facing surface of at least a portion of least one of: the basket 1802, the container 106, the pump assembly 124, the at least one hanger arm 126, the brace 1906, the brace bumper 1907, the cross-piece 1910, the cross-piece bumper 1912, the hook 402, the bumper 1832, the hook pad 502, the shank pivot point 907, the partition wall 1916, the pin head 911, the flange 915, the lock mechanism 918, the pin head 1011, the flange 1015, the locking mechanism 1018, the first pin head 2311, the first flange 2315, the coupling pivot point 2322, the coupling lock 2324, the second pin head 1164, the second flange 1171, the second arm section pivot point 1172, the lower sleeve 2402, the lower sleeve lock mechanism 2410, the upper sleeve 1216, the upper sleeve lock mechanism 1230, the base extension 2502, the drawer 2510, the drawer 2610, the drawer grip 2558, the under-base cavity 2504, the under-base cavity 2604, the under-base cavity 2718, the cover 2804, the cover grip 2810, the third hanger arm 2716, and the base hook 2902. In some other embodiments, the system further includes antimicrobial coating 490 applied to surfaces of the system other than and/or in addition to those listed above, and which are subject to undesired microbial growth (e.g., bacteria, fungi, algae, viruses, mold, mildew, and the like). In those systems which include antimicrobial coating 490, the undesired microbial growth is at least one of prevented and substantially slowed by the presence of antimicrobial coating 490. Further embodiments of the above-described systems further include antimicrobial agents impregnated into the material(s) of construction of one or more components and/or portions of the system(s), either instead of or in addition to antimicrobial coating 490 applied to surface(s) thereof.

The above-described devices and systems for containing and dispensing liquids are adaptable, without departing from the scope of the present disclosure, to containing and dispensing volumes, amounts, and units of products other than non-pressurized pump-able liquids, including, without limitation, pre-wet paper sheets that are readily biodegradable and materials such as shaving cream and soap foam which require pressurization for removal from container(s) 106 to the exterior 120 of the above described devices and systems. The above described embodiments are readily adaptable to contexts of operation where the apparatus shown is not at least one of removably attached to supportive structure(s) and suspending (e.g., hung) above ground surface 412, but rather are installed by users (e.g., user 150, user 1850) with the intent to at least one of remain in one location indefinitely and have the base (e.g., base 108, basket base 1803) resting upon a surface such as a countertop. Components and features of such other embodiments of the disclosed devices and systems benefit users in a substantially similar manner (e.g., convenience, ergonomic advantage, sturdiness and stability during pumping and other operational manipulations) as the disclosed embodiments intended for at least one of removable attachment to supportive structure(s) and for hanging from supportive structure(s) 104 above ground surface 412 and other surfaces such as countertops.

The above described devices and systems for containing and dispensing liquids provide convenient co-location of liquid cleaning and personal hygiene products, and related and associated items and materials, to preferred places of use. The above described embodiments also provide for co-location of cloths, towels, swabs, pads, wipes with liquid containers having conveniently operated pump assemblies, and which are readily exchangeable and refillable by users. The embodiments shown and described above are compact, modular, versatile, and manufactured and assembled in a cost-effective and efficient manner from a variety of low cost, but durable and long-lasting materials. Component parts of the above described embodiments need not be strictly disposable, but rather are re-usable by users of longer periods of time as compared to known apparatus, and thereby mitigate undesirable negative impacts to water quality and environmental and human health due to slower biodegradation of disposable materials in known apparatus. The above described embodiments further provide sturdy and stable structural features and components to facilitate removable attachment of the apparatus herein disclosed from one place to another place. Through modularity of design, the embodiments described above reduce the need of users to purchase a plurality of different units to use in a plurality of different locations within home, business, and industrial settings. The modular and adjustable features and components in the disclosed embodiments also reduces the need of users to install a plurality of supportive structures to facilitate mounting and employing a plurality of desired liquid products in a plurality of locations, which would take up otherwise useable space, and would compound the environment and health concerns described above. The embodiments described above also modularly and effectively integrate pump assemblies into their design to provide numerous benefits to users including, without limitation, stability of the disclosed apparatus during pumping motions, speed, convenience, and ergonomic advantages (e.g., requiring using only one hand to transfer desired volumes of liquid out of containers by pumping) to users during the various manipulations of the apparatus during operation, as described above. Moreover, the embodiments described above provide stable and sturdy, yet removable attachment (e.g., through hanging attachment) of the apparatus to a wide variety of shapes, sizes, and types of supportive structures, which reduces undesired recurrent contact (e.g., bumping) of the disclosed apparatus relative to known devices and systems. Structural pieces of the embodiments described above further include modular and adjustable features to facilitate accommodating a single unit of the apparatus to a plurality of locations, installation methods, user preferences, user physiological characteristics, and varying shapes, sizes, and types of available supportive structures. The versatility thus provided by the above described devices and systems for containing and dispensing liquids provides users low cost and high longevity apparatus which facilitate convenient co-location of liquid cleaning and personal hygiene products, and related and associated items and materials, to preferred places of use.

An exemplary technical effect of the devices, systems, and associated methods described herein includes at least one of: (a) providing convenient co-location of liquid cleaning and personal hygiene products, and related and associated items and materials, to preferred places of use; (b) providing for co-location of cloths, towels, swabs, pads, wipes, and other useful items with liquid containers having conveniently operated pump assemblies, and which are readily exchangeable and refillable by users; (c) facilitating compact, modular and versatile products that are manufactured and assembled in a cost-effective and efficient manner from a variety of low cost, but durable and long-lasting materials; (d) reducing undesirable negative impacts to water quality and environmental and human health due to slower biodegradation of disposable materials found in known apparatus; (e) providing sturdy and stable structural features and components to facilitate removable attachment of the disclosed apparatus from one place to another place; (f) reducing the need of users to purchase a plurality of different product units to use in a plurality of different locations within home, business, and industrial settings; (g) reducing the need of users to install a plurality of supportive structures to facilitate mounting and employing a plurality of desired liquid products in a plurality of locations, which would take up otherwise useable space, and would compound the environment and health concerns described above; (h) modularly and effectively integrating pump assemblies into apparatus to provide numerous benefits to users including, without limitation, stability of the disclosed apparatus during pumping motions, speed, convenience, and ergonomic advantages (e.g., requiring using only one hand to transfer desired volumes of liquid out of containers by pumping) to users during the various manipulations of the apparatus during operation, as described above; (i) providing stable and sturdy, yet removable attachment (e.g., through hanging attachment) of the apparatus to a wide variety of shapes, sizes, and types of supportive structures, which reduces undesired recurrent contact (e.g., bumping) of the disclosed apparatus relative to known devices and systems; (j) facilitating accommodating a single unit of the apparatus to a plurality of locations, installation methods, user preferences, user physiological characteristics, and varying shapes, sizes, and types of available supportive structures; and (k) providing users low cost and high longevity apparatus which facilitate convenient co-location of liquid cleaning and personal hygiene products, and related and associated items and materials, to preferred places of use.

Exemplary embodiments of the above-described devices and systems for containing and dispensing liquids are not limited to the specific embodiments described herein, but rather, components of the devices and systems, and/or steps of associated methods may be utilized independently and separately from other components and/or steps described herein. For example, the devices, systems, and methods may also be used in combination with other material containment and dispensing apparatus requiring improvements in, for example, and without limitation, convenience, modularity, versatility, ergonomic performance, reduction in number of associated equipment pieces required, and enhancement of efficiency and versatility of manufacturing processes for such devices and systems, and the associated methods are not limited to practice with only the devices, systems, and methods as described herein. Rather, exemplary embodiments can be implemented and utilized in connection with many other applications, equipment, and systems that may benefit from using the above-described embodiments of the above-described devices, systems, and methods for containing and dispensing liquids to improve the performance, reduce the cost, size, and/or weight, and enhance the versatility, effectiveness, manufacturing and distribution efficiency, and user experience of material containment and dispensing apparatus generally and methods associated therewith, and other related devices and systems in various applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A device comprising:
    a container;
    a pump assembly coupled to the container and extending into an interior cavity thereof; and
    at least one hanger arm coupled to the container, the at least one hanger arm including a first section proximate to the container and a second section distal the container,
    wherein the container includes: a container base, and a base extension coupled to and extending generally downward from the container base, the base extension including an under-base cavity defined within the base extension, the under-base cavity including an under-base opening facing generally frontward, the under-base cavity extending generally rearward through at least a portion of the base extension.

2. The device according to claim 1, wherein the pump assembly comprises a dish-top pump.

3. The device according to claim 1, wherein the second section includes a distal end formed as a generally downward facing hook.

4. The device according to claim 1, wherein the first section includes a proximate end, said device further comprising a lower sleeve coupled to the container, the lower sleeve extending distally from the container, the lower sleeve including a lower sleeve cavity defined within the lower sleeve and having a lower sleeve opening positioned opposite, and facing away from, the container, the lower sleeve cavity extending from the lower sleeve opening to a lower sleeve bottom, and wherein the proximate end is slidingly coupled to the lower sleeve through the lower sleeve cavity.

5. The device according to claim 4 further comprising a lower sleeve lock mechanism coupled to the lower sleeve and selectively coupled to the first section.

6. The device according to claim 1, wherein the at least one hanger arm further includes a midsection positioned, and defining an approximate boundary, between the first section and the second section, said device further comprising a sleeve at least one of: coupled to and formed in, a first end of the midsection, the sleeve including a sleeve cavity defined within the sleeve and having a sleeve opening positioned opposite, and facing away from, the midsection, the sleeve cavity extending from the sleeve opening to a sleeve bottom, wherein the first section includes a distal end slidingly coupled to the sleeve through the sleeve cavity.

7. The device according to claim 6 further comprising a sleeve lock mechanism coupled to the sleeve and selectively coupled to the first section.

8. The device according to claim 1, wherein the second section includes a distal end, said device further comprising a sleeve at least one of: coupled to, and formed within, the second section, the sleeve extending generally downward from the distal end, the sleeve including a sleeve cavity defined within the sleeve and having a sleeve opening facing generally downward, the sleeve opening extending generally upward from the sleeve opening to a sleeve top, wherein an upper end of the second section is slidingly coupled to the sleeve through the sleeve cavity.

9. The device according to claim 8 further comprising a sleeve lock mechanism coupled to the sleeve and selectively coupled to the second section.

10. A system comprising:
    a basket;
    at least one container for nesting in at least one basket cavity of the basket, the at least one container including a pump assembly coupled to the at least one container and extending into an interior cavity of the container; and
    at least one hanger arm coupled to the basket, the at least one hanger arm including a first section proximate to the basket and a second section distal the basket,
    wherein the basket includes: a basket base, and a base extension coupled to and extending generally downward from the basket base, the base extension including an under-base cavity defined within the base extension, the under-base cavity including an under-base opening facing generally frontward, the under-base cavity extending generally rearward through at least a portion of the base extension.

11. The system according to claim 10, wherein the basket includes at least one basket side wall, and wherein a rearward facing portion of the basket includes an arcuate fillet formed at a juncture of a rearward facing portion of the basket base and a rearward facing portion of the at least one basket side wall, the arcuate fillet being concavely formed with respect to the at least one basket cavity.

12. The system according to claim 11 further comprising a bumper coupled to an exterior rearward facing surface of the arcuate fillet.

13. The system according to claim 10, wherein the second section includes a distal end formed as a generally downward facing hook.

14. The system according to claim 10, wherein the at least one hanger arm further includes two hanger arms.

15. The system according to claim 10, wherein the at least one hanger arm is rotatably coupled to the basket.

16. The system according to claim 10, wherein the first section and the second section are rotatably coupled together.

17. The system according to claim 10, wherein the first section includes a proximate end, said system further comprising a lower sleeve coupled to the basket, the lower sleeve extending generally upward from the basket, the lower sleeve including a lower sleeve cavity defined within the lower sleeve and having a lower sleeve opening positioned opposite, and facing away from, the basket, the lower sleeve cavity extending from the lower sleeve opening to a lower sleeve bottom, and wherein the proximate end is slidingly coupled to the lower sleeve through the lower sleeve cavity.

18. The system according to claim 10, wherein the at least one hanger arm further includes a midsection positioned, and defining an approximate boundary, between the first section and the second section, said system further comprising a sleeve at least one of: coupled to, and formed in, a first end of the midsection, the sleeve including a sleeve cavity defined within the sleeve and having a sleeve opening positioned opposite, and facing away from, the midsection, the sleeve cavity extending from the sleeve opening to a sleeve bottom, wherein the first section includes a distal end slidingly coupled to the sleeve through the sleeve cavity.

19. The system according to claim 18 further comprising a sleeve lock mechanism coupled to the sleeve and selectively coupled to the first section.

20. The system according to claim 10, wherein the second section includes a distal end, said system further comprising a sleeve at least one of: coupled to, and formed within, the second section, the sleeve extending generally downward from the distal end, the sleeve including a sleeve cavity defined within the sleeve and having a sleeve opening facing generally downward, the sleeve opening extending generally upward from the sleeve opening to a sleeve top, wherein an upper end of the second section is slidingly coupled to the sleeve through the sleeve cavity.

21. The system according to claim 20 further comprising a sleeve lock mechanism coupled to the sleeve and selectively coupled to the second section.

22. The system according to claim 10, wherein the under-base cavity further extends generally rearward entirely through the base extension from the first under-base opening to a second under-base opening, the second under-base opening facing generally rearwardly.

23. The system according to claim 10, wherein the second section includes a distal end configured for alternate attachment to and removal from a supportive structure.

24. The system according to claim 10, wherein the basket includes a basket top edge, said system further comprising at least one cover, wherein the at least one cover is at least one of:
  removably coupled to the at least one basket cavity proximate the basket top edge thereof; and
  hingedly coupled to the at least one basket cavity proximate the basket top edge thereof.

25. A device comprising:
  a container including: a base, and at least one side wall, wherein a rearward facing portion of the container includes an arcuate fillet formed at a juncture of a rearward facing portion of the base and a rearward facing portion of the at least one side wall, the arcuate fillet being concavely formed with respect to an interior cavity of the container;
  a pump assembly coupled to the container and extending into an interior cavity thereof; and
  at least one hanger arm coupled to the container, the at least one hanger arm including a first section proximate to the container and a second section distal the container.

26. The device according to claim 25 further comprising a bumper coupled to an exterior rearward facing surface of the arcuate fillet.

27. The device according to claim 25, wherein the second section includes a distal end configured for alternate attachment to and removal from a supportive structure.

28. A system comprising:
  a basket including: a base, and at least one side wall, wherein a rearward facing portion of the basket includes an arcuate fillet formed at a juncture of a rearward facing portion of the base and a rearward facing portion of the at least one side wall, the arcuate fillet being concavely formed with respect to at least one basket cavity of the basket;
  at least one container for nesting in the at least one basket cavity of the basket, the at least one container including a pump assembly coupled to the at least one container and extending into an interior cavity of the container; and
  at least one hanger arm coupled to the basket, the at least one hanger arm including a first section proximate to the basket and a second section distal the basket.

29. The system according to claim 28 further comprising a bumper coupled to an exterior rearward facing surface of the arcuate fillet.

30. The system according to claim 28, wherein the second section includes a distal end configured for alternate attachment to and removal from a supportive structure.

* * * * *